US012516053B2

(12) United States Patent

Xue et al.

(10) Patent No.: US 12,516,053 B2

(45) Date of Patent: Jan. 6, 2026

(54) BCL-2 INHIBITORS

(71) Applicant: BEIGENE, LTD., Grand Cayman (KY)

(72) Inventors: Hai Xue, Beijing (CN); Yunhang Guo, Beijing (CN); Zhiwei Wang, Beijing (CN)

(73) Assignee: BeOne Medicines I GmbH, Basel (CH)

(*) Notice: Subject to any disclaimer, the term of this patent is extended or adjusted under 35 U.S.C. 154(b) by 876 days.

(21) Appl. No.: 17/771,871

(22) PCT Filed: Oct. 27, 2020

(86) PCT No.: PCT/CN2020/123939

§ 371 (c)(1),
(2) Date: Apr. 26, 2022

(87) PCT Pub. No.: WO2021/083135

PCT Pub. Date: May 6, 2021

(65) Prior Publication Data

US 2023/0002369 A1 Jan. 5, 2023

(30) Foreign Application Priority Data

Oct. 28, 2019 (WO) ................ PCT/CN2019/113776

(51) Int. Cl.
*C07D 471/02* (2006.01)
*C07D 413/04* (2006.01)
*C07D 498/14* (2006.01)

(52) U.S. Cl.
CPC ......... *C07D 471/02* (2013.01); *C07D 413/04* (2013.01); *C07D 498/14* (2013.01)

(58) Field of Classification Search
CPC ... C07D 471/02; C07D 413/04; C07D 498/14
USPC .......................................................... 546/113
See application file for complete search history.

(56) References Cited

U.S. PATENT DOCUMENTS

| | | | | |
|---|---|---|---|---|
| 11,420,968 | B2 * | 8/2022 | Guo | C07D 207/09 |
| 11,718,611 | B2 | 8/2023 | Wang | |
| 12,077,536 | B2 * | 9/2024 | Guo | C07D 471/14 |
| 2002/0055631 | A1 | 5/2002 | Augeri et al. | |
| 2011/0124628 | A1 | 5/2011 | Bruncko et al. | |
| 2011/0237553 | A1 | 9/2011 | Ding et al. | |
| 2011/0312969 | A1 | 12/2011 | East | |
| 2012/0189539 | A1 | 7/2012 | Wang et al. | |
| 2012/0214796 | A1 | 8/2012 | Ding et al. | |
| 2013/0245005 | A1 | 9/2013 | Sorba et al. | |
| 2020/0397895 | A1 | 12/2020 | Levy | |
| 2021/0269433 | A1 | 9/2021 | Guo et al. | |
| 2022/0402915 | A1 | 12/2022 | Guo | |

FOREIGN PATENT DOCUMENTS

| | | | |
|---|---|---|---|
| CN | 102448959 | A | 5/2012 |
| CN | 102947283 | A | 2/2013 |
| CN | 103237797 | A | 8/2013 |
| CN | 103562202 | A | 2/2014 |
| CN | 106565706 | A | 4/2017 |
| CN | 106749233 | A | 5/2017 |
| CN | 110143974 | A | 8/2019 |
| CN | 110177788 | A | 8/2019 |
| WO | WO-0224636 | A2 | 3/2002 |
| WO | 2005049593 | A2 | 6/2005 |
| WO | 2006023778 | A2 | 3/2006 |
| WO | 2006127364 | A1 | 11/2006 |
| WO | 2007040650 | A2 | 4/2007 |
| WO | 2008030836 | A2 | 3/2008 |
| WO | 2009036051 | A1 | 3/2009 |
| WO | 2009152082 | A1 | 12/2009 |
| WO | 2009155386 | A1 | 12/2009 |
| WO | 2010065824 | A2 | 6/2010 |
| WO | 2010065865 | A2 | 6/2010 |
| WO | 2010067067 | A1 | 6/2010 |
| WO | 2010083441 | A2 | 7/2010 |
| WO | 2010083442 | A1 | 7/2010 |
| WO | WO-2010138588 | A2 | 12/2010 |
| WO | 2011029842 | A1 | 3/2011 |
| WO | 2011068561 | A1 | 6/2011 |
| WO | WO-2011119345 | A2 | 9/2011 |
| WO | WO-2011149492 | A1 | 12/2011 |
| WO | WO-2011150016 | A1 | 12/2011 |
| WO | 2012017251 | A1 | 2/2012 |
| WO | 2012058392 | A1 | 5/2012 |
| WO | WO-2012073184 | A1 | 6/2012 |
| WO | WO-2012103059 | A2 | 8/2012 |
| WO | 2012162365 | A1 | 11/2012 |
| WO | 2013053045 | A1 | 4/2013 |
| WO | 2013096049 | A1 | 6/2013 |
| WO | 2013096050 | A1 | 6/2013 |

(Continued)

OTHER PUBLICATIONS

Extended European Search Report issued in App. No. EP20880525, dated Oct. 24, 2023, 6 pages.
Adams, J. M. et al. (2007) The Bcl-2 apoptotic switch in cancer development and therapy. Oncogene 26:1324-1337.
Anderson, M. A. et al. (2014) Targeting BCL2 for the treatment of lymphoid malignancies. Semin Hematol 51:219-227.
Czabotar, P. E. et al. (2014) Control of apoptosis by the BCL-2 protein family: implications for physiology and therapy. Nat Rev Mol Cell Biol 15:49-63.
Egle, A. et al. (2004) VavP-Bcl2 transgenic mice develop follicular lymphoma preceded by germinal center hyperplasia. Blood 103:2276-2283.
International Search Report and Written Opinion for International Application No. PCT/CN2019/085001, mailed Jul. 26, 2019, 12 pages.

(Continued)

*Primary Examiner* — Kristin A Vajda
(74) *Attorney, Agent, or Firm* — McNeill PLLC

(57) ABSTRACT

Disclosed herein is a compound of Formula (I) for inhibiting Bcl-2 and treating disease associated with undesirable bcl-2 activity (Bcl-2 related diseases), a method of using the compounds disclosed herein for treating dysregulated apoptotic diseases including cancers and treating autoimmune disease, and a pharmaceutical composition comprising the same.

18 Claims, No Drawings

(56) References Cited

FOREIGN PATENT DOCUMENTS

| | | | |
|---|---|---|---|
| WO | 2013096051 | A1 | 6/2013 |
| WO | 2013096055 | A1 | 6/2013 |
| WO | 2013096060 | A1 | 6/2013 |
| WO | 2013185202 | A1 | 12/2013 |
| WO | 2014113413 | A1 | 7/2014 |
| WO | 2014158528 | A1 | 10/2014 |
| WO | 2014173289 | A1 | 10/2014 |
| WO | 2016024230 | A1 | 2/2016 |
| WO | WO-2017132474 | A1 | 8/2017 |
| WO | 2018009444 | A1 | 1/2018 |
| WO | 2018027097 | A1 | 2/2018 |
| WO | 2018041248 | A1 | 3/2018 |
| WO | 2018127130 | A1 | 7/2018 |
| WO | WO-2018192462 | A1 | 10/2018 |
| WO | 2019001383 | A1 | 1/2019 |
| WO | 2019040550 | A1 | 2/2019 |
| WO | WO-2019040573 | A1 | 2/2019 |
| WO | 2019081559 | A1 | 5/2019 |
| WO | WO-2019210828 | A1 | 11/2019 |
| WO | 2020024834 | A1 | 2/2020 |
| WO | 2020024916 | A1 | 2/2020 |
| WO | WO-2020140005 | A2 | 7/2020 |
| WO | WO-2021083135 | A1 | 5/2021 |
| WO | WO-2021110102 | A1 | 6/2021 |
| WO | 2021208963 | A1 | 10/2021 |
| WO | 2022256489 | A1 | 12/2022 |

OTHER PUBLICATIONS

International Search Report and Written Opinion for International Application No. PCT/CN2020/123939, mailed Jan. 4, 2021, 15 pages.
International Search Report and Written Opinion for International Application No. PCT/CN2020/133636, mailed Feb. 26, 2021, 13 pages.
Kondo, S. et al. (2008) Rescue of renal hypoplasia and cystic dysplasia in Bcl-2 −/− mice expressing Bcl-2 in ureteric bud derived epithelia. Dev Dyn 237:2450-2459.
Liu, X. et al. (2018) "Development of high potent and selective Bcl-2 inhibitors bearing the structural elements of natural product artemisinin," European Journal of Medicinal Chemistry, 159:149-165.
Roberts, A. W. (2016) Targeting apoptotic pathways to treat lymphoid malignancies. Rinsho Ketsueki 57:2054-2058.
Roberts, A. W. et al. (2017) Targeting BCL2 With BH3 Mimetics: Basic Science and Clinical Application of Venetoclax in Chronic Lymphocytic Leukemia and Related B Cell Malignancies. Clin. Pharmacol. Ther., 101:89-98.
Schenk, R. L. et al. (2017) BCL-2: Long and winding path from discovery to therapeutic target. Biochem Biophys Res Commun 482:459-469.
Tausch, E. et al. (2019) Venetoclax resistance and acquired BCL2 mutations in chronic lymphocytic leukemia. Haematologica 104:e434-e437.
Veis, D. J. et al. (1993) Bcl-2-deficient mice demonstrate fulminant lymphoid apoptosis, polycystic kidneys, and hypopigmented hair. Cell, 75:229-240.
Written Opinion for Singapore Application No. 11202009933W, dated Mar. 10, 2022, 7 pages.
Yamamura, K. et al., "Accelerated disappearance of melanocytes in bcl-2-deficient mice," Cancer Res vol. 56, pp. 3546-3550 (Aug. 1996).
US Final Office Action for U.S. Appl. No. 17/771,871, dated May 7, 2025, (17 pages).
Ashkenazi, A. et al, "From basic apoptosis discoveries to advanced selective BCL-2 family inhibitors," Nature Reviews Drug Discovery, 16(4):273-84, 2017.
Balar, A. V. et al., "Atezolizumab as first-line treatment in cisplatin-ineligible patients with locally advanced and metastatic urothelial carcinoma: a single-arm, multicentre, phase 2 trial," Lancet, 389(10064):67-76, 2017.
Blombery, P. et al., "Acquisition of the recurrent Gly101Val mutation in BCL2 confers resistance to venetoclax in patients with progressive chronic lymphocytic leukemia," Cancer Discovery, 9(3):342-53, 2019.
Bold, R. et al., "BCL2 expression correlates with metastatic potential in pancreatic cancer cell lines," Cancer: Interdisciplinary International Journal of the American Cancer Society, 92(5):1122-9, 2001.
Cang, S. et al., "ABT-199 (venetoclax) and BCL-2 inhibitors in clinical development," Journal of Hematology & Oncology, 8(1):1-8, 2015.
Chipuk, J. et al., "The BCL-2 family reunion," Molecular Cell, 37(3):299-310, 2010.
Cookson, B. et al., "Pro-inflammatory programmed cell death," Trends in Microbiology, 9(3):113-4, 2001.
Coultas, L. et al., "The role of the Bcl-2 protein family in cancer," Seminars in Cancer Biology, 13(2):115-123, 2003.
Dinardo, C.D., et al., "Venetoclax combined with decitabine or azacitidine in treatment-naive, elderly patients with acute myeloid leukemia," Blood, 133(1):7-17, 2019.
Hanahan et al., "Hallmarks of Cancer: The Next Generation", Cell, 144(5): 646-674, 2011.
Hennessy, E., "Selective inhibitors of Bcl-2 and Bcl-xL: Balancing antitumor activity with on-target toxicity," Bioorganic & Medicinal Chemistry Letters, 26(9):2105-14, 2016.
Hillmen, P., et al., "Ibrutinib Plus Venetoclax in Relapsed/Refractory Chronic Lymphocytic Leukemia: The Clarity Study," J Clin Oncol, 37(30):2722-2729, 2019.
International Search Report and Written Opinion for International Application No. PCT/CN2021/087225, mailed Jul. 14, 2021, 11 pages.
International Search Report and Written Opinion for International Application No. PCT/US2022/031782, mailed Aug. 29, 2022, 11 pages.
International Search Report and Written Opinion for International Application No. PCT/US2022/031903, mailed Aug. 25, 2022, 12 pages.
Jain, N., "Ibrutinib and Venetoclax for First-Line Treatment of CLL," N Engl J Med, 381(8):788-789, 2019.
Kerr, J. F. R. et al., "Apoptosis: A Basic Biological Phenomenon With Wide-Ranging Implications In Tissue Kinetics," Br. J. Cancer, 26: 239-257, 1972.
Letai, A., "Diagnosing and exploiting cancer's addiction to blocks in apoptosis," Nature Reviews Cancer, 8(2):121-32, 2008.
Lochmuller, C. H. et al., "Chromatographic Resolution of Enantiomers," Journal of Chromatography, 113:283-302, 1975.
Masood, A., "Small molecule inhibitors of bcl-2 family proteins for pancreatic cancer therapy," Cancers, 3(2):1527-49, 2011.
Mohammad, R., "Small-molecule inhibitors of Bcl-2 family proteins as therapeutic agents in cancer," Recent patents on anti-cancer drug discovery, 3(1):20-30, 2008.
Placzek, W.J., et al., "A survey of the anti-apoptotic Bcl-2 subfamily expression in cancer types provides a platform to predict the efficacy of Bcl-2 antagonists in cancer therapy," Cell Death Disease, 1(e40): 1-9, 2010.
Poeta G. et al., "Deregulation of the mitochondrial apoptotic machinery and development of molecular targeted drugs in acute myeloid leukemia," Current Cancer Drug Targets, 8(3):207-22, 2008.
Roberts, A. W. et al., "Targeting BCL2 with Venetoclax in Relapsed Chronic Lymphocytic Leukemia", The New England Journal of Medicine, 374:311-322, 2016.
Seymour, J.F., et al., "Venetoclax plus rituximab in relapsed or refractory chronic lymphocytic leukaemia: a phase lb study," Lancet Oncol, 2017, vol. 18, No. 2, pp. 230-240, 2017.
Tam, C. S. et al., "Phase 1 study of the selective BTK inhibitor zanubrutinib in B-cell malignancies and safety and efficacy evaluation in CLL," The American Society of Hematology, 134(11): 851-859, 2019.
Tsujimoto, Y. et al., "Analysis of the structure, transcripts, and protein products of bcl-2, the gene involved in human follicular lymphoma," Proc Natl Acad Sci, 83(14):5214-5218, 1986.
Vogelstein, B. et al., "Cancer genes and the pathways they control," Nature Medicine, 10(8):789-99, 2004.

(56) References Cited

OTHER PUBLICATIONS

Wilson, W. H. et al., "Navitoclax, a targeted high-affinity inhibitor of BCL-2, in lymphoid malignancies: a phase 1 dose-escalation study of safety, pharmacokinetics, pharmacodynamics, and antitumour activity", Lancet Oncol., 11(12):1149-59, 2010.

* cited by examiner

BCL-2 INHIBITORS

CROSS-REFERENCE TO RELATED APPLICATIONS

This application is a U.S. National Stage Application under 35 U.S.C. § 371 of International Application No. PCT/CN2020/123939, filed Oct. 27, 2020, which claims priority to Patent Application No. PCT/CN2019/113776 (CN), filed Oct. 28, 2019.

FIELD OF THE DISCLOSURE

Disclosed herein is a compound of Formula (I) for inhibiting Bcl-2 and treating disease associated with undesirable bcl-2 activity (Bcl-2 related diseases), a method of using the compounds disclosed herein for treating dysregulated apoptotic diseases including neurodegenerative conditions, e.g., Alzheimer's disease; and proliferative diseases, e.g., cancers, autoimmune diseases and pro-thrombotic conditions, and a pharmaceutical composition comprising the same.

BACKGROUND OF THE DISCLOSURE

Programmed cell death or apoptosis occurs in multicellular organisms to dispose damaged or unwanted cells, which is critical for normal tissue homeostasis. (Br. J. Cancer 1972, 26, 239). However defective apoptotic processes have been implicated in a wide variety of diseases. Excessive apoptosis causes atrophy, whereas an insufficient amount results in uncontrolled cell proliferation, such as cancer (Cell 2011, 144, 646). Resistance to apoptotic cell death is a hallmark of cancer and contributes to chemoresistance (Nat Med. 2004, 10, 789-799). Several key pathways controlling apoptosis are commonly altered in cancer. Some factors like Fas receptors and caspases promote apoptosis, while some members of the B-cell lymphoma 2 (Bcl-2) family of proteins inhibit apoptosis. Negative regulation of apoptosis inhibits cell death signaling pathways, helping tumors to evade cell death and developing drug resistance.

There are two distinct apoptosis pathways including the extrinsic pathway and the intrinsic pathway. The extrinsic pathway is activated in response to the binding of death-inducing ligands to cell-surface death receptors (Nat Rev Drug Discov. 2017 16, 273-284). The B cell lymphoma 2 (BCL-2) gene family, a group of proteins homologous to the Bcl-2 protein, encodes more than 20 proteins that regulate the intrinsic apoptosis pathway. Bel-2 family proteins are characterized by containing at least one of four conserved Bcl-2 homology (BH) domains (BH1, BH2, BH3 and BH4) (Nat. Rev. Cancer 2008, 8, 121; Mol. Cell 2010, 37, 299; Nat. Rev. Mol. Cell Biol. 2014, 15, 49). Bcl-2 family proteins, consisting of pro-apoptotic and anti-apoptotic molecules, can be classified into the following three subfamilies according to sequence homology within four BH domains: (1) a subfamily shares sequence homology within all four BH domains, such as Bcl-2, Bcl-XL and Bcl-w which are anti-apoptotic; (2) a subfamily shares sequence homology within BH1, BH2 and BH4, such as Bax and Bak which are pro-apoptotic; (3) a subfamily shares sequence homology only within BH3, such as Bik, Bid and HRK which are pro-apoptotic. One of the unique features of Bcl-2 family proteins is heterodimerization between anti-apoptotic and pro-apoptotic proteins, which is considered to inhibit the biological activity of their partners. This heterodimerization is mediated by the insertion of a BH3 region of a pro-apoptotic protein into a hydrophobic cleft composed of BH1, BH2 and BH3 from an anti-apoptotic protein. In addition to the BH1 and BH2, the BH4 domain is required for anti-apoptotic activity. In contrast, BH3 domain is essential and, itself, sufficient for pro-apoptotic activity.

Similar to oncogene addiction, in which tumor cells rely on a single dominant gene for survival, tumor cells may also become dependent on Bcl-2 in order to survive. Bcl-2 overexpress is found frequently in acute myeloid leukemia (AML), acute lymphocytic leukemia (ALL), relapsed/refractory chronic lymphocytic leukemia (CLL), follicular lymphoma (FL), non-Hodgkin lymphoma (NHL) and solid tumors such as pancreatic, prostate, breast, and small cell and non-small cell lung cancers (Cancer 2001, 92, 1122-1129; Cancer Biol. 2003; 13:115-23; Curr. Cancer Drug Targets 2008, 8, 207-222; Cancers 2011, 3, 1527-1549). Dysregulated apoptotic pathways have also been implicated in the pathology of other significant diseases such as neurodegenerative conditions (up-regulated apoptosis), e.g., Alzheimer's disease; and proliferative diseases (down-regulated apoptosis), e.g., cancers, autoimmune diseases and pro-thrombotic conditions. Target to either Bcl-2 or Bcl-xL, a number of small-molecule BH3 mimetics have been reported in (Recent Patents on Anti-Cancer Drug Discovery, 2008, 3, 20-30; Bioorg. Med. Chem. Lett. 2016, 26, 2105-2114; Nature Reviews Drug Discovery 2017, 16, 273-284; WO2002024636; WO2005049593; WO2006127364; WO2006023778; WO2007040650; WO2008030836; WO2009152082; WO2009036051; WO2010065824; WO2010065865; WO2010083441; WO2010083442; WO2010067067; WO2011029842; WO2011068561; WO2011119345; WO2011149492; WO2011150016: WO2012058392; WO2012017251; WO2012162365; WO2012103059; WO2013053045; WO2013185202; WO2013096060; WO2013096059; WO2013096055; WO2013096051; WO2013096049; US2011312969; WO2014158528; WO2014113413; WO2018027097; WO2018041248; WO2018009444; WO2018127130; WO2018192462; WO2019001383; WO2019040550; WO2019040573; WO2019081559; CN106749233; CN106565706; CN110143974). Some of the Bcl-2 small molecule inhibitors have been investigated at various stages of drug development: the Bcl-2/Bcl-xL inhibitor ABT-263 (navitoclax, WO2009155386) has shown promising clinical activity in lymphoid malignancies such as chronic lymphocytic leukemia. However, its efficacy in these settings is limited by platelet death and attendant thrombocytopenia caused by Bcl-xL inhibition (Lancet Oncol. 2010, 11, 1149; J. Clin. Oncol. 2011, 29, 909; J. Clin. Oncol. 2012, 30, 488). The new generation of the BCL-2 selective inhibitor venetoclax (ABT-199/GDC-0199) was proceeded, which demonstrated robust activity in these cancers but also spared platelets (Journal of Hematology & Oncology 2015, 8, 129; Clinical Advances in Hematology & Oncology 2017, 15, 210). S55746 (also known as BCL201), APG-101, APG-1252 are being studied at clinical trial stage. Currently, Venetoclax (formerly ABT-199) is the only Bcl-2 selective inhibitor approved by FDA for the treatment of patients who have relapsed or refractory chronic lymphocytic leukemia (CLL) with the 17p deletion. Recently, however, a novel Gly101Val mutation in BCL2 was identified after the patients were treated with the Bcl-2 inhibitor venetoclax (ABT-199) for 19 to 42 months (Cancer Discov. 2019, 9, 342-353). This mutation dramatically reduced the binding affinity of Bcl-2 for Venetoclax (ABT-199) by about 180-fold in cell based assay.

Therefore, there is a need of new small molecules that selectively inhibit Bcl-2 proteins for the treatment of dysregulated apoptotic diseases such as cancers, autoimmune diseases and pro-thrombotic conditions. Unexpectedly, the inventors of the present application found some compounds disclosed herein show much higher potency. Also, the inventors of the present application found that the compounds disclosed herein exhibit inhibitory activity against both Bcl-2 wild type and Bcl-2 G101V mutation type, suggesting a type of new potential Bcl-2 inhibitors without resistance concern.

SUMMARY OF THE DISCLOSURE

Disclosed herein is a compound of Formula (I)

(I)

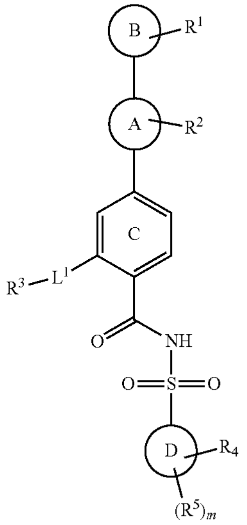

or a pharmaceutically acceptable salt thereof, or a stereoisomer thereof, wherein $L^1$ is a direct bond, and —O—;

Ring A is cycloalkyl, cycloalkenyl, cycloalkynyl, aryl, heterocyclyl, or heteroaryl, each of which is optionally substituted with 1 to 4 substituents $R^{2}$:

$R^2$, at each occurrence, is independently selected from the group consisting of hydrogen, deuterium, halogen, or —$C_{1-8}$ alkyl optionally substituted with halogen;

Ring B is heterocyclyl containing one heteroatom selected from nitrogen (N), sulfur (S) and oxygen (O), or heteroaryl, each of which is optionally substituted with 1 to 4 substituents $R^{1}$; $R^1$, at each occurrence, is independently selected from the group consisting of deuterium, cycloalkyl, heterocyclyl, aryl, or heteroaryl; wherein said cycloalkyl, heterocyclyl, aryl or heteroaryl are each independently optionally substituted with 1 to 4 substituents $R^{1d}$, $R^{1d}$, at each occurrence, is independently halogen, —$C_{1-8}$ alkyl, —$C_{2-8}$alkenyl, —$C_{2-8}$alkynyl, cycloalkyl, heterocyclyl, aryl, heteroaryl, oxo, —CN, —$NO_2$, or —$OR^{Ba}$; wherein said —$C_{1-8}$alkyl, —$C_{2-8}$alkenyl, —$C_{2-8}$alkynyl, cycloalkyl, heterocyclyl, aryl or heteroaryl are each independently optionally substituted with 1 to 4 substituents $R^{Bd}$;

$R^{Ba}$, and $R^{Bb}$, are each independently hydrogen, —$C_{1-8}$ alkyl, —$C_{2-8}$alkenyl, —$C_{2-8}$alkynyl, cycloalkyl, heterocyclyl, aryl, or heteroaryl, each of said —$C_{1-8}$alkyl, —$C_{2-8}$ alkenyl, —$C_{2-8}$alkynyl, cycloalkyl, heterocyclyl, aryl, or heteroaryl is optionally substituted with halogen, hydroxy, —$NH_2$ or —$N(C_{1-6}alkyl)_2$, —$C_{1-8}$alkyoxy, cycloalkyl, heterocyclyl, aryl, or heteroaryl;

$R^3$ is heteroaryl,

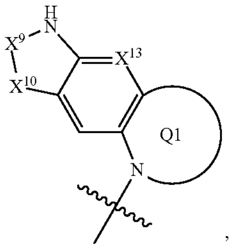

,

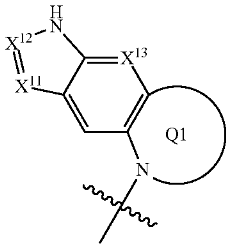

,

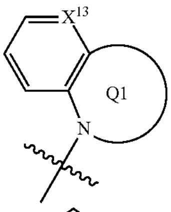

,

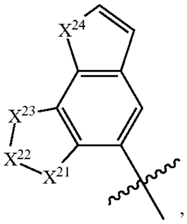

,

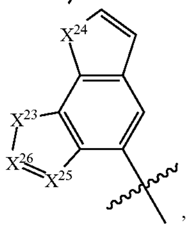

, or

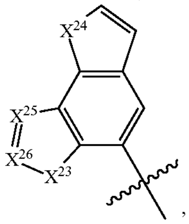

, each of which is optionally substituted with 1 to 4 substituents $R^{3a}$, wherein $Q^1$ is heterocycloalkyl or heterocycloalkenyl, and $X^9$, $X^{10}$, $X^{21}$, $X^{22}$, $X^{23}$ and $X^{24}$ are each independently O, NH, or $CH_2$, and $X^{11}$, $X^{12}$, $X^{13}$, $X^{25}$, and $X^{26}$ are each independently N or CH;

$R^{3a}$, at each occurrence, is independently selected from halogen, cyano, —$NO_2$, —$OR^{3b}$, —$SR^{3b}$, —$NR^{3b}R^{3c}$, -oxo-, —$COR^{3b}$, —$SO_2R^{3b}$, —C(=O)$OR^{3b}$, —C(=O) $NR^{3b}R^{3c}$, —C(=$NR^{7b}$)$NR^{3c}R^{1d}$, —N($R^{3b}$)C(=O)$R^{3c}$, —N($R^{3b}$)C(=O)$OR^{1c}$, —$NR^{3b}SO_2R^{3c}$, —$C_{1-8}$alkyl, —$C_{2-8}$ alkenyl, —$C_{2-8}$alkynyl, -cycloalkyl, heterocyclyl, aryl, or heteroaryl;

$R^{3b}$, and $R^{3c}$ are independently hydrogen, —$C_{1-8}$alkyl, —$C_{2-8}$alkenyl, —$C_{2-8}$alkynyl, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or hetero aryl is optionally substituted with halogen, hydroxy or —$C_{1-8}$ alkyoxy;

Ring D is aryl or

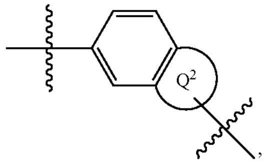

, each of which is optionally substituted with 1 to 4 substituents $R^4$;

$Q^2$ is a heterocycloalkyl;

$R^4$, at each occurrence, is independently selected from the group consisting of -hydrogen, alkyl, alkenyl, alkynyl, cycloalkyl, cycloalkyl-alkyl, heterocyclyl, heterocyclyl-alkyl, aryl, aryl-alkyl, heteroaryl, heteroaryl-alkyl, halogen, —CN, —$NO_2$, —$(CR^{4c}R^{4d})_zNR^{4a}R^{4b}$, —$(CR^{4c}R^{4d})OR^{4b}$, —$(CR^{4c}R^{4d})_zC(O)R^{4a}$, —$(CR^{4c}R^{4d})_zC(=NR^{4e})R^{4a}$, —$(CR^{4c}R^{4d})_zC(=N—OR^{4b})R^{4a}$, —$(CR^{4c}R^{4d})_zC(O)OR^{4b}$, —$(CR^{4c}R^{4d})_zOC(O)R^{4b}$, —$(CR^{4c}R^{4d})_zC(O)NR^{4a}R^{4b}$, —$(CR^{4a}R^{4d})_zNR^{4a}C(O)R^{4b}$, —$(CR^{4c}R^{4d})_zC(=NR^{4e})NR^{4a}R^{4b}$, —$(CR^{4c}R^{4d})_zNR^{4a}C(=NR^{4e})R^{4b}$, —$(CR^{4c}R^{4d})_zOC(O)NR^{4a}R^{4b}$, —$(CR^{4c}R^{4d})_zNR^{4a}C(O)OR^{4b}$, —$(CR^{4c}R^{4d})_zNR^{4a}C(O)NR^{4a}R^{4b}$, —$(CR^{4c}R^{4d})_zNR^{4a}C(S)NR^{4a}R^{4b}$, —$(CR^{4c}R^{4d})_zNR^{4a}C(=NR^{4e})NR^{4a}R^{4b}$, —$(CR^{4a}R^{4b})_zS(O)_rR^b$, —$(CR^{4c}R^{4d})_zS(O)(=NR^{4e})R^{4b}$, —$(CR^{4c}R^{4d})_zN=S(O)R^{4a}R^{4b}$, —$(CR^{4c}R^{4}d)_zS(O)_2OR^{4b}$, —$(CR^{4c}R^{4d})_zOS(O)_2R^{4e}$, —$(CR^{4c}R^{4}d)_zNR^{4a}S(O)_rR^{4b}$, —$(CR^{4c}R^{4d})_zNR^{4a}S(O)(=NR^{4e})R^{4b}$, —$(CR^{4c}R^{4d})_zS(O)_rNR^{4a}R^{4b}$, —$(CR^{4c}R^{4d})_zS(O)(=NR^{4e})NR^{4c}R^{4b}$, —$(CR^{4c}R^{4d})_zNR^{4a}S(O)_2NR^{4a}R^{4b}$, —$(CR^{4c}R^{4d})_zNR^{4a}S(O)(=NR^{4e})NR^{4a}R^{4b}$, —$(CR^{4c}R^{4d})_zP(O)R^{4a}R^{4b}$ and —$(CR^{4c}R^{4}d)_zP(O)(OR^{4a})(OR^{4b})$, wherein each $R^{4a}$ and each $R^{4b}$ are independently selected from hydrogen, alkyl, alkenyl, alkynyl, cycloalkyl, cycloalkyl-alkyl, heterocyclyl, heterocyclyl-alkyl, aryl, aryl-alkyl, heteroaryl and heteroaryl-alkyl; each $R^{4c}$ and each $R^{4d}$ are independently selected from hydrogen, halogen, alkyl, alkenyl, alkynyl, cycloalkyl, cycloalkyl-alkyl, heterocyclyl, heterocyclyl-alkyl, aryl, aryl-alkyl, heteroaryl and heteroaryl-alkyl; z, at each occurrence, is independently a number of 1 to 8; and r, at each occurrence, is independently a number of 1 or 2;

m is an integer of 1-4, preferably m is 1;

$R^5$ is -$L^2$-CyC,

Wherein $L^2$ is a direct bond, —$(CR^aR^b)_t$—, —O—$(CR^aR^b)_t$—, —S—, —S(O)—, —$SO_2$—, —C(O)—, C(O)O—, —OC(O)—, —$NR^a$—, —$N(R^a)(CR^aR^b)_t$, —$(CR^aR^b)_tC(O)NR^a$—, —$C(O)NR^a$—, —$(CR^aR^b(NR^a)_t$—C(O)—, —$NR^aC(O)$—, —$NR^aC(O)O$—, —$NR^aC(O)NR^b$—, —$SO_2NR^a$—, —$NR^aSO_2$—, —$NR^aS(O)_2NR^b$—, —$NR^aS(O)NR^b$—, —$C(O)NR^aSO_2$—, —$C(O)NR^aSO$—, or —$C(=NR^a)NR^b$—, wherein t, at each occurrence, is independently a number of 0 to 7, and one or two $CR^aR^b$ moieties in —$(CR^aR^b)_t$— is un-replaced or replaced with one or more moieties selected from O, S, SO, $SO_2$, C(O) and $NR^a$; $R^a$ and $R^b$ are independently hydrogen or —$C_{1-3}$alkyl;

Cyc is —$SO_2R^{5a}$—, cycloalkyl, heterocyclyl, aryl, or heteroaryl, each of said cycloalkyl, heterocyclyl, aryl, or heteroaryl are optionally substituted with one or two substituents $R^{5a}$;

$R^{5a}$, at each occurrence, is independently selected from hydrogen, halogen, cyano, oxo, —$NO_2$, —$OR^{5b}$, —$SR^{5b}$, —$NR^{5b}R^{5c}$, —$COR^{5b}$, —$C_{1-8}$alkyl, —$C_{2-8}$alkenyl, and —$C_{2-8}$alkynyl, -cycloalkyl, or heterocyclyl, each of said —$C_{1-8}$alkyl, and heterocyclyl is optionally substituted with one or two substituents $R^5$ which is selected from hydrogen, halogen, cyano, —$OR^{5f}$, —$C_{1-8}$alkyl, -cycloalkyl, or heterocyclyl;

wherein $R^{5b}$ and $R^{5c}$ are each independently hydrogen, —$C_{1-8}$alkyl, —$C_{2-8}$alkenyl, —$C_{2-8}$alkynyl, cycloalkyl, heterocyclyl, aryl, or heteroaryl, said —$C_{1-8}$alkyl is optionally substituted with one or two substituents $R^{5e}$ which is hydrogen, —$NR^{5f}R^{5g}$, or -cycloalkyl; and $R^{5f}$ and $R^{5g}$ are each independently hydrogen or —$C_{1-8}$alkyl.

In one embodiment, $L^1$ is a direct bond or —O—.

In one embodiment, $R^3$ is

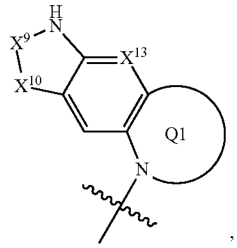
,
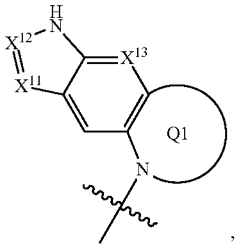
,
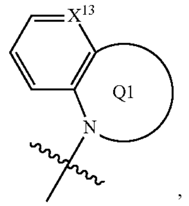
, each of which is optionally substituted with one or two substituents $R^{3a}$ as defined with Formula (I), and, $Q^1$ is 6- to 8-membered heterocycloalkyl or 6- to 8-membered heterocycloalkenyl, each of $X^9$, $X^{10}$, $X^{11}$, $X^{12}$ and $X^{13}$ is defined as above.

In one embodiment, $R^3$ is

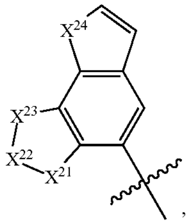
,
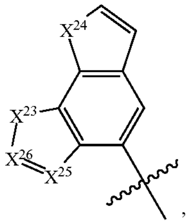
, or
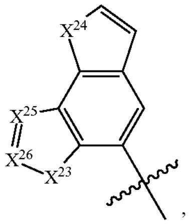
, each of which is optionally substituted with one or two substituents $R^{3a}$ as defined with Formula (I), and each of $X^{21}$, $X^{22}$, $X^{23}$, $X^{24}$, $X^{25}$, and $X^{26}$ is defined as above.

In one embodiment, $R^3$ is heteroaryl optionally substituted with one or two substituents $R^{3a}$ as defined with Formula (I).

In one embodiment, $R^3$ is an 8- to 12-membered bicyclic heteroaryl comprising 1 or 2 or 3 nitrogen atoms. In one embodiment, $R^3$ is indolyl, pyrrolopyridiny, or pyrazolopyridinyl, each of which optionally substituted with one or two substituents $R^{3a}$ selected from halogen, —$C_{1-8}$alkyl, or —$NR^{3b}R^{3c}$, wherein $R^{3b}$ and $R^{3c}$ are independently hydrogen, or —$C_{1-8}$alkyl. In a preferred embodiment, $R^3$ is indol-4-yl, pyrrolo[2,3-b]pyridin-5-yl, and pyrazolo[4,3-b]pyridin-1-yl.

In one embodiment, $R^3$ is 11- to 14-membered tricyclic heteroaryl comprising 1 or 2 or 3 or 4 or 5 nitrogen atoms optionally substituted with one or two substituents $R^{31}$ selected from halogen, —$C_{1-8}$alkyl, or —$NR^{3b}R^{3c}$, wherein $R^{3b}$ and $R^{3c}$ are independently hydrogen, or —$C_{1-8}$alkyl In a preferred embodiment, $R^{3a}$ is selected from halogen, $—NR^{3b}R^{3c}$, -oxo-, $—C_{1-8}$alkyl, wherein $R^{3b}$ and $R^{3c}$ are independently hydrogen or $—C_{1-8}$alkyl.

In a referred embodiment R3 is selected from

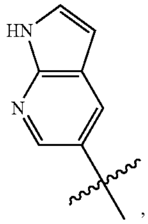
,
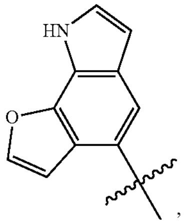
,
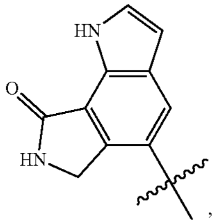
,
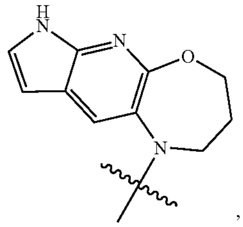
,
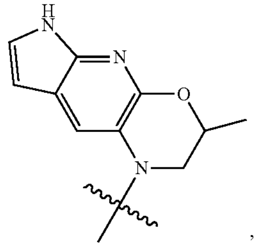
,
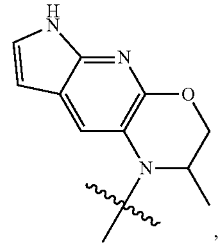
,
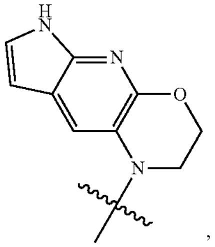
,
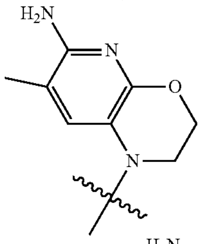
,
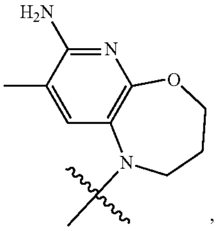
, and
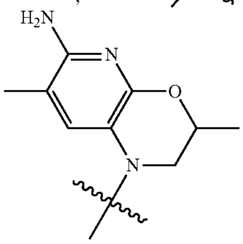
.

In one embodiment, D is

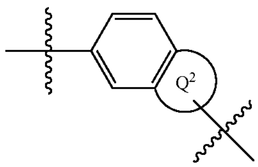

optionally substituted with one or two substituents $R^4$ as defined with Formula (I), and $Q^2$ is a 5-membered to 8-membered heterocycloalkyl containing at least one of heteroatom independently selected from N, O and S.

In one embodiment, $R^3$ is heteroaryl optionally substituted with one or two substituents $R^{3a}$ as defined with Formula (I). Preferably, $R^3$ is heteroaryl optionally substituted with one or two substituents $R^{3a}$ selected from halogen, $—C_{1-8}$alkyl, or $—NR^{3b}R^{3c}$, wherein $R^{3b}$ and $R^{3c}$ are independently hydrogen, or $—C_{1-8}$alkyl.

In one embodiment, D is phenyl optionally substituted with one or two substituents $R^4$ as defined with Formula (I).

In one embodiment, ring D is selected from

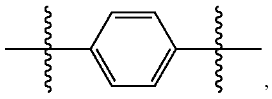
,
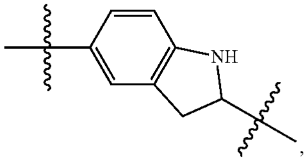
,
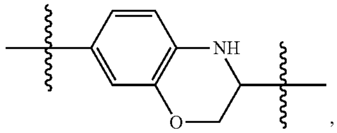
,
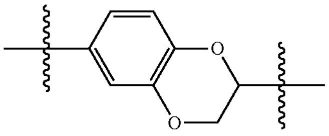
and
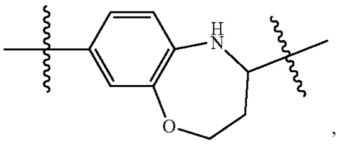
, which is substituted with optionally substituted with one or two substituents $R^4$ as defined with Formula (I). Preferably, ring D is selected from

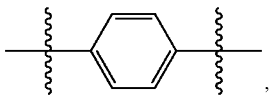
,
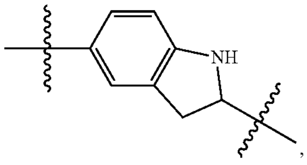
,
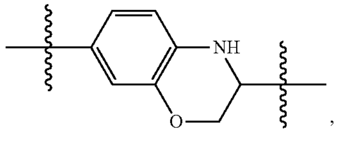
,
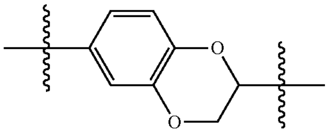
and

-continued

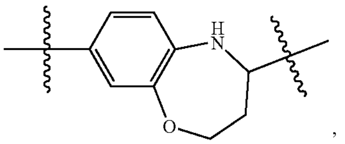

which is substituted with —$NO_2$ on the phenyl ring, and/or further optionally substituted with one substituent $R^4$ on $Q^2$ ring, and said $R^4$ is as defined with Formula (I).

In one embodiment, ring A is 5-membered to 12-membered spiro heterocyclyl comprising one or two heteroatoms selected from nitrogen (N), sulfur (S) and oxygen (O) as ring members; preferably ring A is 4-membered/4-membered, 3-membered/5-membered, 4-membered/5-membered, 4-membered/6-membered, 5-membered/5-membered, or 5-membered/6-membered mono-spiro heterocyclyl comprising one or two nitrogen or oxygen as ring members. More specifically, ring A is

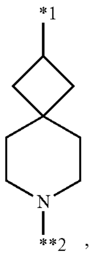

(7-azaspiro[3.5] nonan-2, 7-diyl)

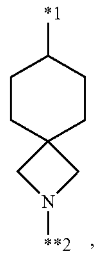

(2-azaspiro[3.5] nonan-2, 7-diyl)

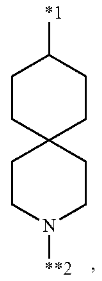

(3-azaspiro[5.5] undecan-3, 9-diyl)

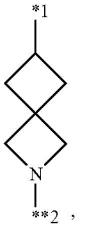

(2-azaspiro[3.3] heptan-2, 6-diyl)

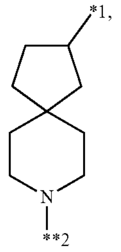

(8-azaspiro[4.5] decan-2, 8-diyl)

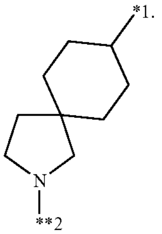

(2-azaspiro[4.5] decan-2, 8-diyl)

Specifically, ring A is heterocyclic which is piperidine, pyrrolidine, and azetidine: 7-azaspiro[3,5]nonane, 2-azaspiro[3,5]nonane, 8-azabicyclo[3.2.1]octane; tetrahydrothienopyridine (e.g., 4,5,6,7-tetrahydrothieno[2,3-c]pyridine), tetrahydropyrrolopyrazine (e.g., 1,2,3,4-tetrahydropyrrolo[1,2-a]pyrazine), tetrahydropyrrolopyrazine (e.g., 1,2,3,4-tetrahydropyrrolo[1,2-a]pyrazine), hexahydroindolizine (e.g., 1,2,3,5,8,8a-hexahydroindolizine), dihydropyrrolothiazole (e.g., 5,6-dihydro-4H-pyrrolo[3,4-d]thiazole), or isoindoline.

In an even preferred embodiment, ring A is selected from the group consisting of:

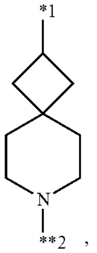

(7-azaspiro[3.5] nonan-2, 7-diyl)

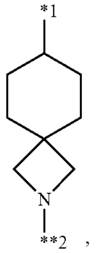

(2-azaspiro[3.5] nonan-2, 7-diyl)

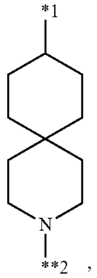

(3-azaspiro[5.5] undecan-3, 9-diyl)

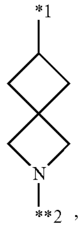

(2-azaspiro[3.3] heptan-2, 6-diyl)

wherein *1 refers to the position attached to the ring B, and **2 refers to the position attached to the phenyl ring.

In one embodiment, $R^2$ is hydrogen, deuterium, halogen (e.g., F, Cl or Br) or $C_{1-6}$alkyl (e.g., methyl) optionally substituted with halogen (e.g., F, Cl or Br), preferably, $R^2$ is hydrogen or deuterium.

In one embodiment, ring B is aziridin-1-yl, azetidin-1-yl, pyrrolidin-1-yl, pyrrolidin-2-yl, azepan-1-yl, or azocan-1-yl, preferably pyrrolidin-1-yl and which is substituted with a phenyl group at position 2, and said phenyl group at position 2 (i.e., ortho position) is optionally substituted with $R^{1d}$ as defined with Formula (I).

In one aspect of this embodiment, $R^{1d}$, when substituted on the phenyl group at position 2 of ring B (including the aziridin-1-yl, azetidin-1-yl, pyrrolidin-1-yl, pyrrolidin-2-yl, azepan-1-yl, or azocan-1-yl, preferably the pyrrolidin-1-yl group), is independently halogen, —$C_{1-8}$alkyl, —$C_{2-8}$ alkenyl, —$C_{2-8}$alkynyl, cycloalkyl, heterocyclyl, aryl, heteroaryl, —CN, —$OR^{Ba}$, —$SO_2R^{Ba}$, —$CONR^{Ba}R^{Bb}$, —$NO_2$, —$NR^{Ba}R^{Bb}$, —$NR^{Ba}COR^{Bb}$, or —$NR^{B}SO_2R^{Bb}$; wherein said —$C_{1-8}$alkyl, —$C_{2-8}$alkenyl, —$C_{2-8}$alkynyl, cycloalkyl, heterocyclyl, aryl or heteroaryl are each independently optionally substituted with 1 to 4 substituents $R^{Bd}$ as defined with Formula (I), preferably 1 or 2 substituents $R^{Bd}$ as defined with Formula (I). In another aspect, one $R^{1d}$ is at position 2 of the phenyl ring at position 2 of ring B.

In one aspect $R^{1d}$ is methyl, ethyl, isopropyl, propyl or methoxymethyl, or two methyl at position of the phenyl ring; or propenyl; or cyclopropyl, cyclobutyl, cyclopentyl, or cyclohexyl; or ethoxy or isopropoxy; or amino or dimethylamino.

In a preferred embodiment, the 2-(2-substituted phenyl) pyrrolidin-1-yl moiety as ring B is selected from the group consisting of:

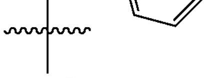

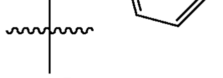

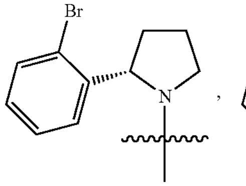

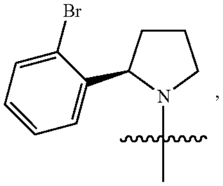

-continued
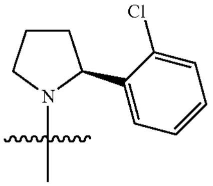 , 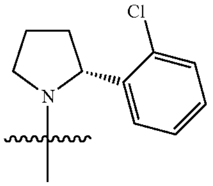 ,
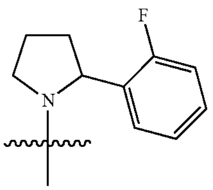 ; 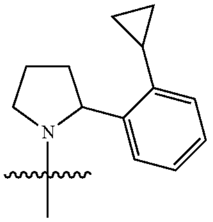 ,
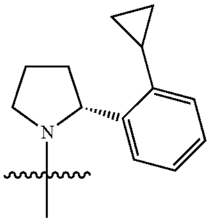 , 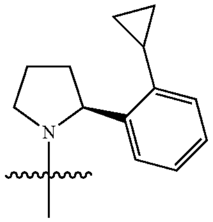 ,
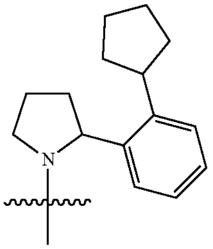 , 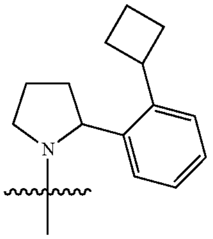 ,
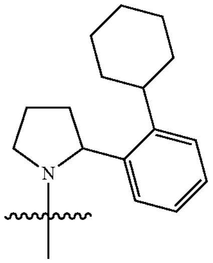 , 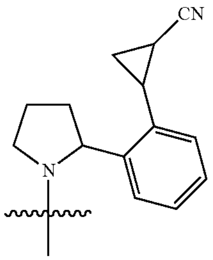 ,
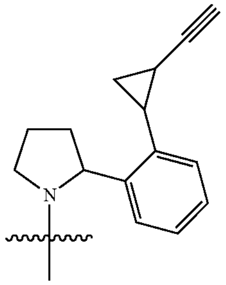 , 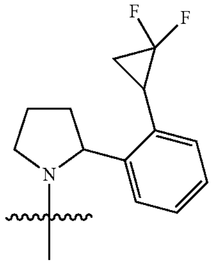 ,
-continued
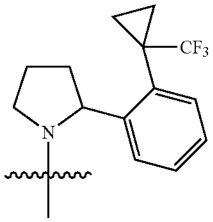 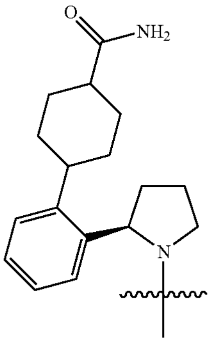 ,
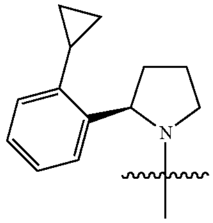 , 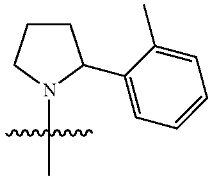 ,
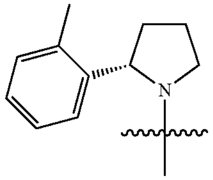 , 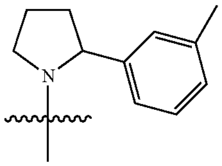 ,
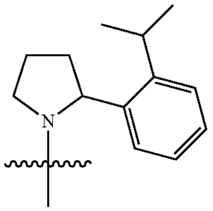 , 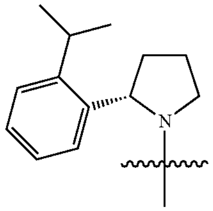 ,
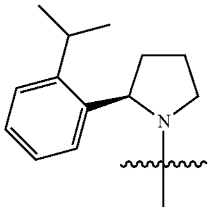 , 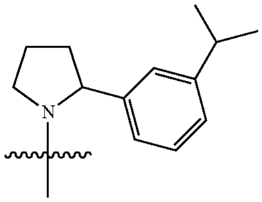 ,
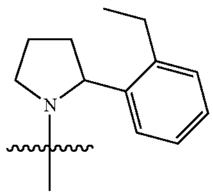 , 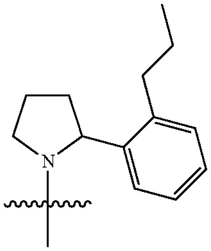 ,
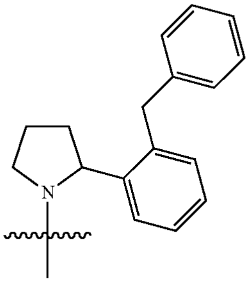 , 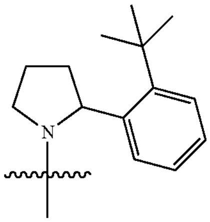 , -continued
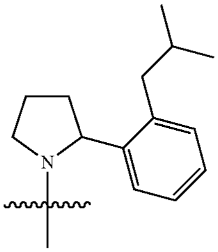,
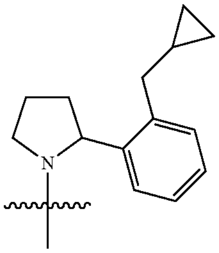,
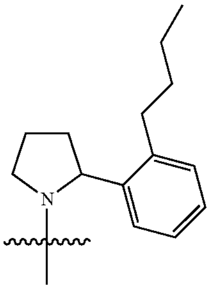,
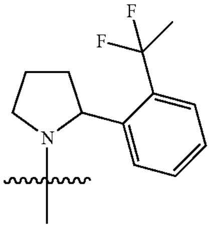,
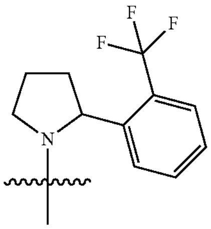,
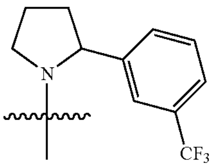,
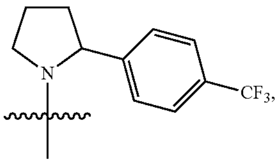
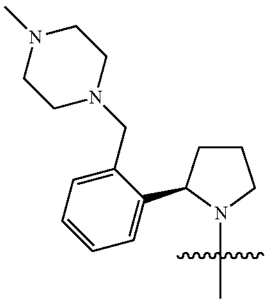,
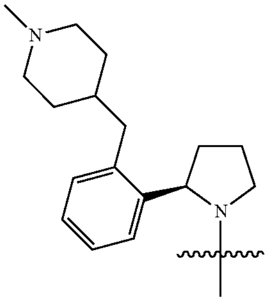,
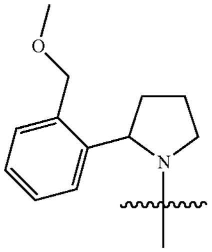,
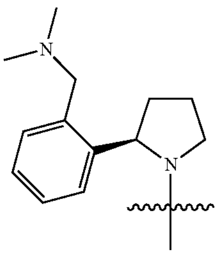,
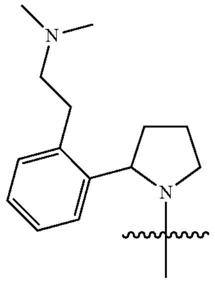,
-continued
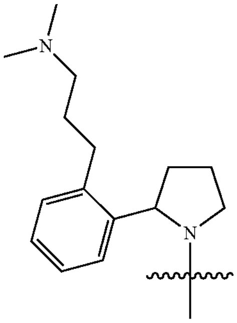,
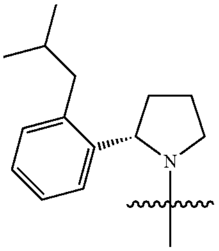,
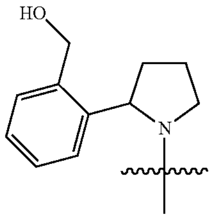,
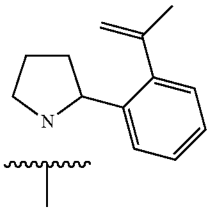,
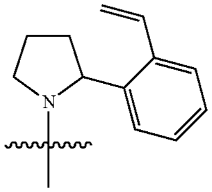,
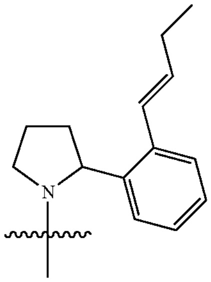,
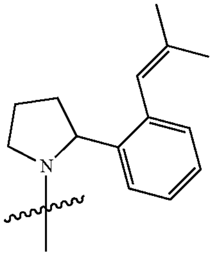;
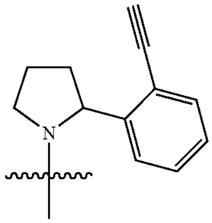;
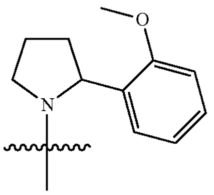,
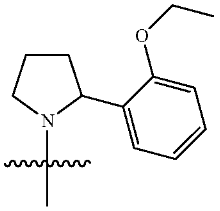,
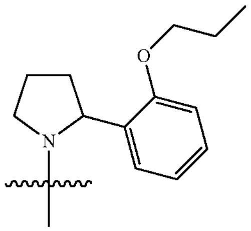, -continued
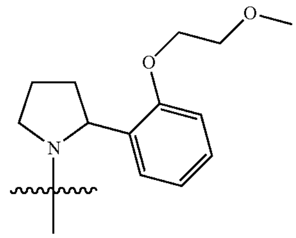
,
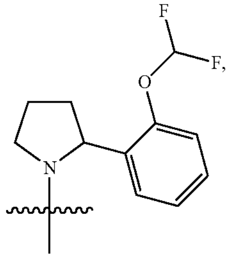
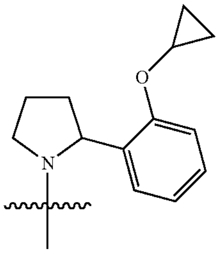
,
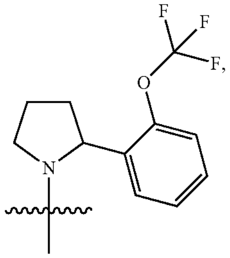
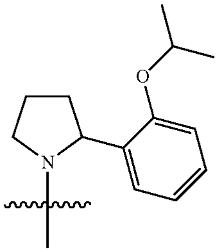
,
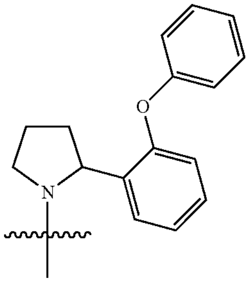
,
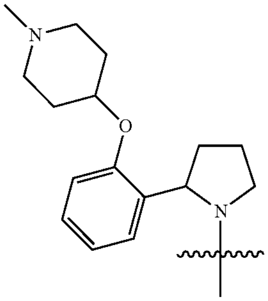
,
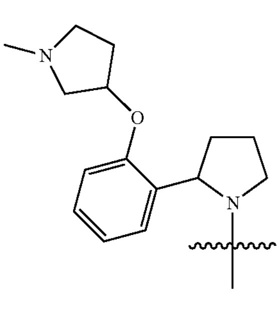
,
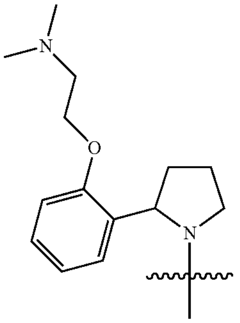
,
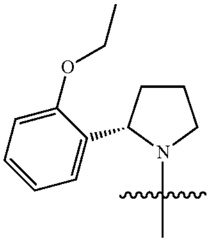
,
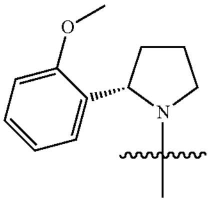
,
-continued
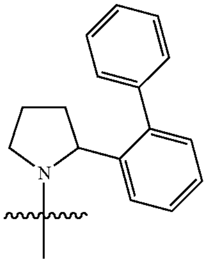
,
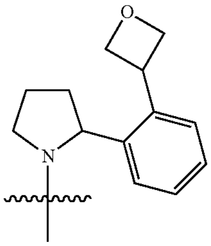
,
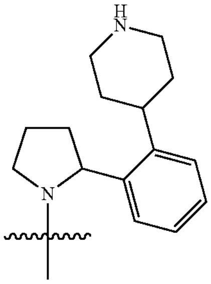
,
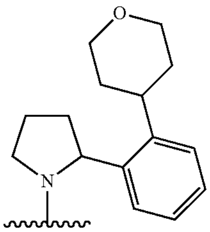
,
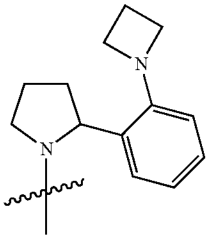
,
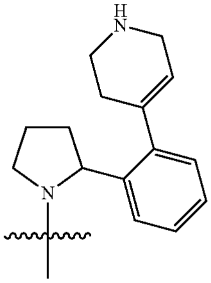
,
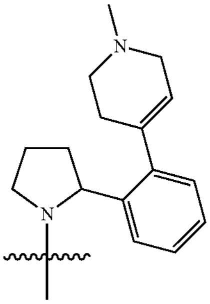
,
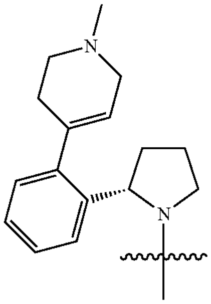
,
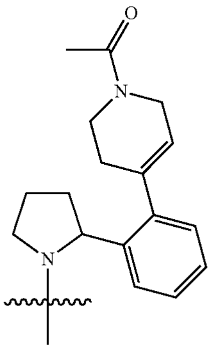
,
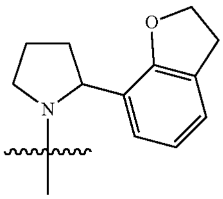
, -continued
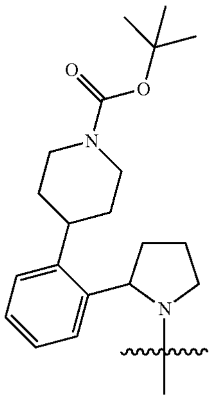
,
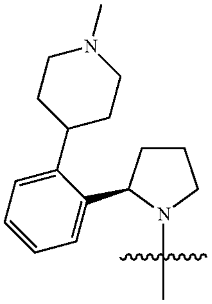
,
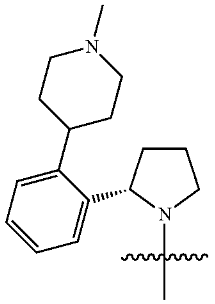
,
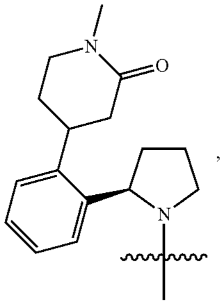
,
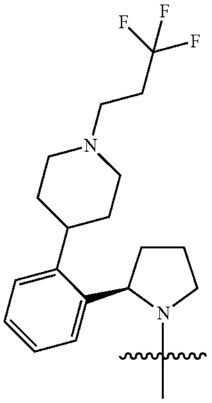
,
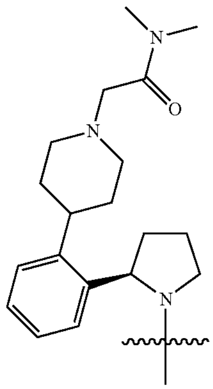
,
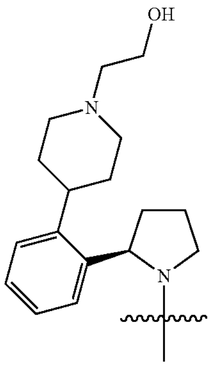
,
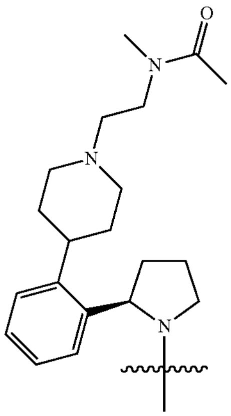
,
-continued
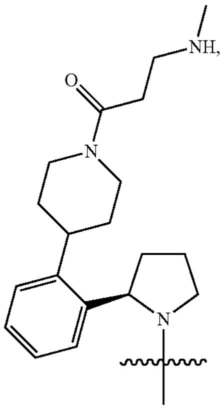
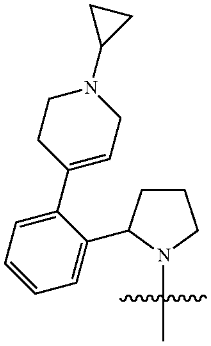
,
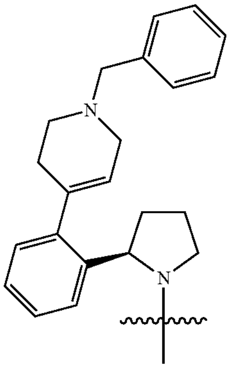
,
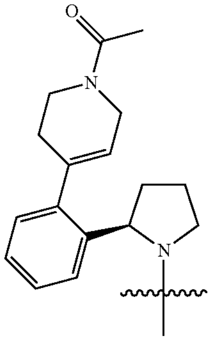
,
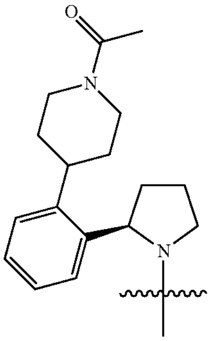
,
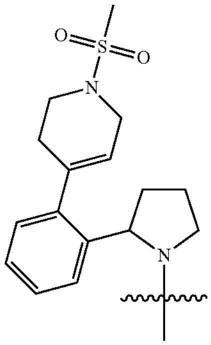
,
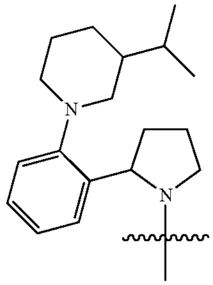
,
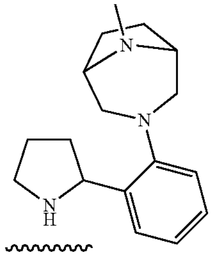
,
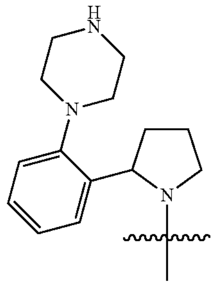
,
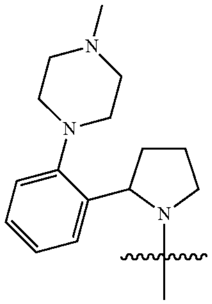
, -continued
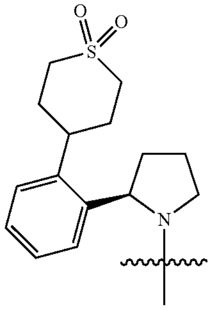,
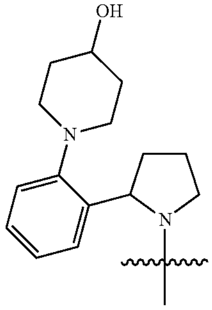,
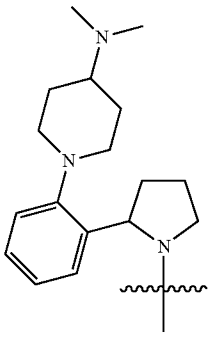,
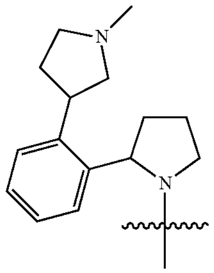,
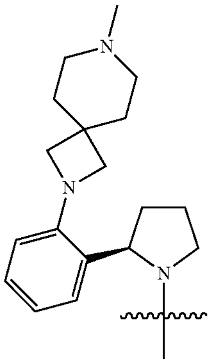,
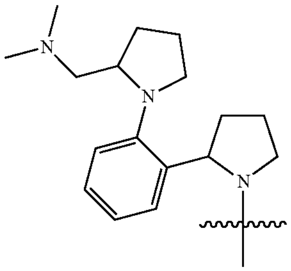,
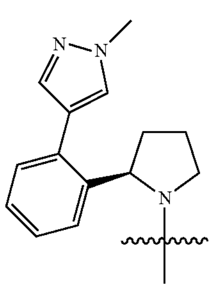,
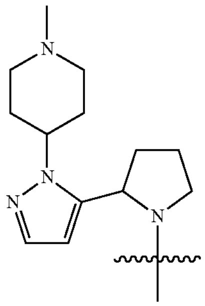,
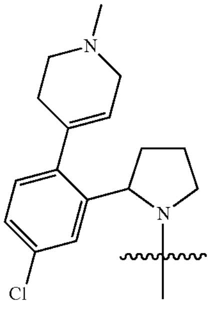,
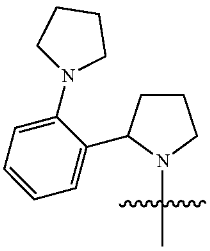;
-continued
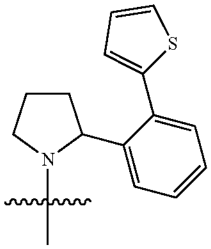,
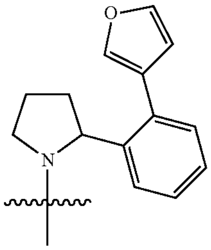,
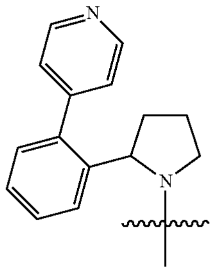;
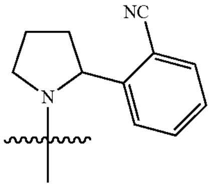;
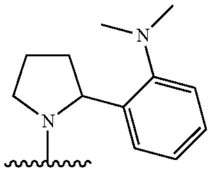,
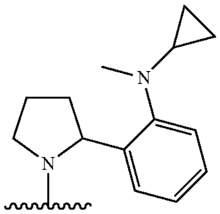,
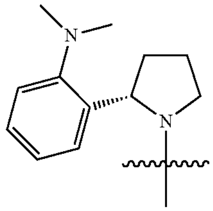,
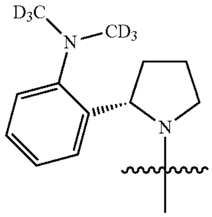,
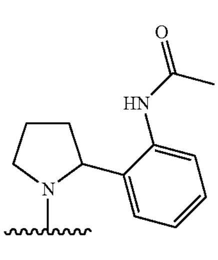,
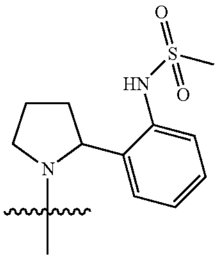,
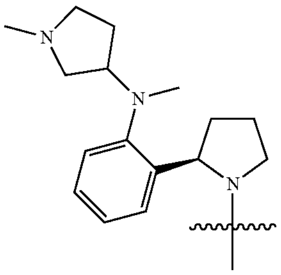,
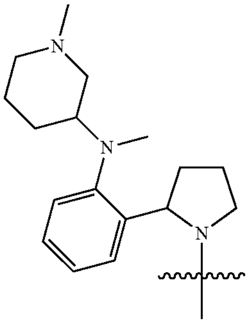, -continued

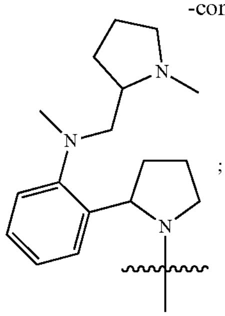
;
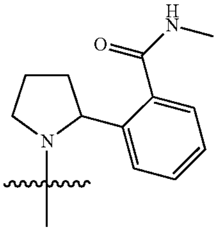
,

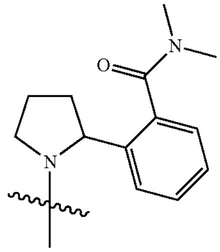
; and
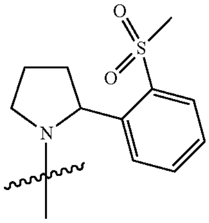
.

In one embodiment, $L^2$ is a direct bond, $—(CR^aR^b)_{1-4}—$, $—O—(CR^aR^b)_{1-3}—$, $—NH—(CR^aR^b)_{0-2}—(CR^aR^b)_{0-2}—$, $—(CR^aR^b)_{0-2}—(CR^aR^b)_{0-2}—NH—$, $—(CR^aR^b)_{0-2}—(NH)_{0-2}—C(O)—$, wherein $R^a$ and $R^b$ are hydrogen.

In one embodiment, CyC is cycloalkyl or heterocyclyl, each of which is optionally substituted with one or two substituents $R^{5a}$; wherein $R^{5a}$ is independently selected from hydrogen, halogen, cyano, oxo, $—OR^{5b}$, $—NR^{5b}R^{5c}$, $—COR^{5b}$, $—SO_2R^{5b}—$, $—C_{1-8}$alkyl, $—C_{2-8}$alkynyl, -cycloalkyl, or heterocyclyl, each of said $—C_{1-8}$alkyl, and heterocyclyl is optionally substituted with one or two substituents $R^{5e}$ which is selected from hydrogen, halogen, cyano, $—OR^{5f}$, $—C_{1-8}$alkyl, -cycloalkyl, or heterocyclyl; wherein $R^{5b}$, and $R^{5c}$ are each independently hydrogen, $—C_{1-8}$alkyl or heterocyclyl, said $—C_{1-8}$alkyl is optionally substituted with one or two substituents $R^{5e}$ which is hydrogen, $—NR^{5f}R^{5g}$, or -cycloalkyl; $R^{5f}$ and $R^{5g}$ are each independently hydrogen or $—C_{1-8}$alkyl.

In one embodiment, CyC is cyclopentyl or cyclohexyl, each of which is optionally substituted with one or two substituents $R^{5a}$.

In one embodiment, CyC is 6 membered-aryl or 6 membered-heteroaryl, each of which is optionally substituted with one or two substituents $R^{5a}$.

In a preferred embodiment, CyC is monocyclic 4 to 6-membered heterocyclyl groups containing one or two heteroatoms selected from nitrogen (N) or oxygen (O) or sulfur (S) heteroatom as ring member, each of which is optionally substituted with one or two substituents $R^{5a}$.

In a preferred embodiment, Cyc is selected from oxetanyl, tetrahydrofuranyl, tetrahydropyranyl, azetidinyl, pyrrolidinyl, piperdinyl, dioxanyl, morpholino, morpholinyl, or piperzinyl, each of which is optionally substituted with one or two substituents $R^{5a}$. In one embodiment, CyC is selected from oxetan-2-yl, oxetan-3-yl, tetrahydrofuran-4-yl, tetrahydrofuran-2-yl, tetrahydrofuran-3-yl, tetrahydropyran-2-yl, tetrahydropyran-3-yl, tetrahydropyran-4-yl, azetidin-3-yl, azetidin-2-yl, pyrrolidin-2-yl, pyrrolidin-3-yl, piperdin-4-yl, piperdin-2-yl, piperdin-3-yl, 1,3-dioxan-2-yl, 1,3-dioxan-4-yl, 1,4-dioxan-2-yl, morpholin-1-yl, morpholin-2-yl, ormorpholin-3-yl, each of which is optionally substituted with one or two substituents $R^{5a}$.

In a preferred embodiment, $R^{5a}$ is independently selected from hydrogen, halogen, cyano, oxo, $—OR^{5b}$, $—NR^{5b}R^{5c}$, $—COR^{5b}$, $—SO_2R^{5b}$, $—C_{1-8}$alkyl, $—C_{2-8}$alkynyl, monocyclic $C_{3-8}$cycloalkyl, or monocyclic 4 to 9-membered heterocyclyl group containing one or two heteroatoms selected from nitrogen or oxygen or sulfur heteroatom as ring members, each of said $—C_{1-8}$alkyl and monocyclic 4 to 9-membered heterocyclyl group is optionally substituted with one or two substituents $R^{5c}$.

In a preferred embodiment, m is 1 and $-L^2$-CyC is selected from the group consisting of:

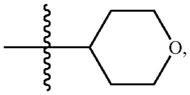
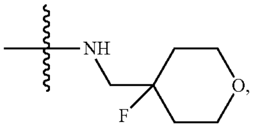
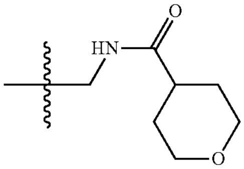
,
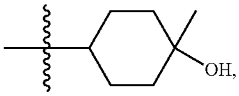
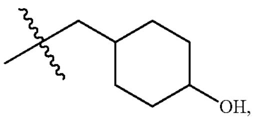
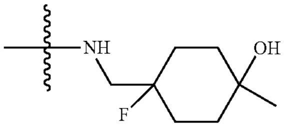
,
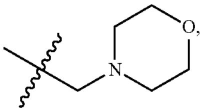
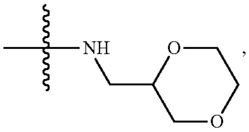
,
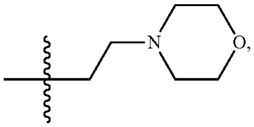
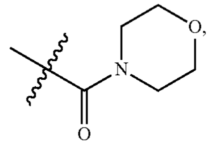
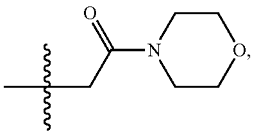
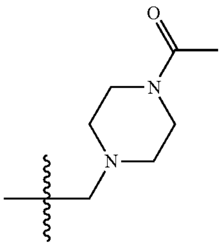
,
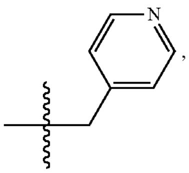
,
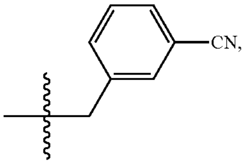
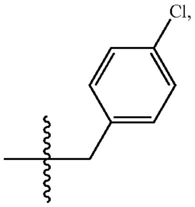
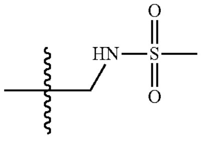
, -continued
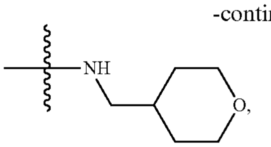
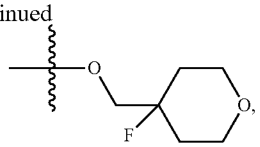
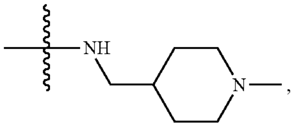
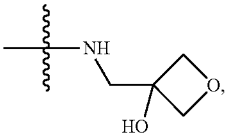
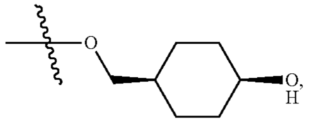
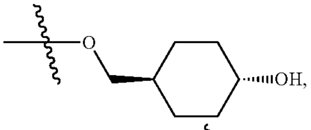
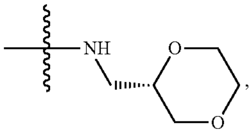
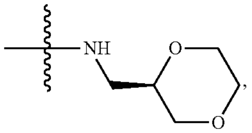
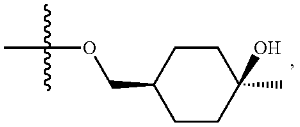
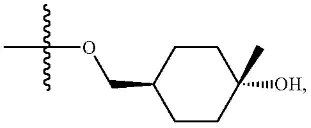
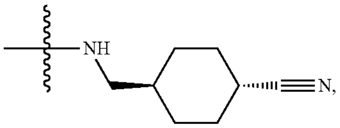
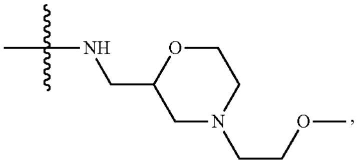
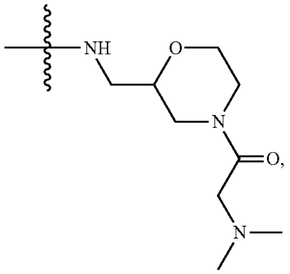
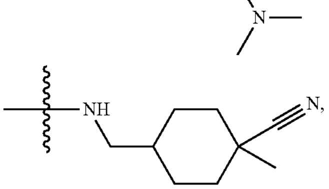
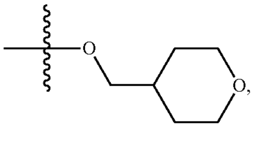
-continued
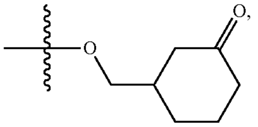
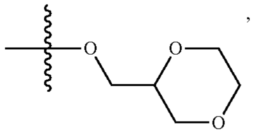
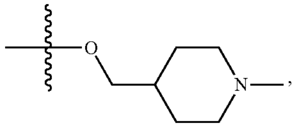
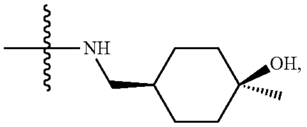
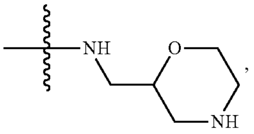
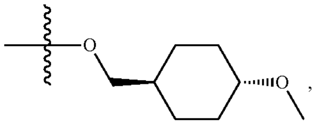
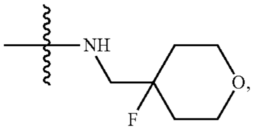
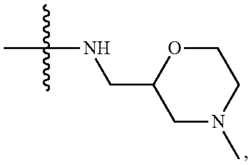
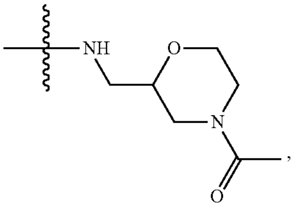
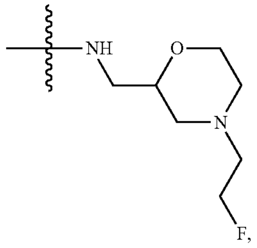
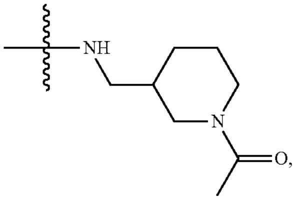
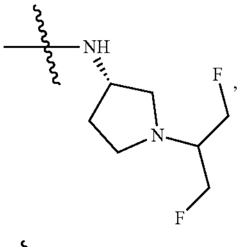
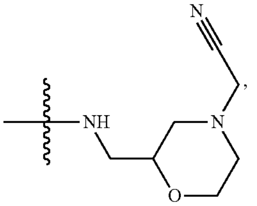
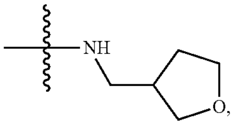
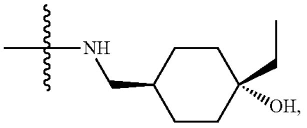
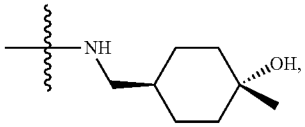
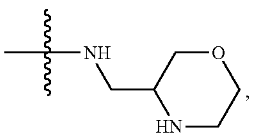

-continued

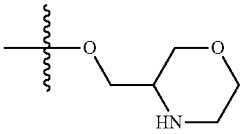

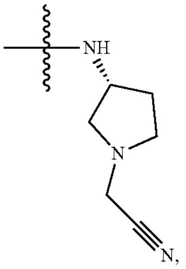

,

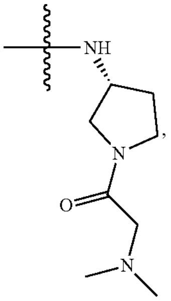

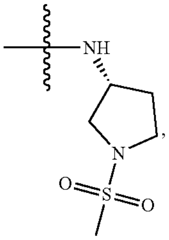

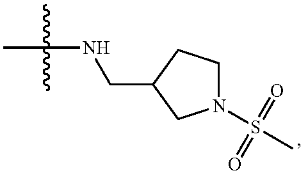

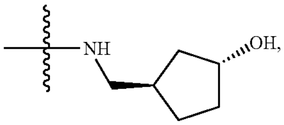

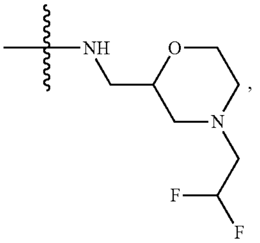

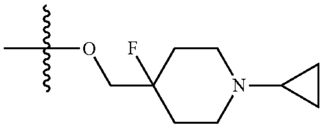

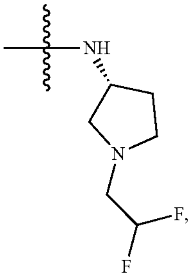

,

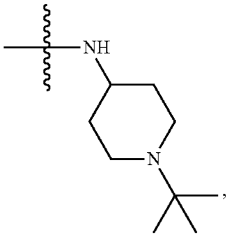

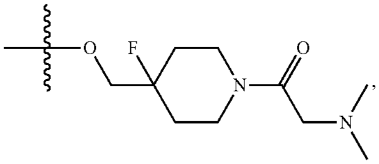

-continued

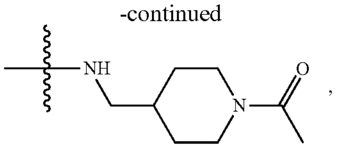

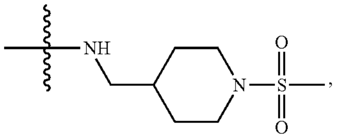

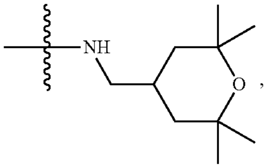

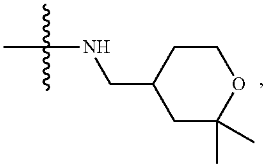

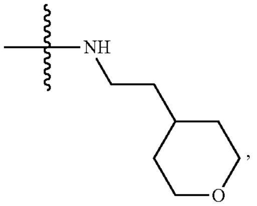

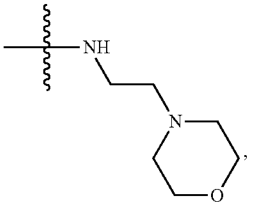

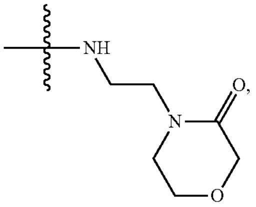

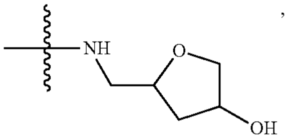

,

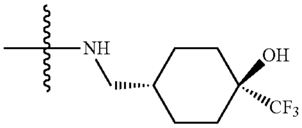

or

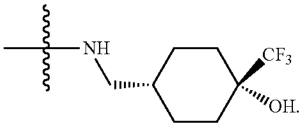

In a preferred embodiment, m is 1 and $-L^2$-CyC is selected from the group consisting of compounds of Examples A1, A2, A3, A4, A5, A6, A7, A8, B1, B2, B3, B4, B5, B6, B7, B8, B9, B10, B11, B12, B13, B14 and B15.

Disclosed herein is a method for treating dysregulated apoptotic diseases, comprising administering a subject in need thereof a therapeutically effective amount of the compound disclosed herein, or a pharmaceutically acceptable salt thereof, or a stereoisomer thereof. In one embodiment, the dysregulated apoptotic disease is cancer, such as, bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer published in WO2005049593A and WO2005049594A.

In one embodiment, the dysregulated apoptotic disease is autoimmune disease, such as, Systemic Lupus Erythematosus (SLE).

Disclosed herein a pharmaceutical composition comprising the compound disclosed herein, or a pharmaceutically acceptable salt thereof, or a stereoisomer thereof, and a pharmaceutically acceptable carrier.

DETAILED DESCRIPTION OF THE INVENTION

Definitions

The following terms have the indicated meanings throughout the specification:

As used herein, including the appended claims, the singular forms of words such as "a", "an", and "the", include their corresponding plural references unless the context clearly dictates otherwise.

The term "or" is used to mean, and is used interchangeably with, the term "and/or" unless the context clearly dictates otherwise.

The term "alkyl" refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups. The alkyl group can be optionally enriched in deuterium, e.g., $—CD_3$, $—CD_2CD_3$ and the like.

The term "halogen" refers to fluoro (F), chloro (Cl), bromo (Br) and iodo (I).

The term "alkenyl" refers to a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_2$ alkynyl, include, but not limited to ethynyl, 1-propynyl, 2-propynyl (propargyl), 1-butynyl, 2-butynyl, and 3-butynyl groups.

The term "cycloalkyl" refers to a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, cyclohexyl, cycloheptyl, cyclooctyl, cyclononyl, cyclodecyl, cycloundecyl, and cyclododecyl groups. In particular, examples of the saturated monocyclic cycloalkyl group, e.g., $C_{3-8}$ cycloalkyl, include, but not limited to cyclopropyl, cyclobutyl, cyclopentyl, cyclohexyl, cycloheptyl, and cyclooctyl groups. In a preferred embedment, the cycloalkyl is a monocyclic ring comprising 3 to 6 carbon atoms (abbreviated as C cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems, such as

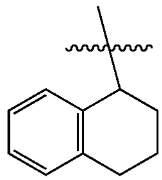

and

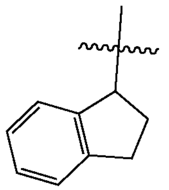

wherein the wavy lines indicate the points of attachment. The ring may be saturated or have at least one double bond (i.e. partially unsaturated), but is not fully conjugated, and is not aromatic, as aromatic is defined herein.

The term "spiro cycloalkyl" refers to a cyclic structure which contains carbon atoms and is formed by at least two rings sharing one atom. The term "7 to 10 membered spiro cycloalkyl" refers to a cyclic structure which contains 7 to 10 carbon atoms and is formed by at least two rings sharing one atom.

The term "fused cycloalkyl" refers to a fused ring which contains carbon atoms and is formed by two or more rings sharing two adjacent atoms. The term "4 to 10 membered fused cycloalkyl" refers to a fused ring which contains 4 to 10 ring carbon atoms and is formed by two or more rings sharing two adjacent atoms.

Examples include but are not limited to bicyclo[1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$cycloalkenyl, 2,3-dihydro-1H-indenyl, 1H-indenyl, 1,2,3,4-tetralyl, 1,4-dihydronaphthyl, etc. Preferred embodiments are 8 to 9 membered fused cyclyl, which refer to cyclic structures containing 8 to 9 ring atoms within the above examples.

The term "bridged cycloalkyl" refers to a cyclic structure which contains carbon atoms and is formed by two rings sharing two atoms which are not adjacent to each other. The term "7 to 10 membered bridged cycloalkyl" refers to a cyclic structure which contains 7 to 12 carbon atoms and is formed by two rings sharing two atoms which are not adjacent to each other.

The term "cycloalkenyl" refers to non-aromatic cyclic alkyl groups of from 3 to 10 carbon atoms having single or multiple rings and having at least one double bond and preferably from 1 to 2 double bonds. In one embodiment, the cycloalkenyl is cyclopentenyl or cyclohexenyl, preferably cyclohexenyl.

The term "cycloalkynyl" refers to non-aromatic cycloalkyl groups of from 5 to 10 carbon atoms having single or multiple rings and having at least one triple bond.

The term "aryl" used alone or in combination with other terms refers to a group selected from:

a) 5- and 6-membered carbocyclic aromatic rings, e.g., phenyl;

b) bicyclic ring systems such as 7 to 12 membered bicyclic ring systems, wherein at least one ring is carbocyclic and aromatic, e.g., naphthyl and indanyl; and, c) tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "heteroaryl" refers to a group selected from:

a) 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;

b) 8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and c) 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides. The term "C-linked heteroaryl" as used herein means that the heteroaryl group is connected to the core molecule by a bond from a C-atom of the heteroaryl ring The terms "aromatic heterocyclic ring" and "heteroaryl" are used interchangeable throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is a 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzofuranyl, benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

"Heterocyclyl", "heterocycle" or "heterocyclic" are interchangeable and refer to a non-aromatic heterocyclyl group comprising one or more heteroatoms selected from the group consisting of NH, O, S, SO or $SO_2$ heteroatoms as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "monocyclic heterocyclyl" refers to monocyclic groups in which at least one ring member is a heteroatom selected from the group consisting of NH, O, S, SO or $SO_2$. A heterocycle may be saturated or partially saturated.

Exemplary monocyclic 4 to 9-membered heterocyclyl groups include, but not limited to, (as numbered from the linkage position assigned priority 1) pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2,5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, or 1,1-dioxo-thiomorpholinyl.

The term “spiro heterocyclyl” or “heterospirocyclyl” refers to a 5 to 20-membered polycyclic heterocyclyl with rings connected through one common carbon atom (called a spiro atom), comprising one or more heteroatoms selected from the group consisting of NH, O, S, SO or $SO_2$ heteroatoms as ring members, with the remaining ring members being carbon. One or more rings of a spiro heterocyclyl group may contain one or more double bonds, but none of the rings has a completely conjugated pi-electron system. Preferably a spiro heterocyclyl is 6 to 14-membered, and more preferably 7 to 10-membered. According to the number of common spiro atoms, a spiro heterocyclyl is divided into mono-spiro heterocyclyl, di-spiro heterocyclyl, or poly-spiro heterocyclyl, and preferably refers to mono-spiro heterocyclyl or di-spiro heterocyclyl, and more preferably 4-membered/4-membered, 3-membered/5-membered, 4-membered/5-membered, 4-membered/6-membered, 5-membered/5-membered, or 5-membered/6-membered mono-spiro heterocyclyl. Representative examples of spiro heterocyclyls include, but not limited to the following groups: 2,3-dihydrospiro[indene-1,2'-pyrrolidine] (e.g., 2,3-dihydrospiro[indene-1,2'-pyrrolidine]-1'-yl), 1,3-dihydrospiro[indene-2,2'-pyrrolidine] (e.g., 1,3-dihydrospiro[indene-2,2'-pyrrolidine]-1'-yl), azaspiro[2.4]heptane (e.g., 5-azaspiro[2.4]heptane-5-yl), azaspiro[3.4]octane (e.g., 6-azaspiro[3.4]octane-6- yl), 2-oxa-6-azaspiro[3.4]octane (e.g., 2-oxa-6-azaspiro[3.4]octane-6-yl), azaspiro[3.4]octane (e.g., 6-azaspiro[3.4]octan-6-yl), azaspiro[3.4]octane (e.g., 6-azaspiro[3.4]octan-6-yl), 7-azaspiro[3,5]nonane (e.g., 7-azaspiro[3,5]nonan-7-yl), 2-azaspiro[3,5]nonane (e.g., 2-azaspiro[3,5]nonan-2-yl), 1,7-dioxaspiro[4.5]decane, 2-oxa-7-aza-spiro[4.4]nonane (e.g., 2-oxa-7-aza-spiro[4.4]non-7-yl), 7-oxa-spiro[3,5]nonyl and 5-oxa-spiro[2.4]heptyl.

The term “fused heterocyclic group” refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from the group consisting of NH, O, S, SO or $SO_2$ heteroatoms as ring members, with the remaining ring members being carbon. One or more rings of a fused heterocyclic group may contain one or more double bonds, but none of the rings has a completely conjugated pi-electron system. Preferably, a fused heterocyclyl is 6 to 14-membered, and more preferably 7 to 10-membered. According to the number of membered rings, a fused heterocyclyl is divided into bicyclic, tricyclic, tetracyclic, or polycyclic fused heterocyclyl, preferably refers to bicyclic or tricyclic fused heterocyclyl, and more preferably 5-membered/5-membered, or 5-membered/6-membered bicyclic fused heterocyclyl. Representative examples of fused heterocycles include, but not limited to, the following groups octahydrocyclopenta[c]pyrrole (e.g., octahydrocyclopenta[c]pyrrol-2-yl), octahydropyrrolo[3,4-c]pyrrolyl, octahydroisoindolyl, isoindolinyl (e.g., isoindoline-2-yl), octahydro-benzo[b][1,4]dioxin, dihydrobenzofuranyl, benzo[d][1,3]dioxolyl.

The term “bridged heterocyclyl” refers to a 5 to 14-membered polycyclic heterocyclic alkyl group, wherein every two rings in the system share two disconnected atoms, comprising one or more heteroatoms selected from the group consisting of NH, O, S, SO or $SO_2$ heteroatoms as ring members, with the remaining ring members being carbon. One or more rings of a bridged heterocyclyl group may contain one or more double bonds, but none of the rings has a completely conjugated pi-electron system. Preferably, a bridged heterocyclyl is 6 to 14-membered, and more preferably 7 to 10-membered. According to the number of membered rings, a bridged heterocyclyl is divided into bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include, but not limited to, the following groups: 2-azabicyclo[2.2.1]heptyl, azabicyclo[3.1.0]hexyl, 2-azabicyclo[2.2.2]octyl and 2-azabicyclo[3.3.2]decyl.

The heterocyclyl ring may be fused to aryl, heteroaryl or cycloalkyl ring, wherein the ring structure is connected to the parent heterocyclic group together.

“C-linked heterocyclyl” as used refers to a heterocyclyl group which is connected to the other part of the molecule by a direct bond from a carbon atom of the heterocyclyl ring.

“N-linked heterocyclyl” as used refers to a heterocyclyl group which is connected to the other part of the molecule by a direct bond from a nitrogen atom of the heterocyclyl ring.

Compounds disclosed herein may contain an asymmetric center and may thus exist as enantiomers. “Enantiomers” refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term “substantially pure” as used herein means that the target stereoisomer contains no more than 35%, such as no more than 30%, further such as no more than 25%, even further such as no more than 20%, by weight of any other stereoisomer(s). In some embodiments, the term “substantially pure” means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

When compounds disclosed herein contain a di-substituted cyclohexyl or cyclobutyl group, substituents found on cyclohexyl or cyclobutyl ring may adopt cis and trans formations. Cis formation means that both substituents are found on the upper side of the 2 substituent placements on the carbon, while trans would mean that they were on opposing sides.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New, York: John Wiley & Sons, Inc., 1994; Lochmuller, C. H., et al. "*Chromatographic resolution of enantiomers*: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer; Irving W, Ed. *Drug Stereochemistry*: *Analytical Methods and Pharmacology*. *New York*: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolying the free base in a suitable organic solyent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined above, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solyents, etc., a filler such as starch, sucrose, etc. a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "$C_{n-m}$" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless indicated otherwise.

Example A1: 2-((1H-pyrrolo[2,3-b]pyridin-5-yl)oxy)-4-(2-((S)-2-(2-isopropylphenyl)pyrrolidin-1-yl)-7-azaspiro[3,5]nonan-7-yl)-N-((5-nitro-3-(tetrahydro-2H-pyran-4-yl)-3,4-dihydro-2H-benzo[b][1,4]oxazin-7-yl)sulfonyl)benzamide

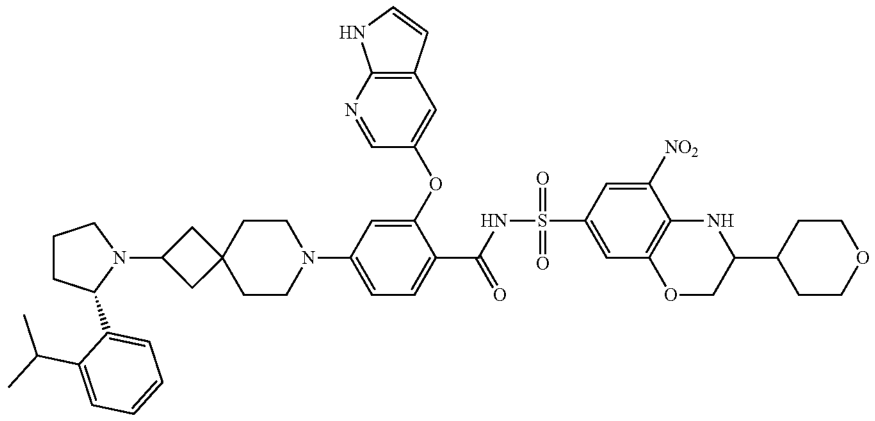 [SMILES: CC(C)c1ccccc1[C@@H]1CCCN1C1CC2(CCN(c3ccc(C(=O)NS(=O)(=O)c4cc5c(c([N+](=O)[O-])c4)NC(C4CCOCC4)CO5)c(Oc4cnc5[nH]ccc5c4)c3)CC2)C1]

A1-1: methyl 2-((1H-pyrrolo[2,3-b]pyridin-5-yl)oxy)-4-(2,2-dimethoxy-7-azaspiro[3,5]nonan-7-yl)benzoate

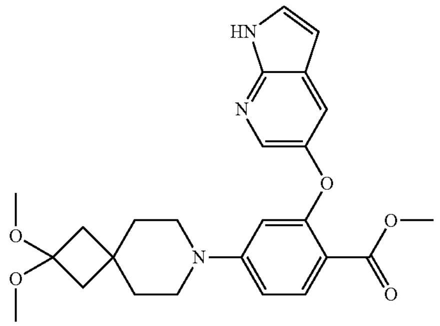 [SMILES: COC(=O)c1ccc(N2CCC3(CC2)CC(OC)(OC)C3)cc1Oc1cnc2[nH]ccc2c1]

Synthesis of 2,2-dimethoxy-7-azaspiro[3,5]nonane hydrochloride

To the solution of tert-butyl 2-oxo-7-azaspiro[3,5]nonane-7-carboxylate (500 g, 2.09 mol) in MeOH (750 mL) and EA (750 mL) was added conc. HCl acid (350 mL, 4.18 mol) at room temperature and stirred for 4 hours. After concentrated in vacuum, MeOH (750 mL) was added into the residue and then the resulting mixture was concentrated in vacuum (repeated this work-up twice). The brown residue was suspended in EA (1250 mL) and stirred for 1 hour. The solid precipitation was filtered and dried in vacuum to afford the tittle product as an off-white powder (350 g, yield: 76.0%). 1H NMR (400 MHz, DMSO-$d_6$) δ ppm: 3.03 (s, 6H), 2.96-2.89 (m, 4H), 1.93 (s, 4H), 1.74-1.67 (m, 4H). MS (ESI, m/e) $[M+1]^+$ 186.0.

Synthesis of methyl 2-((0H-pyrrolo[2,3-b]pyridin-5-yl)oxy)-4-(2,2-dimethoxy-7-azaspiro[3,5]nonan-7-yl)benzoate The mixture of methyl 2-((1H-pyrrolo[2,3-b]pyridin-5-yl)oxy)-4-fluorobenzoate (100 g), 2,2-dimethoxy-7-azaspiro[3,5]nonane hydrochloride (116 g) and DBU (160 g) in NMP (500 mL) was stirred for 16 hours at 85° C. After the reaction was completed, the mixture was cooled to 50±5'C and citric acid in water (2%, 5 L) was added drop-wise into the system under stirring. After filtered, the cake was collected and dissolyed with DCM (1.5 L). The solution of crude product was washed with citric acid in water (2%, 1.5 L), saturated aq. $NaHCO_3$ (1.5 L) and 15% aq. NaCl (1.5 L), and then dried over anhydrous $Na_2SO_4$. Silica gel (100 g) was added into the solution of crude product under stirring and then filtered. The filtrate was concentrated to 300 mL. MTBE (500 mL) was poured into the system. After stirred for 2 hours, the cake was collected after filtration and was dried in vacuum to give an off-white solid (192 g, yield: 72.1%). $^1$H NMR (400 MHz, DMSO-$d_6$) δ ppm: 11.63 (s, 11H), 8.00 (d, J=2.4 Hz, 1H), 7.76 (d, J=9.2 Hz, 11H), 7.47 (t, J=3.2 Hz, 1H), 7.42 (d, J=2.4 Hz, 1H), 6.79 (dd, J=2.4 Hz, J=9.2 Hz, 1H), 6.39-6.36 (m, 2H), 3.64 (s, 3H), 3.17-3.12 (m, 4H), 3.01 (s, 6H), 1.86 (s, 4H), 1.54-1.50 (m, 4H). MS (ESI, m/e) $[M+1]^+$ 451.9.

A1-2: methyl 2-((1H-pyrrolo[2,3-b]pyridin-5-yl)oxy)-4-(2-oxo-7-azaspiro[3,5]nonan-7-yl)benzoate

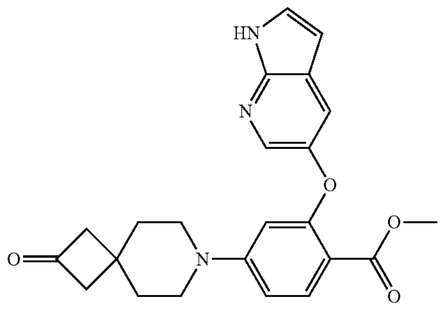 [SMILES: COC(=O)c1ccc(N2CCC3(CC2)CC(=O)C3)cc1Oc1cnc2[nH]ccc2c1]

To the solution of methyl 2-((1H-pyrrolo[2,3-b]pyridin-5-yl)oxy)-4-(2,2-dimethoxy-7-azaspiro[3,5]nonan-7-yl)benzoate (176 g, 0.39 mol) in DCM (2 L) was added diluted HCl acid (1M, 1.5 L) and stirred for overnight. After the reaction was completed, the mixture was cooled to 10° C. and was adjusted to pH=8-9 with aqueous NaOH solution (4 M) under stirring. The organic phase was separated and washed with 15% aq. NaCl (1 L), then washed with $H_2O$ (1 L). After the organic phase was concentrated to 500 mL, MTBE (1 L) was poured into the solution and then the system was concentrated to 500 mL (repeated this work-up 3 times). The resulting system was stirred for 0.5 hour. After filtration, the cake was collected and then dried in vacuum to obtain the tittle product as a white solid (152 g, yield: 96.2%). $^1$H NMR (400 MHz, DMSO-$d_6$) δ ppm: 11.64 (s, 1H), 8.02 (d, J=2.4 Hz, 1H), 7.78 (d, J=9.2 Hz, 1H), 7.47 (t, J=3.2 Hz, 1H), 7.44 (d, J=2.4 Hz, 1H), 6.83 (dd, J=2.4 Hz. J=9.2 Hz, 1H), 6.43 (d, J=2.4 Hz, 1H), 6.38-6.36 (m, 1H), 3.65 (s, 3H), 3.24-3.21 (m, 4H), 2.80 (s, 4H), 1.70-1.67 (m, 4H). MS (ESI, m/e) $[M+1]^+$ 405.9.

A1-3: (S)-2-(2-isopropylphenyl)pyrrolidine hydrochloride

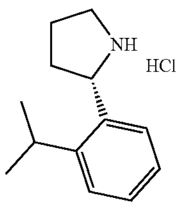

Synthesis of (S)-tert-butyl 2-(2-(prop-1-en-2-yl)phenylpyrrolidine-1-carboxylate To a mixture of (S)-tert-butyl 2-(2-bromophenyl)pyrrolidine-1-carboxylate (50 g, 153.3 mmol) and 4,4,5,5-tetramethyl-2-(prop-1-en-2-yl)-1,3,2-dioxaborolane (38.6 g, 229.9 mmol) in dioxane (500 mL) and $H_2O$ (50 mL) was added $Cs_2CO$ (100 g, 305 mmol) and Pd(dppf)$Cl_2$ (6.6 g, 7.5 mmol). The mixture was stirred at 100° C. for 8 hours. TLC showed the reaction was completed. The mixture was concentrated in vacuum. The residue was purified by column chromatography on silica gel (eluent: PE:EA=100:1 to 10:1) to obtain (S)-tert-butyl 2-(2-(prop-1-en-2-yl)phenyl)pyrrolidine-1-carboxylate (65 g, crude). The crude product was used directly in next step.

Synthesis of (S)-tert-butyl 2-(2-isopropylphenyl)pyrrolidine-1-carboxylate

To a solution of (S)-tert-butyl 2-(2-(prop-1-en-2-yl)phenyl)pyrrolidine-1-carboxylate (30 g, 104.39 mmol) in MeOH (500 mL) was added Pd/C (10 g, 10%) and the mixture was stirred at 20° C. under $H_2$ (15 Psi) for 12 hours. TLC showed the reaction was completed. The mixture was filtered and the filtrate was concentrated in vacuum to give (S)-tert-butyl 2-(2-isopropylphenyl)pyrrolidine-1-carboxylate (60 g, crude), which was used in next step without further purification. $^1$H NMR (400 MHz, $CDCl_3$) δ ppm: 7.39-6.90 (m, 4H), 5.36-5.04 (m, 1H), 3.77-3.52 (m, 2H), 3.20-3.17 (m, 1H), 2.47-2.24 (m, 1H), 1.96-1.65 (m, 3H), 1.54-1.38 (m, 2H), 1.31-1.22 (m, 8H), 1.17 (s, 7H).

Synthesis of (S)-2-(2-isopropylphenylipyrrolidine hydrochloride

To a solution of tert-butyl 2-(2-isopropylphenyl)pyrrolidine-1-carboxylate (55 g, 190 mmol) in DCM (50 mL) was added HCl in 1,4-dioxane (4 M, 142 mL, 570 mmol) dropwise at room temperature. The mixture was stirred at room temperature for overnight. The mixture was concentrated in vacuum. The resulting residue was slurried with EA (100 mL) and then filtered, dried in vacuum to give (S)-2-(2-isopropylphenyl)pyrrolidine hydrochloride 26 g (yield: 60.4%). $^1$H NMR (400 MHz, DMSO-$d_6$) δ ppm: 9.93 (s, 1H), 8.81 (s, 1H), 7.63-7.57 (m, 1H), 7.41-7.34 (m, 2H), 7.32-7.24 (m, 1H), 4.91-4.75 (m, 1H), 3.47-3.35 (m, 1H), 3.31-3.25 (m, 1H), 2.40-2.21 (m, 1H), 2.19-1.86 (m, 3H), 1.25 (d, J=6.7 Hz, 3H), 1.17 (d, J=6.7 Hz, 3H). MS (ESI, m/e) $[M+1]^+$ 190.0.

A1-4: methyl (S)-2-((1H-pyrrolo[2,3-b]pyridin-5-yl)oxy)-4-(2-(2-(2-isopropylphenyl)pyrrolidin-1-yl)-7-azaspiro[3,5]nonan-7-yl)benzoate

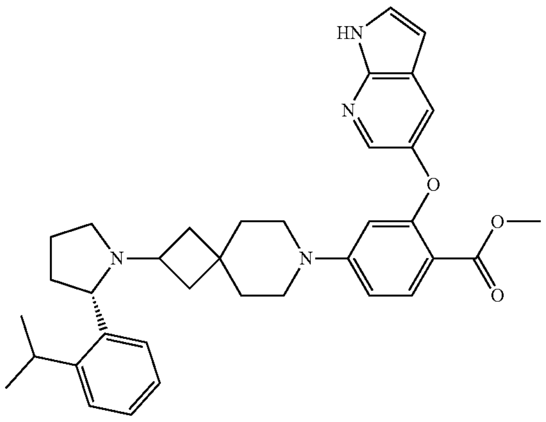 [SMILES: COC(=O)c1ccc(N2CCC3(CC2)CC(N2CCC[C@H]2c2ccccc2C(C)C)C3)cc1Oc1cnc2[nH]ccc2c1]

A mixture of (S)-2-(2-isopropylphenyl)pyrrolidine hydrochloride (120 g, 0.535 mole) and methyl 2-((1H-pyrrolo[2,3-b]pyridin-5-yl)oxy)-4-(2-oxo-7-azaspiro[3,5]nonan-7-yl)benzoate (218 g, 0.509 mole) in DCM (2.2 L) was charged into a reactor. The temperature was controlled blow 30° C. and $NaBH(OAc)_3$ (216 g, 1.018 mole) was added into the reactor in 5-6 portions. Then the reaction mixture was stirred at room temperature and monitored by TLC. After the starting material ketone was consumed completely, the mixture was adjusted to pH=4-5 with diluted HCl acid (0.5 M). The separated organic phase was washed with $H_2O$ (600 mL×2) and then washed with aq. $NaHCO_3$ (600 mL×2), saturated aq. NaCl (600 mL). The organic phase was collected, then dried over anhydrous $Na_2SO_4$ and concentrated. 256 g off-white solid was obtained as crude product, which was used in next step directly. MS (ESI, m/e) $[M+1]^+$ 579.0.

A1-5: (S)-2-((1H-pyrrolo[2,3-b]pyridin-5-yloxy)-4-(2-(2-(2-isopropylphenyl)pyrrolidin-1-yl-7-azaspiro[3,5]nonan-7-yl)benzoic acid

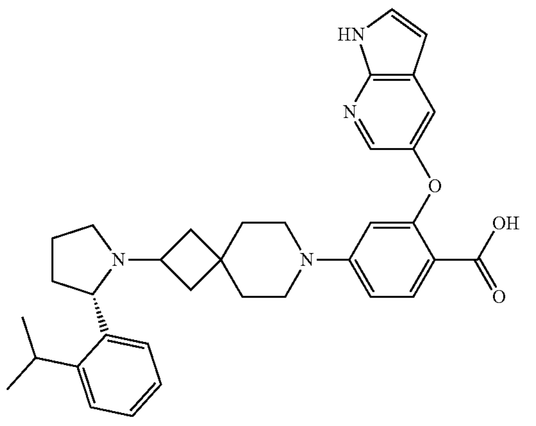 [SMILES: CC(C)c1ccccc1[C@@H]1CCCN1C1CC2(CCN(c3ccc(C(=O)O)c(Oc4cnc5[nH]ccc5c4)c3)CC2)C1]

To a solution of methyl (S)-2-((1H-pyrrolo[2,3-b]pyridin-5-yl)oxy)-4-(2-(2-(2-isopropylphenyl)pyrrolidin-1-yl)-7-azaspiro[3,5]nonan-7-yl)benzoate (105 g, 181.7 mmol) in THF (525 mL) and MeOH (525 mL) was added aq. NaOH (3.5 M). It was stirred at room temperature overnight. After THF and MeOH were removed in vacuum, 3.5 L of water was added into the residue. The resulting mixture was adjusted to pH=5-6 with 3 N HCl acid at room temperature with stirring. The precipitate was filtered and dried in vacuum to give the product as a white solid (102.4 g, yield: 99%). 1H NMR (400 MHz, DMSO-d) δ ppm: 12.13 (s, 1H), 11.58 (s, 1H), 7.95 (s, 1H), 7.67 (d, J=8.0 Hz, 1H), 7.56-7.40 (m, 2H), 7.35 (s, 1H), 7.27-7.04 (m, 3H), 6.68 (d, J=8.0 Hz, 1H), 6.32 (s, 2H), 3.62 (s, 1H), 3.32-3.26 (m, 1H), 3.10-3.04 (m, 4H), 2.35-2.30 (m, 1H), 2.9-2.15 (m, 1H), 1.74-1.64 (m, 4H), 1.52-1.37 (m, 6H), 1.28-1.06 (m, 6H). MS (ESI, m/e) $[M+1]^+$ 564.9.

A1-6: 5-nitro-3-(tetrahydro-2H-pyran-4-yl)-3,4-dihydro-2H-benzo[b][1,4]oxazine-7-sulfonamide

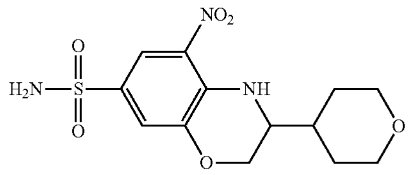 [SMILES: NS(=O)(=O)c1cc2c(c([N+](=O)[O-])c1)NC(C1CCOCC1)CO2]

Synthesis of methyl 2-(((benzyloxy)carbonyl)amino)-2-(dihydro-2H-pyran-4(3H)-ylidene)acetate To a solution of dihydro-2H-pyran-4(3H)-one (6.8 g, 0.07 mol) in $CH_3CN$ (100 mL) were added methyl 2-(((benzyloxy)carbonyl)amino)-2-(dimethoxyphosphoryl)acetate (22.5 g, 0.07 mol) and DBU (10.7 g, 0.07 mol). The mixture was stirred at 20'C for 12 hrs. The reaction mixture was poured into water (100 mL) and then extracted with EtOAc (2×50 mL). The organic layer was dried, filtered and concentrated under reduced pressure to give methyl 2-(((benzyloxy)carbonyl)amino)-2-(dihydro-2H-pyran-4(3H)-ylidene)acetate (20.0 g, 93.5% yield) as a solid. $^1H$ NMR (400 MHz, $CDCl_3$) δ ppm: 7.37 (br, 5H), 6.08 (br, 1H), 5.14 (s, 2H), 3.67-3.83 (m, 7H), 2.93 (br, 2H), 2.42 (t, J=5.4 Hz, 2H).

Synthesis of methyl 2-amino-2-(tetrahydro-2H-pyran-4-yl)acetate

To a solution of methyl 2-(((benzyloxy)carbonyl)amino)-2-(dihydro-2H-pyran-4(3H)-ylidene)acetate (20 g, 66.03 mmol) in THF (100 mL) was added Pd/C (5 g). The mixture was stirred at 45 V for 12 hrs under $H_2$ (50 psi) atmosphere. After filtration, the filtrate was concentrated under reduced pressure to give methyl 2-amino-2-(tetrahydro-2H-pyran-4-yl)acetate (4.3 g) as a brown oil, which was used into the next step without further purification.

Synthesis of 2-amino-2-(tetrahydro-2H-pyran-4-yl)ethanol

To a solution of methyl 2-amino-2-(tetrahydro-2H-pyran-4-yl)acetate (4.3 g, 25 mmol) in THF (50 mL) was added $LiAlH_4$ (1.4 g, 37 mmol) in several portions at 0° C. The mixture was stirred at 25° C. for 3 hrs. The reaction mixture was quenched by addition of aq. NaOH (2 mL, 2M) and dried over $Na_2SO_4$, filtered and the filtrate was concentrated under reduced pressure to give 2-amino-2-(tetrahydro-2H-pyran-4-yl)ethanol (2.0 g) as a brown oil, which was used for the next step without further purification.

Synthesis of 3-bromo-4-((2-hydroxy-1-(tetrahydro-2H-pyran-4-yl)ethyl)amino)-5-nitrobenzenesulfonamide To a solution of 3-bromo-4-chloro-5-nitrobenzenesulfonamide (1.3 g, 4.12 mmol) and 2-amino-2-(tetrahydro-2H-pyran-4-yl)ethanol (1.2 g, 8.24 mmol) in DMF (20 mL) was added DIEA (1.06 g, 8.24 mmol). The mixture was stirred at 60° C. for 12 hrs. The reaction mixture was diluted with $H_2O$ (50 mL) and then extracted with EtOAc (2'x50 mL). The organic layer was washed with brine, dried over anhydrous $Na_2SO_4$, filtered and concentrated. The residue was purified by column chromatography on silica gel (eluent PE:EA=5:1) to give 3-bromo-4-((2-hydroxy-1-(tetrahydro-2H-pyran-4- yl)ethyl)amino)-5-nitrobenzenesulfonamide (1.0 g, 57% yield) as a solid. $^1$H NMR (400 MHz, $CDCl_3$) δ ppm: 8.26 (d, J=1.88 Hz, 1H), 8.14 (d, J=1.8 Hz, 1H), 7.50 (s, 2H), 6.73 (br d, J=8.6 Hz, 1H), 4.93 (t, J=4.8 Hz, 1H), 3.79-3.91 (m, 2H), 3.67 (br s, 1H), 3.42-3.58 (m, 2H), 3.18-3.30 (m, 2H), 1.79-1.95 (m, 1H), 1.48-1.66 (m, 2H), 1.19-1.41 (m, 2H).

Synthesis of 5-nitro-3-(tetrahydro-2H-pyran-4-yl-3,4-dihydro-2H-benzo[b][1,4]oxazine-7-sulfonamide To a solution of 3-bromo-4-((2-hydroxy-1-(tetrahydro-2H-pyran-4-yl)ethyl)amino)-5-nitrobenzenesulfonamide (1 g, 2.36 mmol) in 1,2-dioxane (20 ML) was added $Pd_2(dba)_3$ (0.32 g, 0.354 mmol), Xantphos (0.34 g, 0.59 mmol) and $Cs_2CO_3$ (1.54 g, 4.72 mmol, 2 eq). The mixture was stirred at 100° C. for 10 hrs under Argon atmosphere. LC-MS showed reactant was consumed completely and one main peak with desired mass signal. After cooled to room temperature, the mixture was filtered. The filtrate was concentrated. The residue was purified by column chromatography on silica gel (eluent: PE:EA=5:1) to give 5-nitro-3-(tetrahydro-2H-pyran-4-yl)-3,4-dihydro-2H-benzo[b][1,4]oxazine-7- sulfonamide (410 mg, 50% yield) as a solid. $^1$H NMR (400 MHz, DMSO-$d_6$) δ ppm: 8.82 (d, J=4.0 Hz, 1H), 8.09 (d, J=2.0 Hz, 1H), 7.32 (s, 3H), 4.40 (dd, J=1.8, 11.26 Hz, 1H), 4.03-4.12 (m, 1H), 3.87 (dd, J=3.1, 11.1 Hz, 2H), 3.49-3.59 (m, 1H), 3.17-3.29 (m, 2H), 1.72-1.87 (m, 1H), 1.52-1.71 (m, 2H), 1.22-1.50 (m, 2H). MS (ESI, m/e) $[M+1]^+$ 344.3.

2-((1H-pyrrolo[2,3-b]pyridin-5-yl)oxy)-4-(2-((S)-2-(2-isopropylphenyl)pyrrolidin-1-yl)-7-azaspiro[3,5]nonan-7-yl-N-((5-nitro-3-(tetrahydro-2H-pyran-4-yl)-3,4-dihydro-2H-benzo[b][1,4]oxazin-7-yl)sulfonyl)benzamide A mixture of (S)-2-((1H-pyrrolo[2,3-b]pyridin-5-yl)oxy)-4-(2-(2-(2-isopropylphenyl)pyrrolidin-1-yl)-7-azaspiro[3,5]nonan-7-yl)benzoic acid (282 mg, 0.5 mmol), 5-nitro-3-(tetrahydro-2H-pyran-4-yl)-3,4-dihydro-2H-benzo[b][1,4]oxazine-7- sulfonamide (172 mg, 0.5 mmol), EDCI (124 mg, 0.65 mmol), TEA (0.1 mL) and DMAP (122 mg, 1 mmol) in DCM (25 mL) was stirred overnight at room temperature. The reaction mixture was quenched with 10% HOAc (20 mL) and washed with saturated aq. $NaHCO_3$ (10 mLx2), brine (10 mL), then dried over anhydrous $Na_2SO_4$, concentrated in vacuum. The residue was purified by prep-HPLC to give the desired compound 101 mg (yield: 23%). $^1$H NMR (400 MHz, DMSO-$d_6$): 11.61 (s, 1H), 11.25 (s, 1H), 8.76 (s, 1H), 8.14 (s, 1H), 7.99 (s, 1H), 7.59-7.38 (m, 4H), 7.34-7.01 (m, 4H), 6.65 (d, J=7.4 Hz, 1H), 6.35 (s, 1H), 6.17 (s, 1H), 4.31 (d, J=9.2 Hz, 1H), 4.01 (d, J=8.6 Hz, 1H), 3.86 (d, J=7.7 Hz, 2H), 3.50 (s, 1H), 3.29-3.11 (m, 4H), 3.01-2.92 (m, 5H), 2.25-2.21 (m, 1H), 1.80-1.71 (m, 5H), 1.65-1.25 (m, 12H), 1.25-1.03 (m, 7H). MS (ESI, m/e) $[M+1]^+$ 889.9.

Example A2: 2-((1H-pyrrolo[2,3-b]pyridin-5-yl)oxy)-N—(((R)-3-((1S,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3,5]nonan-7-yl)benzamide

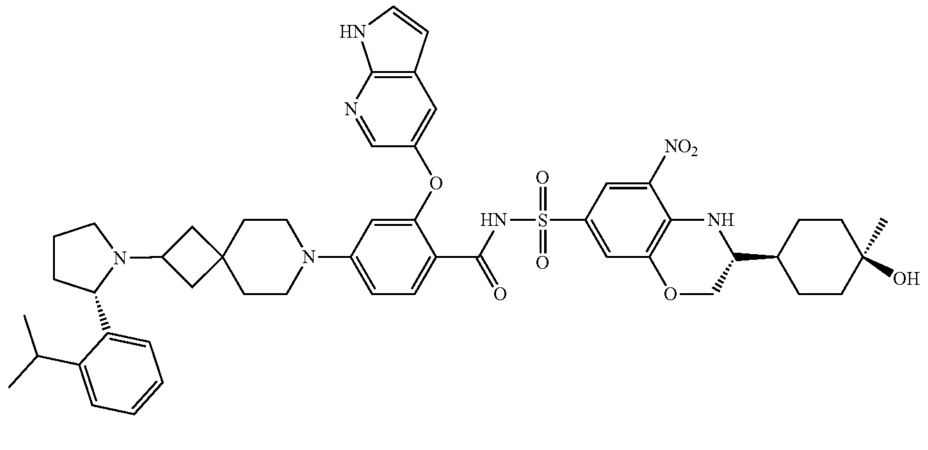 [SMILES: CC(C)c1ccccc1[C@@H]1CCCN1C1CC2(CCN(c3ccc(C(=O)NS(=O)(=O)c4cc5c(c([N+](=O)[O-])c4)N[C@H]([C@H]4CC[C@@](C)(O)CC4)CO5)c(Oc4cnc5[nH]ccc5c4)c3)CC2)C1]

A2-1a: (R)-3-((1S,4S)-4-hydroxy-4-methylcyclohexyl-5-nitro-3,4-dihydro-2H-benzo[b][1,4]oxazine-7-sulfonamide

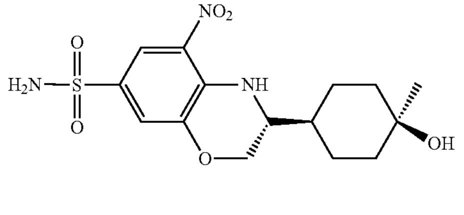 [SMILES: C[C@]1(O)CC[C@@H]([C@@H]2COc3cc(S(N)(=O)=O)cc([N+](=O)[O-])c3N2)CC1]

Synthesis of (R)-methyl 2-((tert-butoxycarbonyl) amino)-2-(4-hydroxyphenylacetate To a solution of (R)-methyl 2-amino-2-(4-hydroxyphenyl)acetate hydrochloride (25 g, 114.86 mmol) in dioxane (250 mL) was added $Boc_2O$ (27.58 g, 126.35 mmol) and $K_2CO_3$ (39.69 g, 287.15 mmol). The mixture was stirred at 20'C for 18 hrs. TLC showed the reaction was complete. The reaction mixture was poured into water (300 mL) and extracted with ethyl acetate (300 mL×3). The combined organic phase was washed with brine (100 mL×2), dried with anhydrous $Na_2SO_4$, filtered and concentrated in vacuum. The residue was purified by column chromatography on silica gel (eluent: PE:EA=100:1 to 5:1). (R)-methyl 2-((tert-butoxycarbonyl)amino)-2-(4-hydroxyphenyl)acetate (14.7 g, 45.5% yield) was obtained as solid. $^1H$ NMR (400 MHz, DMSO-$d_6$) δ ppm: 9.47 (s, 1H), 7.58 (d, J=7.5 Hz, 1H), 7.16 (d, J=8.5 Hz, 2H), 6.71 (d, J=8.5 Hz, 2H), 5.05 (d, J=7.8 Hz, 1H), 3.59 (s, 3H), 1.38 (s, 9H).

Synthesis of tert-butyl (R)-(2-hydroxy-1-(4-hydroxy)phenyl)ethyl)carbamate

To a solution of (R)-methyl 2-((tert-butoxycarbonyl) amino)-2-(4-hydroxyphenyl)acetate (14.7 g, 52.26 mmol) in THF (50 mL) was added $LiBH_4$ (2.28 g, 104.51 mmol) at 0° C. After addition, the mixture was stirred at 50° C. for 12 hours. TLC indicated reactant was consumed completely. The reaction mixture was quenched by saturated $NH_4Cl$ aqueous solution (100 mL), and then extracted with EA (100 mL×3) and washed with brine. The combined organic layers were dried over $Na_2SO_4$, filtered and concentrated under reduced pressure. The residue was purified by column chromatography on silica gel (eluent: PE:EA=100:1 to 20:1). (R)-tert-butyl (2-hydroxy-1-(4-hydroxyphenyl)ethyl) carbamate (12.9 g, 97.4% yield) was obtained as solid. $^1H$ NMR (400 MHz, DMSO-$d_6$) δ ppm: 9.22 (s, 1H), 7.06 (d, J=8.5 Hz, 3H), 6.67 (d, J=8.5 Hz, 2H), 4.69 (t, J=5.7 Hz, 1H), 4.32-4.47 (m, 1H), 3.36-3.47 (m, 2H), 1.36 (s, 9H).

Synthesis of tert-butyl (R)-4-(4-hydroxyphenyl-2,2-dimethyloxazolidine-3-carboxylate To a solution of (R)-tert-butyl (2-hydroxy-1-(4-hydroxyphenyl)ethyl)carbamate (13 g, 51.32 mmol) in DCM (500 mL) was added 2,2-dimethoxypropane (107 g, 102.6 mmol) and TsOH (1.95 g, 10.26 mmol). The mixture was stirred at 25° C. for 3 hours. TLC indicated reactant was consumed completely. The reaction mixture was concentrated under reduced pressure to remove solyent. The residue was purified by column chromatography on silica gel (eluent: PE:EA=100:1 to 2:1). (R)-tert-butyl 4-(4-hydroxyphenyl)-2,2-dimethyloxazolidine-3-carboxylate (10 g, 66.7% yield) was obtained. $^1H$ NMR (400 MHz, DMSO-$d_6$) δ ppm: 9.28 (s, 1H), 7.07 (d, J=8.0 Hz, 2H), 6.71 (d, J=8.0 Hz, 2H), 4.53-4.84 (m, 1H), 4.20 (dd, J=6.8, 8.6 Hz, 1H), 3.65-3.73 (m, 1H), 1.62 (br, 3H), 1.48 (br, 3H), 1.39 (br, 3H), 1.10-1.20 (m, 6H).

Synthesis of tert-butyl (R)-4-(4-hydroxycyclohexyl)-2,2-dimethyloxazolidine-3-carboxylate To a solution of (R)-tert-butyl 4-(4-hydroxyphenyl)-2,2-dimethyloxazolidine-3-carboxylate (10 g, 0.034 mol) in i-PrOH (300 mL) was added $PtO_2$ (2 g) and HOAc (61 g, 1.023 mol). The mixture was stirred at 50° C. for 12 hours under $H_2$ (50 psi) atmosphere. TLC indicated reactant was consumed completely. After the reaction mixture was filtered, the filtrate was concentrated under reduced pressure to give methyl 2-amino-2-(tetrahydro-2H-pyran-4-yl)acetate (10 g), which was used into the next step without further purification. MS (ESI, m/e) $[M+1]^+$ 300.3.

Synthesis of tert-butyl (R)-2,2-dimethyl-4-(4-oxocyclohexyl)oxazolidine-3-carboxylate To a solution of (R)-tert-butyl 4-(4-hydroxycyclohexyl)-2,2-dimethyloxazolidine-3-carboxylate (10 g, 0.033 mol) in DCM (300 mL) was added DMP (44.5 g, 0.1 mol). The mixture was stirred at 25'C for 12 hrs. TLC indicated reactant was consumed completely. The mixture was washed with saturated aq. $NaHCO_3$, and then dried over anhydrous $Na_2SO_4$, filtered and concentrated under reduced pressure. The residue was purified by column chromatography on silica gel (eluent: PE:EA=5:1) to give ((R)-tert-butyl 2,2-dimethyl-4-(4-oxocyclohexyl)oxazolidine-3-carboxylate (2.6 g, 26.5% yield) was obtained as solid. $^1H$ NMR (400 MHz, DMSO-$d_6$) δ ppm: 3.68-3.89 (m, 3H), 2.30-2.45 (m, 2H), 2.19 (d, J=14.0 Hz, 2H), 2.01-2.26 (m, 1H), 1.85-1.96 (m, 1H), 1.75-1.85 (m, 1H), 1.49 (s, 3H), 1.42 (s, 14H).

Synthesis of tert-butyl $(R)_4$-(4-hydroxy-4-methylcyclohexyl-2,2-dimethyloxazolidine-3-carboxylate To a solution of (R)-tert-butyl 2,2-dimethyl-4-(4-oxocyclohexyl)oxazolidine-3-carboxylate (2.6 g, 8.74 mmol) in THF (100 mL) was added MeLi (1M, 26 mL, 26.23 mmol) dropwise at −78° C. under $N_2$ atmosphere. The mixture was stirred at −60° C. for 4 hr. TLC indicated reactant was consumed completely. The mixture was quenched with aq. $NH_4Cl$, and then extracted with EA (50 mL×2). The organic layer was dried, filtered and concentrated under reduced pressure. The residue was purified by column chromatography on silica gel (eluent: PE:EA=10:1) to give (R)-tert-butyl 4-(4-hydroxy-4-methylcyclohexyl)-2,2-dimethyloxazolidine-3-carboxylate (1.6 g, 58.5% yield). MS (ESI, m/e) $[M+1]^+$ 314.2.

Synthesis of (R)-4-(1-amino-2-hydroxyethyl)-1-methylcyclohexan-1-ol

To a solution of (R)-tert-butyl-4-(4-hydroxy-4-methylcyclohexyl)-2,2-dimethyloxazolidine-3-carboxylate (1.6 g, 5.1 mmol, 1 eq) in EA (50 mL) was added HCl in EA (4M, 10 mL). The mixture was stirred at 25'C for 1 hr TLC indicated reactant was consumed completely. The mixture was concentrated to give (R)-4-(1-amino-2-hydroxyethyl)-1-methylcyclohexanol (1.0 g, crude), which was used into the next step without further purification. MS (ESI, m/e) $[M+1]^+$ 174.1.

Synthesis of (R)-3-bromo-4-((2-hydroxy-1-(4-hydroxy-4- methylcyclohexylethyhamino)-5-nitrobenzenesulfonamide To a solution of 3-bromo-4-chloro-5-nitrobenzenesulfonamide (1 g, 3.18 mmol) and (R)-4-(1-amino-2-hydroxyethyl)-1-methylcyclohexanol (1 g, 4.77 mmol) in DMF (20 mL) was added DIEA (1.64 g, 12.72 mmol). The mixture was stirred at 60'C for 4 hr. TLC indicated reactant was consumed completely. The reaction mixture was poured into water (50 mL) and then extracted with EA (50 mL×2). The organic layer was washed with brine, and then dried over anhydrous $Na_2SO_4$, filtered and concentrated under reduced pressure to give crude (R)-3-bromo-4-((2-hydroxy-1-(4-hydroxy-4- methylcyclohexyl)ethyl)amino)-5-nitrobenzenesulfonamide. The crude product was purified and separated by column chromatography on silica gel (eluent: Petroleum ether:Ethyl acetate=5:1) to obtain 2 isomer: 210 mg of the faster isomer (15% yield), $^1$H NMR (400 MHz, $CDCl_3$) δ ppm: 8.45 (d, J=2.0 Hz, 1H), 8.17 (d, J=2.0 Hz, 11H), 8.02 (br, 3H), 6.98 (br, 1H), 5.03 (s, 2H), 3.97 (d, J=5.0 Hz, 1H), 3.81 (s, 2H), 1.65-1.72 (m, 4H), 1.38-1.49 (m, 4H), 1.23 (s, 3H), MS (ESI, m/e) $[M+1]^+$ 453.1; 240 mg of the slower isomer (17% yield), MS (ESI, m/e) $[M+1]^+$ 453.1.

Synthesis of (R)-3-((1S,4S)-4-hydroxy-4-methylcyclohexyl)-5-nitro-3,4-dihydro-2H-benzo[b][1.4]oxazine-7-sulfonamide (A2-1a)

To a solution of the faster isomer of (R)-3-bromo-4-((2-hydroxy-1-(4-hydroxy-4-methylcyclohexyl)ethyl)amino)-5-nitrobenzenesulfonamide (210 mg, 0.46 mmol) in 1,2-dioxane (20 mL) was added $Pd_2(dba)_3$ (64 mg, 0.07 mmol), Xantphos (68 mg, 0.12 mmol) and $Cs_2CO_3$ (304 mg, 0.93 mmol). The mixture was degassed and then stirred at 100° C. for 10 hrs under Ar atmosphere. LC-MS showed reactant was consumed completely. After cooled to room temperature, the mixture was filtered through a celite pad. The filtrate was concentrated under reduced pressure. The residue was purified by silica gel (eluent: PE:EA=5:1) to give (R)-3-((1S,4S)-4-hydroxy-4-methylcyclohexyl)-5-nitro-3,4-dihydro-2H-benzo[b][1,4]oxazine-7-sulfonamide (75 mg, 43.6% yield) as a solid. $^1$H NMR (400 MHz, DMSO-$d_6$) δ ppm: 8.75 (br, 1H), 8.08 (s, 1H), 7.31 (br, 3H), 4.34 (dd, J=3.0, 10.8 Hz, 1H), 4.12 (d, J=8.8 Hz, 1H), 3.97 (s, 1H), 3.52 (br, 1H), 1.43-1.61 (m, 7H), 1.24 (br, 2H), 1.08 (s, 3H). MS (ESI, m/e) $[M+1]^+$ 370.0.

With the slower isomer of (R)-3-bromo-4-((2-hydroxy-1-(4-hydroxy-4-methylcyclohexyl)ethyl)amino)-5-nitrobenzenesulfonamide (240 mg, 0.53 mmol) as material, 100 mg (51% yield) of (R)-3-((1R,4R)-4-hydroxy-4-methylcyclohexyl)-5-nitro-3,4-dihydro-2H-benzo[b][1,4]oxazine-7-sulfonamide (A2-1b) was obtained following the similar procedure of A2-1a. $^1$H NMR (400 MHz, DMSO-$d_6$) δ ppm: 8.74 (br s, 1H), 8.08 (s, 1H), 7.31 (br, 3H), 4.19-4.40 (m, 2H), 4.03-4.18 (m, 1H), 3.57 (br, 1H), 1.43-1.77 (m, 5H), 1.27-1.41 (m, 3H), 1.14-1.22 (m, 1H), 1.09 (s, 3H). MS (ESI, m/e) $[M+1]^+$ 370.0.

The desired compound was synthesized with A1-5 and (R)-3-((1S,4S)-4-hydroxy-4-methylcyclohexyl)-5-nitro-3,4-dihydro-2H-benzo[b][1,4]oxazine-7-sulfonamide (A2-1a) following the procedures similar to those in preparation of Example A1. $^1$H NMR (400 MHz, DMSO-$d_6$) δ ppm: 11.62 (s, 1H), 11.36 (s, 0.5H), 8.72 (s, 1H), 8.13 (s, 1H), 7.99 (s, 1H), 7.63-7.38 (m, 4H), 7.30-7.21 (m, 4H), 6.66-6.64 (m, 1H), 6.35 (s, 1H), 6.16 (s, 1H), 4.25-4.42 (m, 1H), 4.07-4.05 (m, 1H), 3.96 (s, 1H), 3.47 (s, 1H), 2.98-2.94 (m, 5H), 1.82 (s, 5H), 1.63-1.28 (m, 16H), 1.19-1.14 (m, 11H), 1.06 (s, 3H). MS (ESI) m/e $[M+1]^+$ 917.9.

Example A3: 2-((1H-pyrrolo[2,3-b]pyridin-5-yl)oxy)-N—(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3,5]nonan-7-yl)benzamide

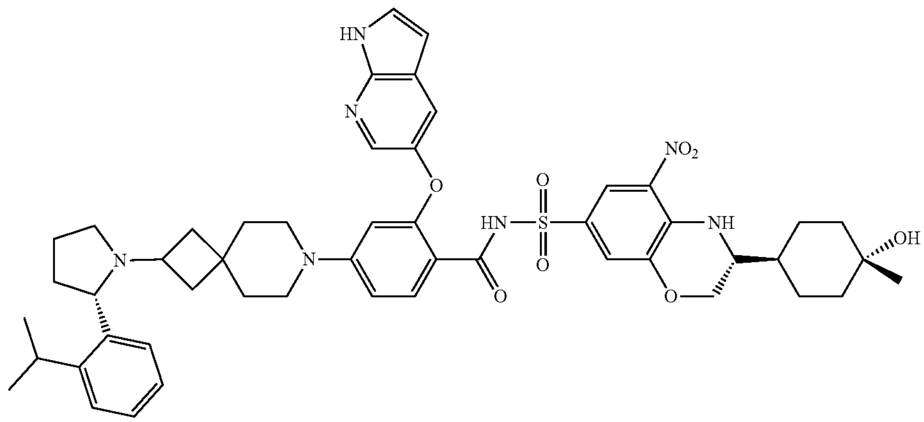 [SMILES: CC(C)c1ccccc1[C@@H]1CCCN1C1CC2(CCN(c3ccc(C(=O)NS(=O)(=O)c4cc5c(c([N+](=O)[O-])c4)N[C@H]([C@H]4CC[C@](C)(O)CC4)CO5)c(Oc4cnc5[nH]ccc5c4)c3)CC2)C1]

The desired compound was synthesized with A1-5 and (R)-3-((1R,4R)-4-hydroxy-4-methylcyclohexyl)-5-nitro-3,4-dihydro-2H-benzo[b][1,4]oxazine-7-sulfonamide (A2-1b) following the procedures similar to those in preparation of Example A1. $^1$H NMR (400 MHz, DMSO-$d_6$) δ ppm: 11.67 (s, 1H), 11.42 (s, 1H), 10.61-10.31 (m, 0.5H), 8.79 (s, 1H), 8.18 (s, 1H), 8.03 (s, 1H), 7.86 (s, 1H), 7.50-7.49 (m, 3H), 7.39-7.18 (m, 4H), 6.68 (d, J=9.2 Hz, 1H), 6.37 (s, 1H), 6.17 (s, 1H), 4.73 (s, 1H), 4.27-4.26 (m, 2H), 4.06 (d, J=8.4 Hz, 11H), 3.85 (s, 11H), 3.67 (s, 11H), 3.55-3.54 (m, 1H), 3.28 (s, 1H), 3.00-2.98 (m, 5H), 2.39 (s, 1H), 2.20-1.93 (m, 4H), 1.68-1.67 (m, 2H), 1.56-1.54 (m, 3H), 1.34-1.33 (m, 7H), 1.27-1.25 (m, 7H), 1.10-1.07 (m, 6H), MS (ESI) m/e $[M+1]^+$ 917.9.

Example A4: 2-((1H-pyrrolo[2,3-b]pyridin-5-yl)oxy)-N—(((R)-3-(((1R,4R)-4-hydroxycyclohexyl)methyl)-5-nitro-3,4-dihydro-2H-benzo[b][1,4]oxazin-7-yl)sulfonyl)-4-(2-((S)-2-(2-isopropylphenyl)pyrrolidin-1-yl)$_7$-azaspiro[3,5]nonan-7-yl)benzamide

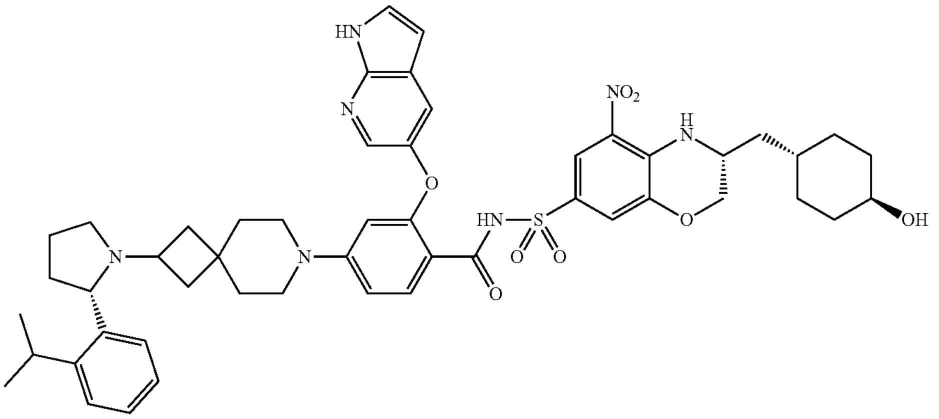 [SMILES: CC(C)c1ccccc1[C@@H]1CCCN1C1CC2(CCN(c3ccc(C(=O)NS(=O)(=O)c4cc5c(c([N+](=O)[O-])c4)N[C@H](C[C@H]4CC[C@H](O)CC4)CO5)c(Oc4cnc5[nH]ccc5c4)c3)CC2)C1]

A4-1a: (R)-3-(((1R,4R)-4-hydroxycyclohexyl)methyl)-5-nitro-3,4-dihydro-2H-benzo[b][1,4]oxazine-7-sulfonamide

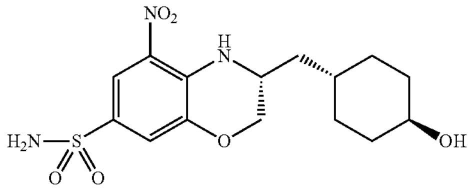 [SMILES: NS(=O)(=O)c1cc2c(c([N+](=O)[O-])c1)N[C@H](C[C@H]1CC[C@H](O)CC1)CO2]

Synthesis of 3-bromo-4-chloro-5-nitrobenzenesulfonamide

The mixture of 4-chloro-3-nitrobenzenesulfonamide (4.0 g, 16.9 mmol) in $H_2SO_4$ (12 mL, 98%) was warmed to 60° C. for 15 min. Then NBS (6.02 g, 33.81 mmol) was added in portions over 5 minutes. After the addition of NBS, the mixture was stirred at 60° C. for 4 hrs in sealed tube. The four parallel reactions were combined and poured into ice water (500 mL) and stirred at 0° C. for 5 min. After filtered, the filter cake was triturated in EtOAc (20 mL) until the solid was dissolyed completely. Then Petroleum ether (50 mL) was added slowly. The white precipitate was filtered, and the filter cake was washed with petroleum ether (50 mL) and dried over vacuum to afford 3-bromo-4-chloro-5-nitrobenzenesulfonamide (3.9 g). The filtrate was concentrated in vacuum. The residue was purified by column chromatography on silica gel to give 3-bromo-4-chloro-5-nitrobenzenesulfonamide (2.2 g), total yield: 28.3%. MS (ESI, m/e) $[M+1]^+$ 312.8.

Synthesis of (R)-methyl 2-((tert-butoxycarbonyl)amino)-3-(4-hydroxycyclohexyl)propanoate To a mixture of (R)-methyl 2-((tert-butoxycarbonyl)amino)-3-(4-hydroxyphenyl)propanoate (20.0 g, 67.72 mmol) in i-PrOH (400 mL) and AcOH (60 mL) was added $PtO_2$ (384.5 mg, 1.69 mmol) under Ar. The suspension was degassed under vacuum and purged with $H_2$. The mixture was stirred under $H_2$ (50 Psi) at 50° C. for 48 h. The reaction mixture was filtered and the filter was concentrated to remove most of i-PrOH and poured into water, extracted with EtOAc, concentrated in vacuum to give (R)-methyl 2-((tert-butoxycarbonyl)amino)-3-(4-hydroxycyclohexyl)propanoate (22.0 g). $^1$H NMR (400 MHz, $CDCl_3$) δ ppm: 4.82-4.93 (m, 1H), 4.21-4.31 (m, 1H), 3.66 (d, J=2.0 Hz, 3H), 3.42-3.55 (m, 1H), 2.02 (s, 2H), 1.40-1.95 (m, 7H), 1.38 (s, 8H), 0.71-1.32 (m, 4H).

Synthesis of (R)-tert-butyl (1-hydroxy-3-(4-hydroxycyclohexylpropan-2-yl)carbamate To a solution of (R)-methyl 2-((tert-butoxycarbonyl)amino)-3-(4-hydroxycyclohexyl) propanoate (20.0 g, 66.36 mmol) in EtOH (200 mL) was added $NaBH_4$ (3.77 g, 99.54 mmol) in portion at 0° C. Then MeOH (0.4 mL) was added at 0° C. The mixture was stirred at 50° C. for 48 hrs. The reaction mixture was poured into water (400 mL), extracted with EtOAc (400 mL-2) and concentrated in vacuum to give (R)-tert-butyl (1-hydroxy-3-(4-hydroxycyclohexyl)propan-2-yl)carbamate (17.0 g) as an oil. $^1$H NMR (400 MHz, $CDCl_3$) δ ppm: 4.56 (s, 1H), 3.50-3.85 (m, 3H), 1.54-2.02 (m, 8H), 1.45 (s, 9H), 0.76-1.39 (m, 9H).

Synthesis of (R)-4-(2-amino-3-hydroxyyropyl)cyclohexanol hydrochloride

A solution of (R)-tert-butyl (1-hydroxy-3-(4-hydroxycyclohexyl)propan-2-yl) carbamate (7.0 g, 25.61 mmol) in HCl solution in EtOAc (2M, 100 mL) was stirred at 20° C. for 3 hrs. TLC monitor indicated the reaction was completed. The reaction mixture was concentrated in vacuum to give (R)-4-(2-amino-3-hydroxypropyl)cyclohexanol hydrochloride (4.8 g, crude) as an oil.

Synthesis of (R)-3-bromo-4-((1-hydroxy-3-(4-hydroxycyclohexyl)propan-2-yl)amino)-5-nitrobenzenesulfonamide To a mixture of 3-bromo-4-chloro-5-nitrobenzenesulfonamide (5.4 g, 17.11 mmol) and (R)-4-(2-amino-3-hydroxynrooyl)cyclohexanol hydrochloride (4.7 g, 22.25 mmol) in DMF (60 mL) was added DIPEA (22.12 g, 171.14 mmol) at 20° C. The mixture was stirred at 50° C. for 12 h. After cooled to room temperature, the reaction mixture was poured into water (100 mL), extracted with EtOAc (100 mL) and concentrated in vacuum. The residue was purified by column chromatography on silica gel (eluent: PE:EA=10:1 to 0:1). (R)-3-bromo-4-((1-hydroxy-3-(4-hydroxycyclohexyl)propan-2-yl)amino)-5-nitrobenzenesulfonamide (2.15 g, 27.7% yield) was obtained as a solid. $^1$H NMR (400 MHz, methanol-$d_4$) δ ppm: 8.36 (t, J=1.7 Hz, 1H), 8.20 (d, J=2.1 Hz, 1H), 3.94-4.05 (m, 1H), 3.86 (s, 1H), 3.52-3.64 (m, 2H), 3.33-3.51 (m, 1H), 1.85-1.97 (m, 1H), 1.38-1.80 (m, 10H), 1.23-1.38 (m, 2H), 0.84-1.22 (m, 3H). MS (ESI, m/e) $[M+1]^+$ 453.2.

Synthesis of (R)-3-(((1R,4R)-4-hydroxycyclohexyl) methyl)-5-nitro-3,4-dihydro-2H-benzo[b][1.4] oxazine-7-sulfonamide To a mixture of (R)-3-bromo-4-((1-hydroxy-3-(4-hydroxycyclohexyl)propan-2-yl)amino)-5-nitrobenzenesulfonamide (2.15 g, 4.75 mmol) in dioxane (40 mL) was added $Cs_2CO_3$ (3.10 g, 9.51 mmol), $Pd_2(dba)_3$ (652.9 mg, 712.99 umol) and Xantphos (687.6 mg, 1.19 mmol) at 20° C. under Ar atmosphere. The mixture was stirred at 90° C. for 3 hrs. LC/MS indicated the reaction was completed. The reaction mixture was cooled to room temperature and filtered through a celite pad. The filtrate was concentrated in vacuum and the residue was purified by prep-HPLC. 704 mg of (R)-3-(((1R, 4R)-4-hydroxycyclohexyl)methyl)-5-nitro-3,4-dihydro-2H-benzo[b][1,4]oxazine-7-sulfonamide was obtained as faster isomer A4-1a (retention time: 2.16 min), yield: 39.8%; $^1$H NMR (400 MHz, DMSO-$d_6$) δ ppm: 8.71 (d, J=3.2 Hz, 1H), 8.08 (d, J=2.1 Hz, 1H), 7.26-7.37 (m, 3H), 4.22-4.64 (m, 1H), 4.09-4.17 (m, 2H), 3.81 (dd, J=6.8, 3.4 Hz, 1H), 3.33 (s, 1H), 1.75-1.86 (m, 3H), 1.68-1.75 (m, 1H), 1.52 (s, 2H), 1.30-1.37 (m, 1H), 1.08-1.20 (m, 2H), 0.87-0.99 (m, 2H). MS (ESI, m/e) $[M+1]^+$ 372.2.

A4-1b: (R)-3-(((1S,4S1-4-hydroxycyclohexyl) methyl)-5-nitro-3,4-dihydro-2H-benzo[b][1,4] oxazine-7-sulfonamide

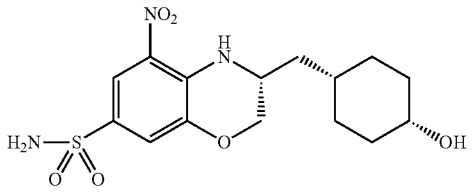 [SMILES: NS(=O)(=O)c1cc2c(c([N+](=O)[O-])c1)N[C@H](C[C@H]1CC[C@@H](O)CC1)CO2]

460 mg of slower isomer R-3-(((1S,4S)-4-hydroxycyclohexyl)methyl)-5-nitro-3,4-dihydro-2H-benzo[b][1,4] oxazine-7-sulfonamide (A4-1b, retention time: 2.22 min) was obtained with the yield of 26.0%. MS (ESI, m/e) $[M+1]^+$ 372.2.

A4: 2-((1H-pyrrolo[2,3-b]pyridin-5-yl)oxy)-N—(((R)-3-(((1R,4R)-4-hydroxycyclohexyl)methyl)-5-nitro-3,4-dihydro-2H-benzo[b][1,4]oxazin-7-yl) sulfonyl)-4-(2-((S)-2-(2-isopropylphenyl)pyrrolidin-1-yl)-7-azaspiro[3,5]nonan-7-yl)benzamide A mixture of (S)-2-((1H-pyrrolo[2,3-b]pyridin-5-yl)oxy)-4-(2-(2-(2-isopropylphenyl)pyrrolidin-1-yl)-7-azaspiro[3,5] nonan-7-yl)benzoic acid (169 mg, 0.3 mmol), (R)-3-(((1R, 4R)-4-hydroxycyclohexyl)methyl)-5-nitro-3,4-dihydro-2H-benzo[b][1,4]oxazine-7-sulfonamide (111 mg, 0.3 mmol, A4-1a), EDCT (75 mg, 0.39 mmol), TEA (0.1 mL) and DMAP (73 mg, 0.6 mmol) in DCM (25 mL) was stirred overnight at room temperature. The reaction mixture was quenched with 10% HOAc (20 mL) and washed with saturated aq. $NaHCO_3$ (10 mL×2), brine (10 mL), then dried over anhydrous $Na_2SO_4$, concentrated in vacuum. The residue was purified by prep-HPLC to give the desired compound 109 mg (yield: 39.5%). $^1$H NMR (400 MHz, DMSO-$d_6$): 11.63 (s, 1H), 11.40 (s, 1H), 8.79-8.71 (m, 1H), 8.17-8.13 (m, 1H), 8.00 (s, 1H), 7.71-7.40 (m, 4H), 7.34-6.97 (m, 4H), 6.66 (d, J=8.2 Hz, 1H), 6.35 (s, 1H), 6.16 (s, 1H), 4.47 (d, J=4.3 Hz, 1H), 4.12-4.06 (m, 2H), 3.77 (s, 1H), 3.64-3.59 (m, 1H), 3.29-3.28 (m, 1H), 3.05-2.91 (m, 8H), 1.94-1.59 (m, 7H), 1.52-1.26 (m, 10H), 1.21-1.14 (m, 9H), 1.03-0.77 (m, 3H). MS (ESI, m/e) $[M+1]^+$ 917.9.

Example A5: 2-((1H-pyrrolo[2,3-b]pyridin-5-yl) oxy)-N—(((R)-3-(((1s,4S)-4-hydroxycyclohexyl) methyl)-5-nitro-3,4-dihydro-2H-benzo[b][1,4] oxazin-7-yl)sulfonyl)-4-(2-((S)-2-(2-isopropylphenyl)pyrrolidin-1-yl)-7-azaspiro[3,5] nonan-7-yl)benzamide

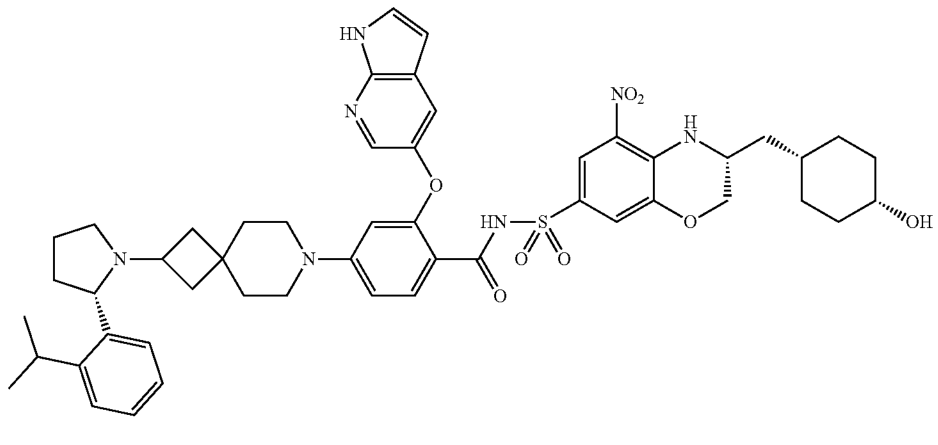 [SMILES: CC(C)c1ccccc1[C@@H]1CCCN1C1CC2(CCN(c3ccc(C(=O)NS(=O)(=O)c4cc5c(c([N+](=O)[O-])c4)N[C@H](C[C@H]4CC[C@@H](O)CC4)CO5)c(Oc4cnc5[nH]ccc5c4)c3)CC2)C1]

The desired compound was synthesized with A 1-5 and (R)-3-(((1S,4S)-4-hydroxycyclohexyl)methyl)-5-nitro-3,4-dihydro-2H-benzo[b][1,4]oxazine-7-sulfonamide (A4-1b) following the procedures similar to those in preparation of Example A1. $^1$H NMR (400 MHz, DMSO-da) δ ppm: 11.63 (s, 1H), 8.69 (s, 1H), 8.13 (s, 1H), 8.00 (d, J=2.2 Hz, 1H), 7.65 (s, 1H), 7.49-7.47 (m, 3H), 7.28-7.26 (m, 4H), 6.65 (d, J=7.4 Hz, 1H), 6.35 (s, 1H), 6.17 (s, 1H), 4.29 (d, J=3.0 Hz, 1H), 4.12-4.11 (m, 1H), 4.03-4.01 (m, 1H), 3.78-3.75 (m, 2H), 3.31-3.23 (m, 3H), 2.98-2.96 (m, 5H), 2.26 (s, 1H), 1.89 (s, 5H), 1.55-1.52 (m, 3H), 1.40-1.38 (m, 15H), 1.23 (s, 11H), 1.19 (d, J=6.6 Hz, 3H), 1.13 (d, J=6.6 Hz, 3H). MS (ESI) m/e $[M+1]^+$ 917.9.

Example A6: 2-((1H-pyrrolo[2,3-b]pyridin-5-yl)oxy)-N—(((R)-3-(((1r,4R)-4-hydroxycyclohexyl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3,5]nonan-7-yl-6,6,8,8-d4)benzamide

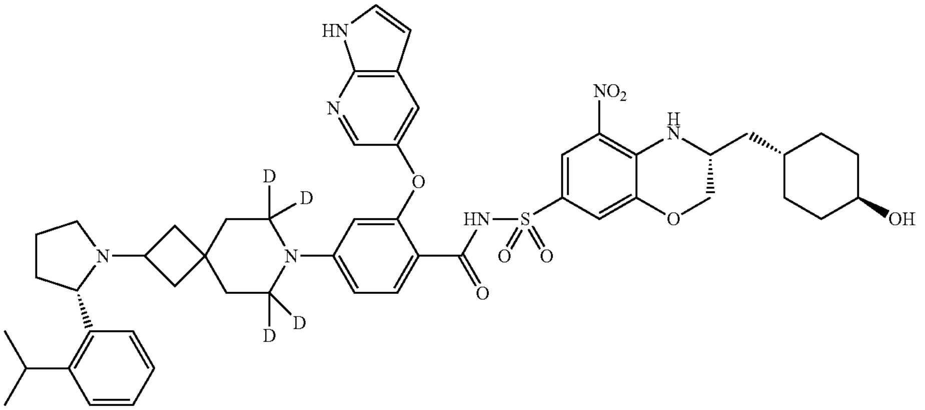 [SMILES: [2H]C1([2H])CC2(CC(N3CCC[C@H]3c3ccccc3C(C)C)C2)CC([2H])([2H])N1c1ccc(C(=O)NS(=O)(=O)c2cc3c(c([N+](=O)[O-])c2)N[C@H](C[C@H]2CC[C@H](O)CC2)CO3)c(Oc2cnc3[nH]ccc3c2)c1]

A6-1: 2,2-dimethoxy-7-azaspiro[3,5]nonane-6,6,8,8-d4

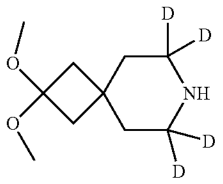 [SMILES: [2H]C1([2H])CC2(CC([2H])([2H])N1)CC(OC)(OC)C2]

Synthesis of 7-nitroso-7-azaspiro[3,5]nonan-2-one

To a solution of 2,2-dimethoxy-7-azaspiro[3,5]nonane hydrochloride (22.1 g, 100.0 mmol) and $NaNO_2$ (13.8 g, 200.0 mmol) in $H_2O$ (200 mL) was added HOAc (12.6 g, 200.0 mmol) dropwise at room temperature, the solution was stirred at room temperature for 2 hrs. The reaction mixture was extracted with DCM (100 mL×2). The combined organic layers were dried over anhydrous $Na_2SO_4$ and concentrated to give the product (16.0 g, crude). MS (ESI, m/e) $[M+1]^+$ 169.0.

Synthesis of 2,2-dimethoxy-7-nitroso-7-azaspiro[3,5]nonane

A solution of 7-nitroso-7-azaspiro[3,5]nonan-2-one (16.0 g, 95.24 mmol) in $CH_3OH$ (200 mL) and 1N HCl acid (20 mL, ether solution) was stirred at room temperature for 16 hrs. The reaction mixture was concentrated in vacuum and the residue was purified by column chromatograph on silica gel (eluent: EA:PE=1:5) to give the product (20.1 g, yield: 98.5%). MS (ESI, m/e) $[M+1]^+$ 215.0.

Synthesis of 2,2-dimethoxy-7-nitroso-7-azaspiro[3,5]nonane-6,6,8,8-d4

A mixture of 2,2-dimethoxy-7-nitroso-7-azaspiro[3,5]nonane (1.7 g, 7.944 mmol) and t-BuONa (3.8 g, 39.720 mmol) in $D_2O$ (10 mL) and $CD_3OD$ (5 mL) was stirred in a Heavy-Wall Pressure Vessel at 120° C. under $N_2$ for 20 hrs. The reaction mixture was cooled to room temperature and extracted with DCM (50 mL), washed with saturated NaCl solution (10 mL). The organic layer was separated, concentrated and purified by column chromatograph on silica gel (eluent: EA:PE=1:5) to give the crude product. Repeated the above procedure for 3 times, 2,2-dimethoxy-7-nitroso-7-azaspiro[3,5]nonane-6,6,8,8-d4 was obtained (400 mg, yield: 23.5%). MS (ESI, m/e) [M+1]219.0.

Synthesis of 2,2-dimethoxy-7-azaspiro[3,5]nonane-6,6,8,8-d4

To a mixture of 2,2-dimethoxy-7-nitroso-7-azaspiro[3,5]nonane-6,6,8,8-d4 (400 mg, 1.835 mmol) and t-BuONa (980 mg, 9.174 mmol) in $CD_3OD$ (5 mL) and D20 (5 mL) was added Nickel-Aluminum alloy (900 mg, 9.174 mmol) in portions, the mixture was stirred at room temperature for 0.5 hour. Filtered, the mother liquid was diluted with DCM (20 mL) and washed with saturated NaCl (5 mL). The combined organic layer was dried over $Na_2SO_4$ and concentrated in vacuum to give the product (350 mg, crude). $^1$H NMR (400 MHz, DMSO-$d_6$) δ ppm: 3.01 (s, 6H), 1.81 (s, 4H), 1.38 (s, 4H). MS (ESI, m/e) 190.0.

A6-2: methyl 2-((1H-pyrrolo[2,3-b]pyridin-5-yl)oxyl-4-(2,2-dimethoxy-7-azaspiro[3,5]nonan-7-yl-6,6,8,8-d4)benzoate

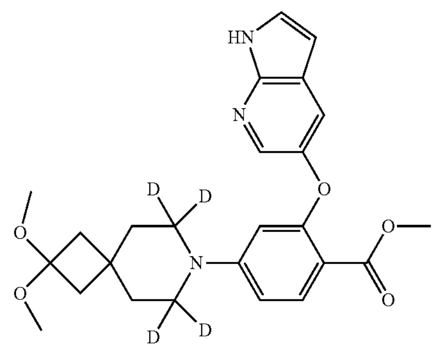 [SMILES: [2H]C1([2H])CC2(CC(OC)(OC)C2)CC([2H])([2H])N1c1ccc(C(=O)OC)c(Oc2cnc3[nH]ccc3c2)c1]

A6-2 was synthesized following the similar procedure of A1-1 by replacing 2,2-dimethoxy-7-azaspiro[3,5]nonane with 2,2-dimethoxy-7-azaspiro[3,5]nonane-6,6,8,8-d4. MS (ESI, m/e) $[M+1]^+$ 456.3.

The desired compound example 8 was synthesized with (S)-2-((1H-pyrrolo[2,3-b]pyridin-5-yl)oxy)-4-(2-(2-(2-isopropylphenyl)pyrrolidin-1-yl)-7-azaspiro[3,5]nonan-7-yl-6,6,8,8-d4)benzoic acid and (R)-3-(((1R,4R)-4-hydroxycyclohexyl)methyl)-5-nitro-3,4-dihydro-2H-benzo[b][1,4]oxazine-7-sulfonamide following the similar procedure of A4. $^1H$ NMR (400 MHz, DMSO-$d_6$) δ ppm: 11.66 (s, 1H), 8.76 (s, 1H), 8.17 (s, 1H), 8.02 (s, 1H), 7.77 (s, 1H), 7.49 (d, J=7.2 Hz, 3H), 7.38-7.13 (m, 4H), 6.66 (d, J=8.4 Hz, 1H), 6.36 (s, 1H), 6.16 (s, 1H), 4.48 (s, 1H), 4.16-3.99 (m, 2H), 3.78 (s, 1H), 2.40-2.28 (m, 1H), 2.17-1.63 (m, 10H), 1.54-1.05 (m, 21H), 0.99-0.87 (m, 2H). MS (ESI, m/e) $[M+1]^+$ 923.1.

Example A7: 2-((1H-pyrrolo[2,3-b]pyridin-5-yl)oxy)-N—(((R)-3-(((1r,4R)-4-hydroxycyclohexyl)methyl)-5-nitro-3,4-dihydro-2H-benzo[b][1,4]oxazin-7-yl)sulfonyl)-4-(2-(2-(2-isopropylphenyl)pyrrolidin-1-yl-2,5,5-d3)-7-azaspiro[3,5]nonan-7-v)benzamide

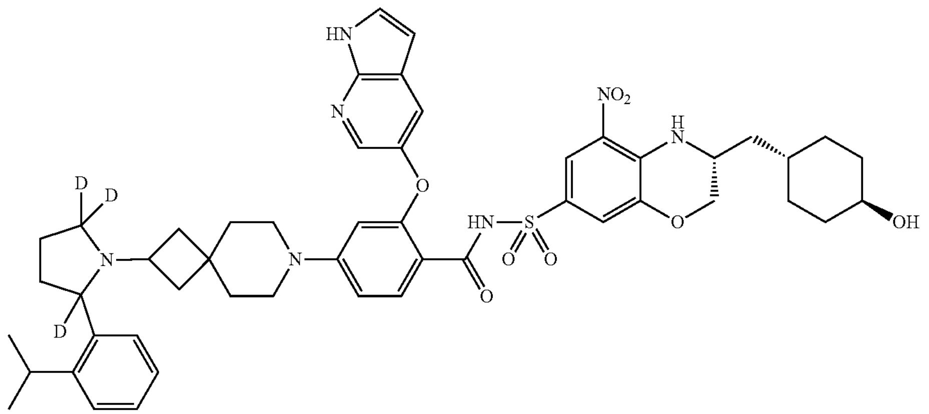 [SMILES: [2H]C1([2H])CCC([2H])(c2ccccc2C(C)C)N1C1CC2(CCN(c3ccc(C(=O)NS(=O)(=O)c4cc5c(c([N+](=O)[O-])c4)N[C@H](C[C@H]4CC[C@H](O)CC4)CO5)c(Oc4cnc5[nH]ccc5c4)c3)CC2)C1]

A7-1: 2-(2-isopropylphenyl)pyrrolidine-2,5,5-d3

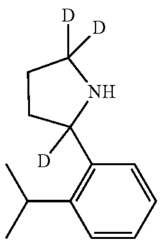 [SMILES: [2H]C1([2H])CCC([2H])(c2ccccc2C(C)C)N1]

Synthesis of 2-(2-isopropylphenyl)-1-nitrosopyrrolidine

To a solution of (S)-2-(2-isopropylphenyl)pyrrolidine hydrochloride (9.0 g, 40.0 mmol) in $H_2O$ (100 mL) and HCl acid (2N, 12 mL) was added a solution of $NaNO_2$ (6.9 g, 100.0 mmol) in $H_2O$ (30 mL) dropwise at about 5° C. After addition, the mixture was stirred at 5° C. for 2 hrs, then warmed to room temperature and stirred for 16 hrs. The resulting precipitate was filtered, and the cake was washed with $H_2O$ (50 mL) and then dried at 50° C. under vacuum for 1 hour to give the product as a solid. (5.3 g, yield: 95.2%). MS (ESI, m/e) $[M+1]^+$ 219.0.

Synthesis of 2-(2-isopropylphenyl)-1-nitrosopyrrolidine-2,5,5-d3

A mixture of 2-(2-isopropylphenyl)-1-nitrosopyrrolidine (1.4 g, 6.42 mmol) and t-BuONa (3.1 g, 32.11 mmol) in D20 (9 mL) and $CD_3OD$ (4.5 mL) was stirred in a Heavy-Wall Pressure Vessel at 95° C. under $N_2$ for 22 hrs. After cooled to room temperature, the reaction mixture was diluted with DCM (30 mL) and then washed with saturated NaCl solution (10 mL). The organic layer was separated, dried with anhydrous $Na_2SO_4$, concentrated in vacuum. The residue was purified by column chromatograph on silica gel (eluent: EA:PE=1:5) to give the crude product. Repeated the above procedure for 2 times, 2-(2-isopropylphenyl)-1-nitrosopyrrolidine-2,5,5-d3 was obtained (1.1 g, yield: 64.10%). $^1H$ NMR (400 MHz, DMSO-$d_6$) δ ppm: 7.52 (dd, J=1.6 Hz, 7.6 Hz, 1H), 7.26-7.21 (m, 1H), 7.18-7.08 (m, 2H), 3.45-3.00

(m, 2H), 2.15-2.05 (m, 1H), 1.81-1.67 (m, 2H), 1.44-1.32 (m, 1H), 1.18 (d, J=7.2 Hz, 6H). MS (ESI, m/e) $[M+1]^+$ 443.0.

A7-2: methyl 2-((1H-pyrrolo[2,3-b]pyridin-5-yl) oxy)-4-(2-(2-(2-isopropylphenyl)pyrrolidin-1-yl-2,5,5-d3)-7-azaspiro[3,5]nonan-7-yl)benzoate

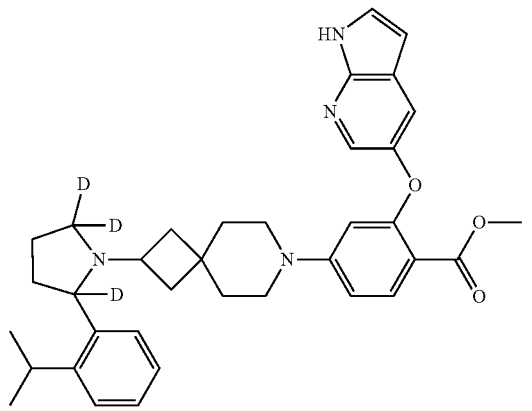 [SMILES: [2H]C1([2H])CCC([2H])(c2ccccc2C(C)C)N1C1CC2(CCN(c3ccc(C(=O)OC)c(Oc4cnc5[nH]ccc5c4)c3)CC2)C1]

This compound was synthesized following the similar procedures in A1-4 by replacing (S)-2-(2-isopropylphenyl) pyrrolidine hydrochloride with 2-(2-isopropylphenyl)-1-nitrosopyrrolidine-2,5,5-d3. MS (ESI, m/e) $[M+1]^+$ 582.4.

The desired compound (example A7) was synthesized with 2-((1H-pyrrolo[2,3-b]pyridin-5-yl)oxy)-4-(2-(2-(2-isopropylphenyl)pyrrolidin-1-yl-2,5,5-d3)-7-azaspiro[3,5] nonan-7-yl)benzoic acid and (R)-3-(((1R,4R)-4-hydroxycyclohexyl)methyl)-5-nitro-3,4-dihydro-2H-benzo[b][1,4] oxazine-7-sulfonamide following the similar procedure of A4. $^1$H NMR (400 MHz, DMSO-$d_6$) δ ppm: 11.72 (s, 1H), 8.82 (s, 1H), 8.23 (s, 1H), 8.08 (s, 1H), 7.91 (s, 1H), 7.55 (d, J=8.0 Hz, 3H), 7.44-7.22 (m, 4H), 6.73 (d, J=8.8 Hz, 1H), 6.43 (s, 1H), 6.23 (s, 1H), 4.55 (s, 1H), 4.13 (m, 2H), 3.85 (s, 1H), 3.18-2.90 (m, 4H), 2.48-2.34 (m, 1H), 2.19-1.97 (m, 4H), 1.93-1.75 (m, 4H), 1.58-1.13 (m, 20H), 1.07-0.94 (m, 2H). MS (ESI, m/e) $[M+1]^+$ 922.1.

Example A8: 2-((1H-pyrrolo[2,3-b]pyridin-5-yl) oxy)-4-(2-((S)-2-(2-isopropylphenyl)pyrrolidin-1-yl)-7-azaspiro[3,5]nonan-7-yl)-N-((2-(morpholinomethyl)-7-nitroindolin-5-yl)sulfonyl)benzamide

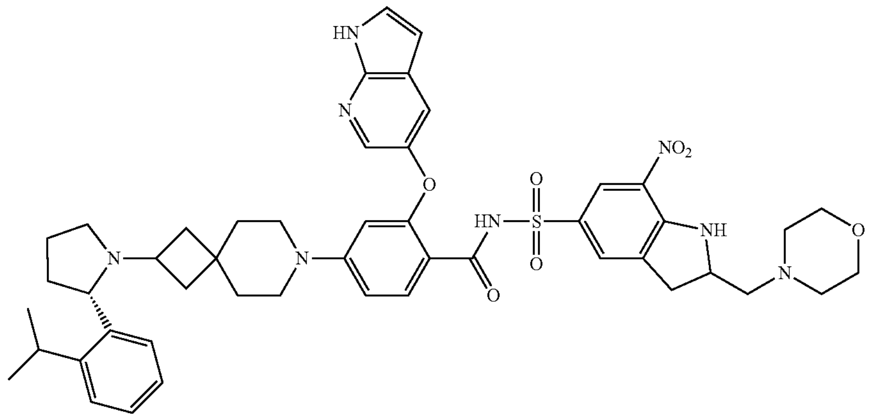 [SMILES: CC(C)c1ccccc1[C@@H]1CCCN1C1CC2(CCN(c3ccc(C(=O)NS(=O)(=O)c4cc5c(c([N+](=O)[O-])c4)NC(CN4CCOCC4)C5)c(Oc4cnc5[nH]ccc5c4)c3)CC2)C1]

A8-1: 2-(morpholinomethyl)-7-nitroindoline-5-sulfonamide

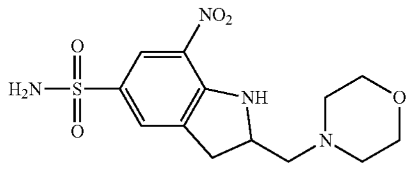 [SMILES: NS(=O)(=O)c1cc2c(c([N+](=O)[O-])c1)NC(CN1CCOCC1)C2]

Synthesis of 9,9a-dihydrooxazolo[3,4-a]indol-3 (1H)-one

To a solution of indolin-2-ylmethanol (1.0 g, 6.70 mmol) in THF (15 mL) was added CDI (1.2 g, 7.37 mmol) at 25° C. The mixture was stirred at 60'C for 3 hrs. TLC indicated reactant was consumed completely. The reaction mixture was concentrated and extracted with EtOAc. The organic layer was washed with brine, dried over $Na_2SO_4$, filtered and concentrated in vacuum. The residue was purified by column chromatography on silica gel (eluent: PE:EA=20:1 to 1:1) to give 9,9a-dihydrooxazolo[3,4-a]indol-3(1H)-one (600.0 mg, yield: 51%) as a brown solid. $^1$H NMR (400 MHz, $CDCl_3$) δ ppm: 7.47 (d, J=8.0 Hz, 1H), 7.31-7.25 (m, 1H), 7.22 (d, J=7.2 Hz, 1H), 7.13-7.08 (m, 1H), 4.89 (t, 1H), 4.82-4.74 (m, 1H), 4.32-4.22 (m, 1H), 3.33-3.24 (m, 1H), 3.29 (dd, 1H), 3.10 (dd, 1H).

Synthesis of 3-oxo-9,9a-dihydro-1H,3H-oxazolo[3,4-a]indole-7-sulfonyl chloride

A solution of 9,9a-dihydrooxazolo[3,4-a]indol-3 (1H)-one (600 mg, 3.42 mmol) in chlorosulfonic acid (6 mL) was stirred at 60° C. for 1 hr. TLC indicated reactant was consumed completely. The reaction mixture was poured into ice/$H_2O$ (20 mL) under stirring and then filtered. The filter cake was dried to give 3-oxo-1,3,9,9a-tetrahydrooxazolo[3,4-a]indole-7-sulfonyl chloride (500 mg, crude) as a yellow solid. $^1$H NMR (400 MHz, DMSO-$d_6$) δ ppm: 7.56-7.41 (d, J=7.2 Hz, 2H), 7.18 (d, J=8.4 Hz, 1H), 4.87 (m, 1H), 4.75 (m, 1H), 4.35 (m, 1H), 3.28-3.07 (m, 2H).

Synthesis of 5-nitro-3-oxo-9.9a-dihydro-1H,3H-oxazolo[3,4-a]indole-7-sulfonyl chloride To a solution of 3-oxo-1,3,9,9a-tetrahydrooxazolo[3,4-a] indole-7-sulfonyl chloride (4.3 g, 15.71 mmol) in $H_2SO_4$ (50 mL) was added $KNO_3$ (3.2 g, 31.42 mmol) at 0° C. The mixture was stirred at 0° C. for 1 hr. The mixture was poured into ice/water (300 mL) under stirring and then filtered. The filter cake was dried to give 5-nitro-3-oxo-1,3,9,9a-tetrahydrooxazolo[3,4-a]indole-7-sulfonyl chloride (4.0 g, crude) as a yellow solid. $^1$H NMR (400 MHz, DMSO-$d_4$) δ ppm: 7.91 (s, 1H), 7.81 (s, 1H), 5.05-4.95 (m, 1H), 4.82-4.79 (m, 1H), 4.46 (m, 1H), 3.38-3.23 (m, 2H).

Synthesis of (7-nitro-5-sulfamoylindolin-2-yl)methyl carbamate

To a solution of 5-nitro-3-oxo-1,3,9,9a-tetrahydrooxazolo[3,4-a]indole-7-sulfonyl chloride (500 mg, 1.57 mmol) in THF (10 mL) was added $NH_3.H_2O$ (2 mL) at 25° C. The mixture was stirred at 25° C. for 1 hr. TLC indicated reactant was consumed completely. The mixture was concentrated under reduced pressure to give (7-nitro-5-sulfamoylindolin-2-yl)methyl carbamate (500 mg, crude) as a yellow solid, which was used into the next step without further purification.

Synthesis of 2-(hydroxymethyl-7-nitroindoline-5-sulfonamide

To a solution of (7-nitro-5-sulfamoylindolin-2-yl)methyl carbamate (500 mg, 1.58 mmol) in MeOH (10 mL) was added NaOH (2.37 mL, 4.74 mmol, 2M) at 25° C. The mixture was stirred at 50° C. for 12 hrs. TLC indicated reactant was consumed completely. The reaction mixture was added water (20 mL) and extracted with DCM (10 mL). The aqueous phase was adjusted to pH=4-5 with HCl acid (1 N). The mixture was extracted with EtOAc (20 mL×4) and the organic lay was concentrated in vacuum to give 2-(hydroxymethyl)-7-nitroindoline-5- sulfonamide (400 mg, crude) as a yellow solid, 1H NMR (400 MHz, DMSO-$d_6$) δ ppm: 8.48 (s, 1H), 8.10 (s, 1H), 7.53 (s, 1H), 7.24 (s, 2H), 4.20 (m, 1H), 4.03 (m, 1H), 3.51 (m, 2H), 3.25-3.19 (m, 1H), 2.99 (m, 1H).

Synthesis of (7-nitro-5-sulfamoylindolin-2-yl)methyl methanesulfonate

To a solution of 2-(hydroxymethyl)-7-nitroindoline-5-sulfonamide (2.0 g, 7.32 mmol) in THF (50 mL) was added TEA (1.5 g, 14.64 mmol) and MsCl (1.3 g, 10.98 mmol) at 0° C. The mixture was stirred at 25° C. for 3 hrs. TLC indicated reactant was consumed completely. The reaction mixture was poured into sat. $NH_4Cl$ (100 mL) and extracted with EtOAc (100 mL×2). The organic layer was concentrated in vacuum to give (7-nitro-5-sulfamoylindolin-2-yl) methyl methanesulfonate (2.5 g, crude) as a yellow solid, which was used into the next step without further purification.

Synthesis of 2-(morpholinomethyl)-7-nitroindoline-5-sulfonamide

To a solution of (7-nitro-5-sulfamoylindolin-2-yl)methyl methanesulfonate (2.5 g, 7.12 mmol) in MeCN (25 mL) was added morpholine (6 mL) and $K_2CO_3$ (3.0 g, 21.35 mmol,) at 25° C. The mixture was stirred at 80° C. for 12 hrs. TLC indicated reactant was consumed completely. The reaction mixture was filtered and concentrated under reduced pressure. The residue was purified by column chromatography on silica gel (eluent: PE:EA=20:1 to 0:1) to give 2-(morpholinomethyl)-7-nitroindoline-5-sulfonamide (683 mg, yield: 28%) as a yellow solid. $^1$H NMR (400 MHz, DMSO-$d_6$) δ ppm: 8.30 (s, 1H), 8.12 (s, 1H), 7.61-7.52 (m, 1H), 7.25 (s, 2H), 4.36 (m, 1H), 3.57 (m, 4H), 3.28-3.18 (m, 1H), 2.98 (m, 1H), 2.61-2.56 (m, 1H), 2.44 (br s, 4H), 2.40-2.36 (m, 1H). MS (ESI, m/e) $[M+1]^+$ 343.0.

A8: 2-((1H-pyrrolo[2,3-b]pyridin-5-yl)oxy)-4-(2-((S)-2-(2-isopropylphenyl)pyrrolidin-1-yl)-7-azaspiro[3,5]nonan-7-yl)-N-((2-(morpholinomethyl)-7-nitroindolin-5-yl)sulfonyl)benzamide The mixture of (S)-2-((1H-pyrrolo[2,3-b]pyridin-5-yl)oxy)-4-(2-(2-(2-isopropylphenyl)pyrrolidin-1-yl)-7-azaspiro[3,5]nonan-7-yl)benzoic acid (188 mg, 0.33 mmol) and 2-(morpholinomethyl)-7-nitroindoline-5-sulfonamide (114 mg, 0.33 mmol), EDCI (76 mg, 0.40 mmol), DMAP (122 mg, 1.0 mmol), TEA (101 mg, 1.0 mmol) in DCM (20 mL) was heated to reflux for overnight. The reaction was quenched with a solution of AcOH in water (1/10, 50 mL), extracted with DCM (50 mL), washed with $NaHCO_3$ (aq, 100 mL), brine (50 mL), dried over $Na_2SO_4$, concentrated in vacuum. The residue was purified by column chromatography on silica gel (eluent: DCM:MeOH=50:1 to 20:1) to give a crude, which was purified by Pre-TLC (eluent: DCM: MeOH=20:1) to afford the desired compound (42 mg, 14.31%). $^1$H NMR (400 MHz, DMSO-d) δ ppm: 11.70 (s, 11H), 11.38 (s, 1H), 8.47 (s, 1H), 8.23 (s, 1H), 8.04 (s, 1H), 7.95-7.76 (m, 11H), 7.54-7.47 (m, 4H), 7.39-7.22 (m, 3H), 6.69 (d, J=8.8 Hz, 1H), 6.37 (s, 1H), 6.17 (s, 1H), 4.83-4.72 (m, 1H), 4.42-4.28 (m, 1H), 3.87-3.44 (m, 6H), 3.32-3.23 (m, 1H), 3.19-2.80 (m, 8H), 2.49-2.32 (m, 4H), 2.22-1.92 (m, 5H), 1.47-1.32 (m, 6H), 1.28-1.20 (m, 5H), 1.12 (d, J=5.6 Hz, 1H). MS (ESI, m/e) $[M+1]^+$ 890.0.

Example B1: 2-(3,4-dihydro-2H-pyrrolo[3',2':5,6]pyrido[2,3-b][1,4]oxazepin-1(7H)-yl)-N-((4-((((1r,4r)-4-hydroxy-4-methylcyclohexyl)methyl)amino)-3-nitrophenyl)sulfonyl)-4-(2-((S)-2-(2-isopropylphenyl)pyrolidin-1-yl-7-azaspiro[3,5]nonan-7-yl)benzamide

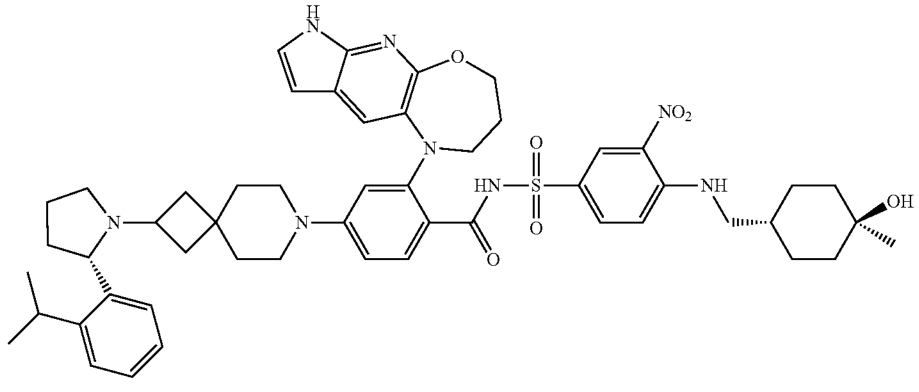 [SMILES: CC(C)c1ccccc1[C@@H]1CCCN1C1CC2(CCN(c3ccc(C(=O)NS(=O)(=O)c4ccc(NC[C@H]5CC[C@](C)(O)CC5)c([N+](=O)[O-])c4)c(N4CCCOc5nc6[nH]ccc6cc54)c3)CC2)C1]

B1-1: tert-butyl (S)-2-(2-(2-isopropylphenyl)pyrrolidin-1-yl)-7-azaspiro[3,5]nonane-7-carboxylate

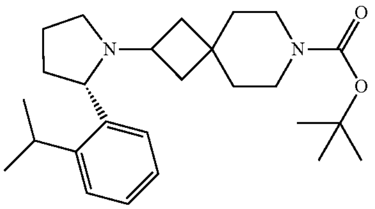 [SMILES: CC(C)c1ccccc1[C@@H]1CCCN1C1CC2(CCN(C(=O)OC(C)(C)C)CC2)C1]

To a solution of (S)-2-(2-isopropylphenyl)pyrrolidine hydrochloride (5.0, 22.7 mmol), tert-butyl 2-oxo-7-azaspiro[3,5]nonane-7-carboxylate (5.4 g, 22.7 mmol in DCM (50 mL) was added $NaBH(OAc)_3$ (14.4 g, 68 mmol). The mixture was stirred for 18 hrs at room temperature. The reaction mixture was poured into water (30 mL). The organic phase was separated and washed with brine (10 mL), dried over anhydrous $Na_2SO_4$, concentrated in vacuum to give crude product (8.5 g), which was used into the next step without further purification. MS (ESI) m/e $[M+1]^+$ 412.9.

B1-2: (S)-2-(2-(2-isopropylphenyl)pyrrolidin-1-yl)-7-azaspiro[3,5]nonane hydrochloride

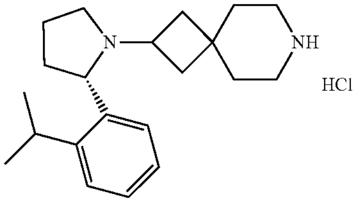 [SMILES: CC(C)c1ccccc1[C@@H]1CCCN1C1CC2(CCNCC2)C1 ; Cl]

To a solution of tert-butyl (S)-2-(2-(2-isopropylphenyl)pyrrolidin-1-yl)-7-azaspiro[3,5]nonane-7-carboxylate (8.5 g) in DCM (30 mL) was added HCl in dioxane (4 M, 20 mL). The mixture was stirred for 8 hrs at room temperature. After removing of solyent, the residue was poured into EA (20 mL) and stirred for 20 minutes at room temperature. The product (8.0 g) was collected after filtration and drying in air as solid. MS (ESI) m/e $[M+1]^+$ 312.9.

B1-3: methyl (S)-2-bromo-4-(2-(2-(2-isopropylphenyl)pyrrolidin-1-yl)-7-azaspiro[3,5]nonan-7-yl)benzoate

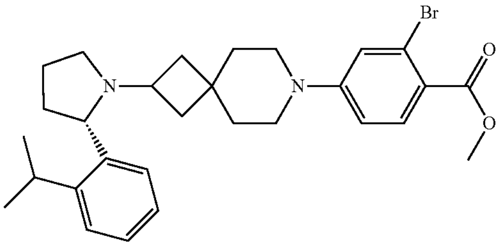 [SMILES: COC(=O)c1ccc(N2CCC3(CC2)CC(N2CCC[C@H]2c2ccccc2C(C)C)C3)cc1Br]

To a solution of (S)-2-(2-(2-isopropylphenyl)pyrrolidin-1-yl)-7-azaspiro[3,5]nonane (1.0 g, 3.0 mmol) and methyl 2-bromo-4-fluorobenzoate (660 mg, 3.0 mmol) in DMF (30 ml) was added $Na_2CO_3$ (3.0 g, 30 mmol). The mixture was stirred at 100° C. for 18 hrs under $N_2$ protection. The reaction was cooled to room temperature and then poured into water (30 mL), extracted with EA (50 mL). The organic phase was separated and washed with brine (10 mL), dried over anhydrous $Na_2SO_4$, concentrated in vacuum. The residue was purified by column chromatography on silica gel (eluent: PE:EA=10:1) to give the product 800 mg. MS (ESI, m/e) $[M+1]^+$ 524.9.

B1-4: 7-((2-(trimethylsilylethoxy)methyl)-1,3,4,7-tetrahydro-2H-pyrrolo[3',2':5,6]pyrido[2,3-b][1,4]oxazepine

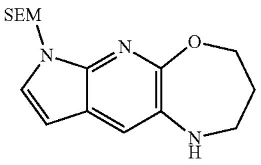 [SMILES: C[Si](C)(C)CCOCn1ccc2cc3c(nc21)OCCCN3]

Synthesis of N-(3-((5-bromo-1-((2-(trimethylsilyl)ethoxy)methyl)-1H-pyrrolo[2,3-b]pyridin-6-yl)oxy)propyl)-4-methylbenzenesulfonamide To a solution of N-(3-hydroxypropyl)-4-methylbenzenesulfonamide (5.3 g, 23.17 mmol) in THF (200 mL) was added NaH (3.7 g, 92.64 mmol) in portions at 0° C. The mixture was stirred at room temperature for 1 hour. Then to the mixture was added 5-bromo-6-fluoro-1-((2-(trimethylsilyl)ethoxy)methyl)-1H-pyrrolo[2,3-b]pyridine (4 g, 11.58 mmol). After stirred at room temperature overnight, the reaction mixture was poured into saturated aq. $NH_4Cl$ (1000 mL) and then extracted with ethyl acetate (500 mL×2). The combined organic phase was washed with brine, dried over anhydrous $Na_2SO_4$, concentrated in vacuum. The residue was purified by column chromatography on silica gel (eluent: PE:EA=10:1 to 4:1) to give the product 2.6 g. MS (ESI, m/e) $[M+1]^+$ 553.8.

Synthesis of 1-tosyl-7-((2-(trimethylsilyl)ethoxy)methyl)-1,3,4,7-tetrahydro-2H-pyrrolo[3',2':5.6]pyrido[2,3-b][1,4]oxazepane To a solution of N-(3-((5-bromo-1-((2-(trimethylsilyl)ethoxy)methyl)-1H-pyrrolo[2,3-b]pyridin-6-yl)oxy)propyl)-4-methylbenzenesulfonamide (2.52 g, 4.55 mmol) in DMSO (50 mL) were added picolinic acid (449 mg, 3.65 mmol), CuI (1.04 g, 5.46 mmol), $K_2CO_3$ (1.88 g, 13.65 mmol). The mixture was stirred at 140° C. for 5 hours. The reaction mixture was cooled to room temperature and then diluted with EA (200 mL), washed with brine, dried over anhydrous $Na_2SO_4$, concentrated in vacuum. The residue was purified by column chromatography on silica gel (eluent: PE:EA=10:1 to 4:1) to give the product 950 mg. MS (ESI, m/e) $[M+1]^+$ 473.9.

Synthesis of 7-((2-(trimethylsilyl)ethoxy)methyl)-1,3,4,7-tetrahydro-2H-pyrrolo[3',2':5.6]pyrido[2,3-b][1,4]oxazepane (B1-4)

To a solution of 1-tosyl-7-((2-(trimethylsilyl)ethoxy)methyl)-1,3,4,7-tetrahydro-2H-pyrrolo[3',2':5,6]pyrido[2,3-b][1,4]oxazepine (950 mg, 2 mmol) in MeOH (20 mL) was added Mg powder (10 g, 411 mmol). The mixture was stirred at reflux for 1 hour. The mixture was poured into saturated aq. $NH_4Cl$ (100 mL), extracted with EA (100 ml). The organic phase was washed with brine, dried over anhydrous $Na_2SO_4$, concentrated in vacuum. The residue was purified by column chromatography on silica gel (eluent: PE:EA=2:1) to give the product 550 mg. MS (ESI, m/e) $[M+1]^+$ 320.0.

B1-5: methyl (S)-4-(2-(2-(2-isopropylphenyl)pyrrolidin-1-yl)-7-azaspiro[3,5]nonan-7-yl)-2-(7-((2-(trimethylsilyl)ethoxyl)methyl)-3,4-dihydro-2H-pyrrolo[3',2':5,6]pyrido[2,3-b][1,4]oxazinin-1(7H)-yl)benzoate

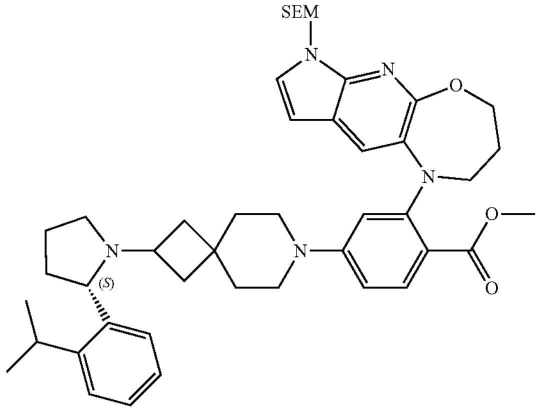

To a solution of 7-((2-(trimethylsilyl)ethoxy)methyl)-1,3,4,7-tetrahydro-2H-pyrrolo[3',2':5,6]pyrido[2,3-b][1,4]oxazepane (250 mg, 0.783 mmol) in toluene (30 ml) was added methyl (S)-2-bromo-4-(2-(2-(2-isopropylphenyl)pyrrolidin-1-yl)-7-azaspiro[3,5]nonan-7-yl)benzoate (616.8 mg, 1.17 mmol), $Cs_2CO_3$ (763 mg, 2.349 mmol), Xant Phos G2 (347 mg, 0.392 mmol). The mixture was stirred at 120° C. for 2 days under $N_2$ protection. The reaction mixture was cooled to room temperature and washed with brine, dried over anhydrous $Na_2SO_4$, concentrated in vacuum. The residue was purified by column chromatography on silica gel (eluent: PE:EA=2:1) to give the product 390 mg (yield: 65%). MS (ESI, m/e) $[M+1]^+$ 764.3.

B1-6: methyl (S)-2-(3,4-dihydro-2H-pyrrolo[3',2':5,6]pyrido[2,3-b][1,4]oxazepin-1(7H)-yl)-4-(2-(2-(2-isopropylphenyl)pyrrolidin-1-yl)-7-azaspiro[3,5]nonan-7-yl)benzoate

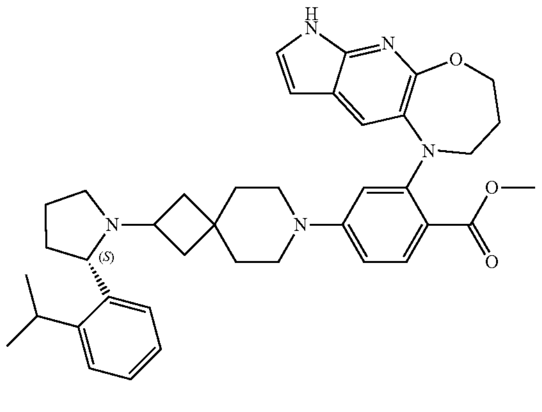

To a solution of methyl (S)-4-(2-(2-(2-isopropylphenyl)pyrrolidin-1-yl)-7-azaspiro[3,5]nonan-7-yl)-2-(7-((2-(trimethylsilyl)ethoxy)methyl)-3,4-dihydro-2H-pyrrolo[3',2':5,6]pyrido[2,3-b][1,4]oxazepin-1(7H)-yl)benzoate (390 mg, 0.615 mmol) in THF (10 mL) was added TBAF (15 mL) (1M in THF solution) and ethane-1,2-diamine (10 mL). The mixture was stirred at 70° C. for overnight. The mixture was cooled to room temperature and then diluted with EA (100 ml), washed with brine, dried over anhydrous $Na_2SO_4$, concentrated in vacuum. The residue was purified by column chromatography on silica gel (eluent: PE:EA=1:2 to 1:4) to give the product 250 mg (yield: 64%). MS (ESI, m/e) $[M+1]^+$ 634.5.

B1-7: (S)-2-(3,4-dihydro-2H-pyrrolo[3',2':5,6]pyrido[2,3-b][1.4]oxazepin-1(7H)-yl)-4-(2-(2-(2-isopropylphenyl)pyrrolidin-1-yl)-7-azaspiro[3,5]nonan-7-yl) benzoic aid

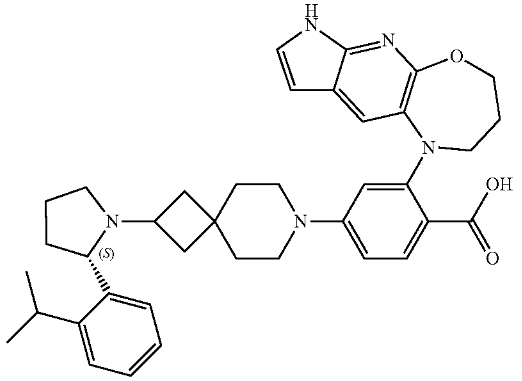

To a solution of methyl (S)-2-(3,4-dihydro-2H-pyrrolo[3',2':5,6]pyrido[2,3-b][1,4]oxazepin-1(7H)-yl)-4-(2-(2-(2-isopropylphenyl)pyrrolidin-1-yl)-7-azaspiro[3,5]nonan-7-yl) benzoate (250 mg, 0.394 mmol) in THF (6 mL) and MeOH (6 mL) was added 6N NaOH solution in water (6 mL). The mixture was stirred at 60° C. for overnight. The reaction mixture was cooled to room temperature and adjusted to PH=5 with 1N HCl acid, extracted with DCM (100 mL). The organic phase was washed with brine, dried over anhydrous $Na_2SO_4$, concentrated in vacuum to give the product 220 mg (crude). MS (ESI, m/e) $[M+1]^+$ 620.4. 2-(3,4-dihydro-2H-pyrrolo[3',2':5,6]pyrido[2,3-b][1,4]oxazepin-1(7H)-yl)-N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3,5]nonan-7-yl)benzamide (example B1)

To a solution of (S)-2-(3,4-dihydro-2H-pyrrolo[3',2':5,6]pyrido[2,3-b][1,4]oxazepin-1(7H)-yl)-4-(2-(2-(2-isopropylphenyl)pyrrolidin-1-yl)-7-azaspiro[3,5]nonan-7-yl)benzoic acid (80 mg, 0.129 mmol) in DCM (20 ml) was added 4-((((1R,4R)-4-hydroxy-4-methylcyclohexyl)methyl)amino)-3-nitrobenzenesulfonamide (66 mg, 0.1935 mmol), EDCI (49 mg, 0.258 mmol), DMAP (63 mg, 0.516 mmol) and TEA (26 mg, 0.258 mmol). The mixture was stirred at room temperature for overnight. The mixture was evaporated in vacuum. The residue was purified by prep-HPLC to give the product 12 mg (yield: 9.8%).

$^1H$ NMR (400 MHz, DMSO-$d_6$) δ ppm: 11.91 (s, 1H), 11.30 (s, 1H), 10.43 (s, 1H), 8.56-8.48 (m, 11H), 8.46 (d, J=2.2 Hz, 11H), 7.97-7.78 (m, 1H), 7.63-7.55 (m, 1H), 7.48 (d, J=8.9 Hz, 11H), 7.44-7.15 (m, 4H), 6.90 (s, 1H), 6.88-

6.80 (m, 2H), 6.78-6.66 (m, 2H), 6.12 (s, 11H), 4.87-4.68 (m, 11H), 4.26 (s, 11H), 4.24-4.15 (m, 2H), 4.01-3.85 (m, 11H), 3.78-3.61 (m, 1H), 3.57-3.49 (m, 2H), 3.26-3.20 (m, 3H), 3.15-3.03 (m, 3H), 2.22-2.06 (m, 4H), 2.04-1.93 (m, 3H), 1.74-1.25 (m, 19H), 1.16-1.11 (m, 4H), 1.11-1.08 (s, 3H). MS (ESI, m/e) $[M+1]^+$ 944.9.

Example B2: (S)-2-(3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)-4-(2-(2-(2-isopropylphenyl) pyrrolidin 1-yl)-7-azaspiro[3,5]nonan-7-yl) benzamide

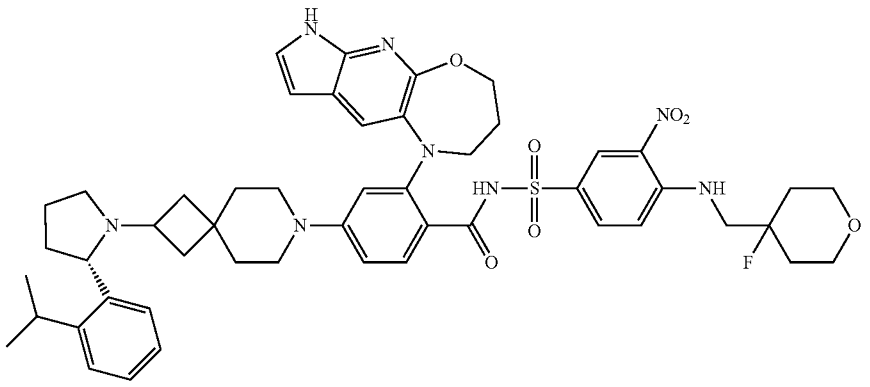 [SMILES: CC(C)c1ccccc1[C@@H]1CCCN1C1CC2(CCN(c3ccc(C(=O)NS(=O)(=O)c4ccc(NCC5(F)CCOCC5)c([N+](=O)[O-])c4)c(N4CCCOc5nc6[nH]ccc6cc54)c3)CC2)C1]

The desired compound was synthesized with (2-isopropylphenyl)pyrrolidin-1-yl)-7-azaspiro[3,5]nonan-7-yl)benzoic acid and 4-(((4-fluorotetrahydro-2H-pyran-4-yl) methyl)amino)-3-nitrobenzenesulfonamide following the similar procedure of B1. $^1$H NMR (400 MHz, DMSO-$d_4$) δ ppm: 11.93 (s, 1H), 11.26 (s, 1H), 10.38 (s, 1H), 8.64-8.53 (m, 11H), 8.52-8.38 (m, 11H), 7.95-7.75 (m, 1H), 7.67-7.60 (m, 1H), 7.52-7.44 (m, 1H), 7.44-7.10 (m, 5H), 7.10-7.00 (m, 1H), 6.90 (s, 1H), 6.80-6.65 (m, 2H), 6.20-6.05 (m, 1H), 4.95-4.70 (m, 1H), 4.30-4.10 (m, 2H), 3.99-3.85 (m, 1H), 3.85-3.59 (m, 5H), 3.59-3.44 (m, 4H), 3.25-2.92 (m, 6H), 2.48-2.36 (m, 1H), 2.24-1.90 (m, 7H), 1.90-1.67 (m, 5H), 1.60-1.35 (m, 7H), 1.17-1.07 (m, 3H). MS (ESI, m/e) [M+1]934.9.

Example B3: 2-(2,3-dihydropyrrolo[3',2':56]pyrido [2,3-b][1,4]oxazin-1(6H)-yl)-N-((4-((((1r,4r)-4-hydroxy-4-methylcyclohexyl)methyl)amino)-3-nitrophenyl)sulfonyl)-4-(2-((S)-2-(2-isopropylphenyl) pyrrolidin-1-yl)-7-azaspiro[3,5]nonan-7-yl) benzamide

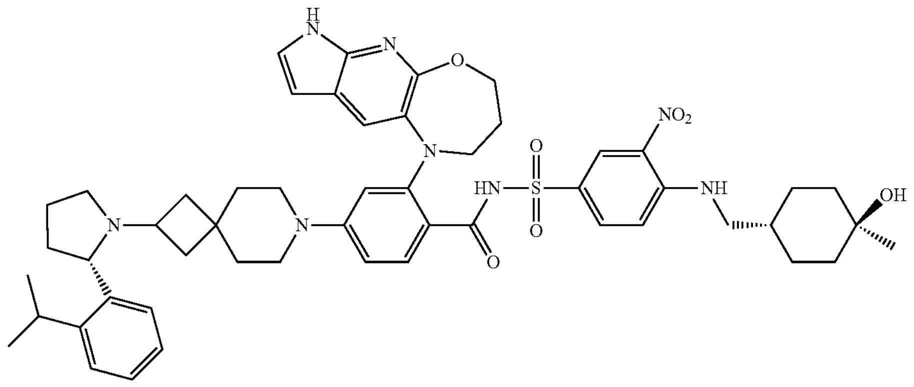 [SMILES: CC(C)c1ccccc1[C@@H]1CCCN1C1CC2(CCN(c3ccc(C(=O)NS(=O)(=O)c4ccc(NC[C@H]5CC[C@](C)(O)CC5)c([N+](=O)[O-])c4)c(N4CCCOc5nc6[nH]ccc6cc54)c3)CC2)C1]

B3-1: 6-((2-(trimethylsilyl)ethoxy)methyl)-1,2,3,6-tetrahydropyrrolo[3',2':5,6]pyrido[2,3b][1,4]oxazine

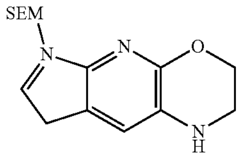

Synthesis of 5-bromo-6-fluoro-1-((2-(trimethylsilyl)ethoxy)methyl)-1H-pyrrolo[2,3-b]pyridine To a solution of 5-bromo-6-fluoro-1H-pyrrolo[2,3-b]pyridine (5.0 g, 23.2 mmol) in DMF (50 ml) at 0° C. was added NaOH (1400 mg, 34.8 mmol) portion wise. The mixture was stirred at 0° C. for 1 hour. Then (2-(chloromethoxy)ethyl)trimethylsilane (4.6 g, 28 mmol) was added to the mixture drop wise. The reaction mixture was stirred at 20° C. for 4 hours. The reaction mixture was concentrated in vacuum and purified by chromatography column on silica gel (eluent: PE:EA=20:1) to give the target product 5.0 g. MS (ESI, m/e) $[M+1]^+$ 499.9.

Synthesis of N-(6-(tert-butoxy)-1-((2-(trimethylsilyl)ethoxy)methyl)-1H-pyrrolo[2,3-b]pyridin-5-yl)-1,1-diphenylmethanimine To a mixture of 5-bromo-6-fluoro-1-((2-(trimethylsilyl)ethoxy)methyl)-1H-pyrrolo[2,3-b]pyridine (3.0 g, 8.7 mmol), diphenylmethanimine (1.88 g 10.4 mmol), $Pd_2(dba)_3$ (800 mg 0.87 mmol), t-BuOK (3.18 g, 26.1 mmol) in dioxane (40 mL) was added xantphos (924 mg, 1.6 mmol). The mixture was stirred at 100° C. for 18 hours under $N_2$ atmosphere. The reaction mixture was cooled to room temperature and filtered. The filtrate was concentrated and purified by chromatography column on silica gel (eluent: PE:EA=60:1 to 20:1) to obtain the target product 3.0 g. MS (ESI, m/e) $[M+1]^+$ 499.9.

Synthesis of 5-amino-1-((2-(trimethylsilyl)ethoxy)methyl)-1H-pyrrolo[2,3-b]pyridin-6-ol To a solution of N-(6-(tert-butoxy)-1-((2-(trimethylsilyl)ethoxy)methyl)-1H-pyrrolo[2,3-b]pyridin-5-yl)-1,1-diphenylmethanimine (6.0 g, 12 mmol) in dioxane (40 ml) was added HCl in dioxane (9 mL, 4M). The mixture was stirred at 0° C. for 4 hours. The reaction mixture was quenched with sat. aq. $Na_2CO_3$ (30 mL) and then diluted with $H_2O$ (30 mL) and EA (50 mL). The organic phase was separated and washed with brine (10 mL), dried over $Na_2SO_4$, concentrated and purified by chromatography column on silica gel (eluent: DCM:MeOH=50:1) to give the target product 1.3 g. 1H NMR (400 MHz, DMSO-d) δ ppm: 6.97 (s, 1H), 6.94 (s, 1H), 6.12 (s, 1H), 5.38 (s, 2H), 4.42 (br, 1H), 3.48-3.36 (m, 2H), 0.84-0.71 (m, 2H), 0.65-0.13 (m, 9H). MS (ESI, m/e) $[M+1]^+$ 279.9.

Synthesis of ethyl 2-((5-amino-1-((2-(trimethylsilyl)ethoxy)methyl)-1H-pyrrolo[2,3-b]pyridin-6-yl)oxy)acetate To a solution of 5-amino-1-((2-(trimethylsilyl)ethoxy)methyl)-1H-pyrrolo[2,3-b]pyridin-6-ol (1400 mg, 5.0 mmol) and ethyl 2-bromoacetate (835 mg, 5.0 mmol) in $CH_3CN$ (50 mL) was added $CS_2CO_3$ (2.4 g, 7.5 mmol). The mixture was stirred at 70° C. for 4 hours under $N_2$ protection. The reaction mixture was concentrated and $H_2O$ (30 mL) and EA (50 mL) was added into the resulting residue under stirring. The organic phase was separated and washed with brine (10 mL), dried over $Na_2SO_4$, concentrated and purified by chromatography column on silica gel (eluent: PE:EA=3:1) to obtain the target product 750 mg. MS (ESI, m/e) $[M+1]^+$ 365.9.

Synthesis of 6-((2-(trimethylsilyl)ethoxy)methyl)-1,6-dihydropyrrolo[3',2':5,6]pyrido[2,3-b][1,4]oxazin-2(3H)-one To a solution of ethyl 2-((5-amino-1-((2-(trimethylsilyl)ethoxy)methyl)-1H-pyrrolo[2,3-b]pyridin-6-yl)oxy)acetate (750 mg, 2.0 mmol) in EtOH (20 mL) was added $CS_2CO_3$ (1.3 g, 4 mmol). The mixture was stirred at 90° C. for 18 hours under $N_2$ protection. The reaction was cooled and quenched with $H_2O$ (30 mL) and then was extracted with EA (50 ml×2). The organic phase was washed with brine (10 mL), dried over $Na_2SO_4$, concentrated and purified by chromatography column on silica gel (eluent: PE:EA=3:1) to give the target product 300 mg. $^1H$ NMR (400 MHz, DMSO-$d_6$) δ ppm: 10.73 (s, 1H), 7.47-7.38 (m, 2H), 6.43 (d, J=3.3 Hz, 1H), 5.46 (s, 2H), 4.72 (s, 2H), 3.48 (t, J=7.9 Hz, 2H), 0.81 (t, J=7.9 Hz, 3H), 0.69 (s, 9H). MS (ESI, m/e) $[M+1]^+$ 319.9.

Synthesis of 6-((2-(trimethylsilyl)ethoxy)methyl)-1,2,3,6-tetrahydropyrrolo[3',2':5,6]pyrido[2,3-b][1,4]oxazine To a solution of 6-((2-(trimethylsilyl)ethoxy)methyl)-1,6-dihydropyrrolo[3',2':5,6]pyrido[2,3-b][1,4]oxazin-2(3H)-one (300 mg, 0.65 mmol) in THF (5 mL) was added BH3 (3 mL, 2M in THF). The mixture was stirred at room temperature for 4 hours under $N_2$ protection. The reaction was quenched with $H_2O$ (30 mL) and was extracted with EA (50 mL×2). The organic phase was washed with brine (10 mL), dried over $Na_2SO_4$, concentrated and purified by chromatography column on silica gel (eluent: PE:EA=3:1) to give the target product 150 mg. MS (ESI, m/e) $[M+1]^+$ 306.0.

B3-2: methyl (S)-4-(2-(2-(2-isopropylphenyl)pyrrolidin-1-yl)-7-azaspiro[3,5]nonan-7-yl)-2-(6-((2-(trimethylsilyl)ethoxydimethyl)-2,3-dihydropyrrolo[3',2':5,6]pyrido[2,3-b][1,4]oxazin-1(6H)-yl)benzoate

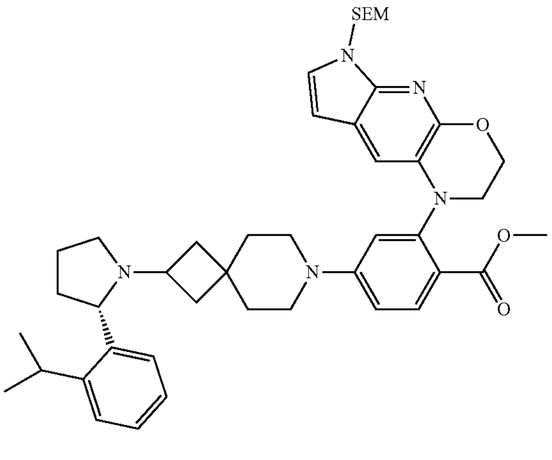 [SMILES: COC(=O)c1ccc(N2CCC3(CC2)CC(N2CCC[C@H]2c2ccccc2C(C)C)C3)cc1N1CCOc2nc3c(ccn3COCC[Si](C)(C)C)cc21]

B3-2 was synthesized following the similar procedure of B1-5 by replacing 7-((2-(trimethylsilyl)ethoxy)methyl)-1,3,4,7-tetrahydro-2H-pyrrolo[3',2':5,6]pyrido[2,3-b][1,4]oxazepane with 6-((2-(trimethylsilyl)ethoxy)methyl)-1,2,3,6-tetrahydropyrrolo[3',2':5,6]pyrido[2,3-b][1,4]oxazine. MS (ESI, m/e) $[M+1]^+$ 750.2.

B3-3: methyl (S)-2-(2,3-dihydropyrrolo[3',2':5,6]pyrido[2,3-b][1,4]oxazin-1(6H)-yl)-4-(2-(2-(2-isopropylphenyl)pyrrolidin-1-yl)-7-azaspiro[3,5]nonan-7-yl)benzoate

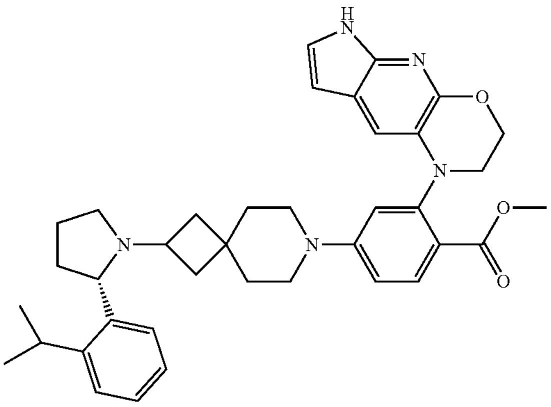 [SMILES: COC(=O)c1ccc(N2CCC3(CC2)CC(N2CCC[C@H]2c2ccccc2C(C)C)C3)cc1N1CCOc2nc3[nH]ccc3cc21]

B3-3 was synthesized following the similar procedure of B1-6. MS (ESI, m/e) $[M+1]^+$ 620.3.

B3-4: (S)-2-(2,3-dihydropyrrolo[3',2':5,6]pyrido[2,3-b][1,4]oxazin-1(6H)-yl)-4-(2-(2-(2-isopropylphenyl)pyrrolidin-1-yl)-7-azaspiro[3,5]nonan-7-yl)benzoic acid

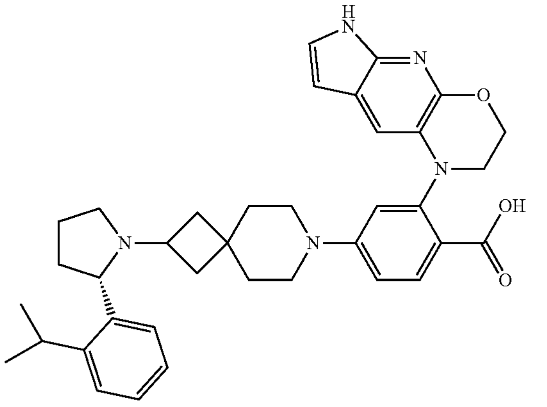 [SMILES: CC(C)c1ccccc1[C@@H]1CCCN1C1CC2(CCN(c3ccc(C(=O)O)c(N4CCOc5nc6[nH]ccc6cc54)c3)CC2)C1]

B3-4 was synthesized following the similar procedure of B1-7. MS (ESI, m/e) $[M+1]^+$ 606.2.

B3: 2-(2,3-dihydropyrrolo[3',2':5,6]pyrido[2,3-b][1.4]oxazin-1(6H)-yl)-N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3,5]nonan-7-yl)benzamide The desired compound was synthesized with (2-isopropylphenyl)pyrrolidin-1-yl)-7-azaspiro[3,5]nonan-7-yl)benzoic acid and 4-((((1R,4R)-4-hydroxy-4-methylcyclohexyl)methyl)amino)-3-nitrobenzenesulfonamide following the similar procedure of B1.

$^1$H NMR (400 MHz, DMSO-$d_6$) δ ppm: 12.18 (s, 1H), 11.02 (s, 1H), 8.48 (s, 1H), 8.35 (s, 1H), 7.57-7.54 (m, 2H), 7.32 (s, 2H), 7.20 (s, 1H), 7.12 (s, 1H), 7.01 (s, 1H), 6.81 (s, 1H), 6.74-6.71 (m, 2H), 6.58 (s, 1H), 5.98-5.92 (m, 1H), 4.44 (s, 2H), 4.25 (s, 1H), 3.59-3.56 (m, 3H), 3.31 (s, 2H), 3.22 (s, 3H), 3.16 (s, 2H), 3.09-3.07 (m, 3H), 2.17 (s, 1H), 1.77 (s, 2H), 1.69-1.67 (m, 2H), 1.57-1.54 (m, 3H), 1.45 (s, 2H), 1.39-1.37 (m, 3H), 1.35-1.33 (m, 1H), 1.23 (s, 3H), 1.18-1.12 (m, 7H), 1.10 (s, 3H). MS (ESI) m/e $[M+1]^+$ 930.9.

Example B4: (S)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)-4-(2-(2-(2-isopropylphenyl)pyrrolidin-1-yl)-7-azaspiro[3,5]nonan-7-yl)benzamide

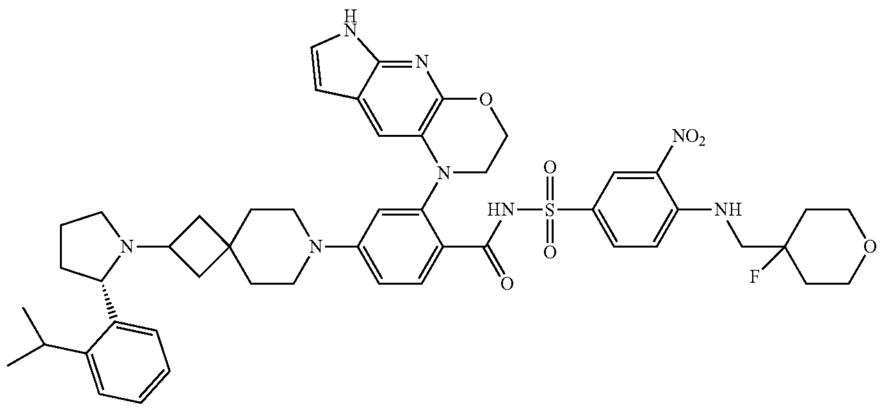 [SMILES: CC(C)c1ccccc1[C@@H]1CCCN1C1CC2(CCN(c3ccc(C(=O)NS(=O)(=O)c4ccc(NCC5(F)CCOCC5)c([N+](=O)[O-])c4)c(N4CCOc5nc6[nH]ccc6cc54)c3)CC2)C1]

The desired compound was synthesized with (S)-2-(2,3-dihydropyrrolo[3',2':5,6]pyrido[2,3-b][1,4]oxazin-1(6H)-yl)-4-(2-(2-(2-isopropylphenyl)pyrrolidin-1-yl)-7-azaspiro[3,5]nonan-7-yl)benzoic acid and 4-(((4-fluorotetrahydro-2H-pyran-4-yl)methyl)amino)-3-nitrobenzenesulfonamide following the similar procedure of Example B1. $^1$H NMR (400 MHz, DMSO-$d_6$) δ ppm: 12.18 (s, 1H), 11.02 (s, 11H), 10.36 (s, 1H), 8.57 (s, 1H), 8.37 (s, 1H), 7.84 (s, 11H), 7.56 (d, J=8.8 Hz, 1H), 7.38-7.36 (m, 4H), 7.03 (s, 1H), 6.86-6.84 (m, 2H), 6.73 (s, 11H), 6.58 (s, 1H), 5.94 (s, 1H), 4.77 (s, 1H), 4.45 (s, 2H), 3.89 (s, 1H), 3.81-3.47 (m, 11H), 3.15-3.12 (m, 6H), 2.19-1.99 (m, 5H), 1.82-1.80 (m, 5H), 1.49-1.32 (m, 7H), 1.13-1.12 (m, 4H). MS (ESI) m/e $[M+1]^+$ 922.3.

Example B5: N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3,5]nonan-7-yl)-2-((R)-3-methyl-2,3-dihydropyrrolo[3',2':5,6]pyrido[2,3-b][1,4]oxazin-1(6H)-yl)benzamide give (R)-tert-butyl (2-hydroxypropyl)carbamate (50 g, crude), which was used directly for next step.

Synthesis of (R)-tert-butyl (2-((5-bromo-1-((2-(trimethylsilyl)ethoxy)methyl)-1H-pyrrolo[2,3-b]pyridin-6-yl)oxy)propyl)carbamate To a solution of 5-bromo-6-fluoro-1-((2-(trimethylsilyl)ethoxy)methyl)-1H-pyrrolo[2,3-b]pyridine (20 g, 57.82 mmol) in THF (200 mL) was added (R)-tert-butyl (2-hydroxypropyl)carbamate (15 g, 86.89 mmol) and NaH (9.27 g, 231.69 mmol). The mixture was stirred at 25° C. for 12 hrs. TLC indicated reactant was consumed completely. The mixture was poured into aq. $NH_4Cl$ solution (1M, 100 mL) and extracted with EA (200 mL×3). The combined organic layers were dried over anhydrous $Na_2SO_4$, filtered and concentrated in vacuum. The residue was purified by column chromatography on silica gel (eluent: PE:EA=20:1 to 5:1) to give (R)-tert-butyl (2-((5-bromo-1-((2-(trimethylsilyl)ethoxy) methyl)-1H-pyrrolo[2,3-b]pyridin-6-yl)oxy)propyl) carbamate (2.2 g, yield: 7.8%). MS (ESI, m/e) [M+1] 500.2.

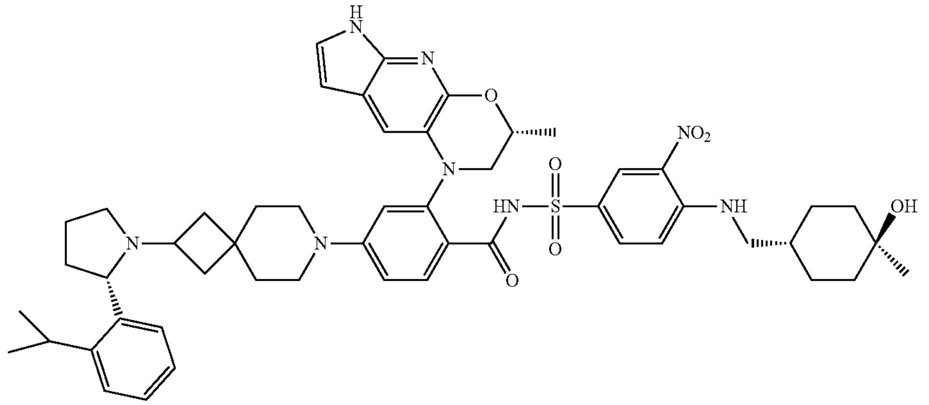 [SMILES: CC(C)c1ccccc1[C@@H]1CCCN1C1CC2(CCN(c3ccc(C(=O)NS(=O)(=O)c4ccc(NC[C@H]5CC[C@](C)(O)CC5)c([N+](=O)[O-])c4)c(N4C[C@@H](C)Oc5nc6[nH]ccc6cc54)c3)CC2)C1]

B5-1: (R)-3-methyl-6-((2-(trimethylsilyl)ethoxy)methyl)-1,2,3,6-tetrahydropyrrolo[3,2':5,6]pyrido[2,3-b][1,4]oxazine

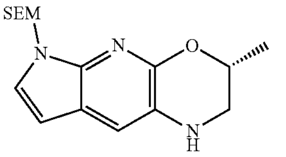 [SMILES: C[C@@H]1CNc2cc3ccn(COCC[Si](C)(C)C)c3nc2O1]

Synthesis of (R)-tert-butyl (2-hydroxypropyl)carbamate

To a solution of (R)-1-aminopropan-2-ol (25 g, 332.85 mmol) in DCM (250 mL) was added $Boc_2O$ (87.17 g, 399.42 mmol) and TEA (50.52 g, 499.27 mmol) at 25° C. The mixture was stirred at 25° C. for 16 hrs. TLC indicated reactant was consumed completely. The mixture was quenched with water, and then extracted with DCM (200 mL×2). The organic layer was dried, filtered and concentrated in vacuum. The residue was purified by column chromatography on silica gel (eluent: PE:EA=5:1 to 1:1) to Synthesis of (R)-tert-butyl 3-methyl-6-((2-(trimethylsilylethoxy)methyl)-2,3-dihydropyrrolo[3',2':5,6]pyrido[2,3-b][1.4]oxazine-1(6H)-carboxylate To a solution of (R)-tert-butyl (2-((5-bromo-1-((2-(trimethylsilyl)ethoxy)methyl)-1H-pyrrolo[2,3-b]pyridin-6-yl)oxy)propyl)carbamate (2.2 g, 4.40 mmol) in toluene (40 mL) was added Xphos (419 mg, 879.12 umol), t-BuONa (844.86 mg, 8.79 mmol) and $Pd_2$(dba), (402.51 mg, 439.56 umol) under Argon (glove box). The mixture was stirred at 90'C for 12 hrs. TLC indicated reactant was consumed completely. The reaction mixture was cooled to room temperature and then diluted with $H_2O$ (50 mL), extracted with EA (50 mL×2). The combined organic layers were dried over anhydrous $Na_2SO_4$, filtered and concentrated in vacuum. The residue was purified by column chromatography on silica gel (eluent: PE:EA=20:1 to 5:1) to give (R)-tert-butyl 3-methyl-6-((2-(trimethylsilyl)ethoxy)methyl)-2,3-dihydropyrrolo[3',2':5,6]pyrido[2,3-b][1,4]oxazine-1(6H)-carboxylate (940 mg, yield: 52%). MS (ESI, m/e) $[M+1]^+$ 420.2.

(R)-3-methyl-6-((2-(trimethylsilylethoxy)methyl-1,2,3,6-tetrahydropyrrolo[3',2':5,6]pyrido[2,3-b][1,4]oxazine To a solution of (R)-tert-butyl 3-methyl-6-((2-(trimethylsilyl)ethoxy)methyl)-2,3-dihydropyrrolo[3',2':5,6]pyrido[2, 3-b][1,4]oxazine-1(6H)-carboxylate (940 mg, 2.24 mmol) in DCM (20 mL) was added ZnBr2 (1.51 g, 6.72 mmol) at 25° C. The mixture was stirred at 25° C. for 12 hrs. TLC indicated the reactant was consumed completely. The reaction mixture was diluted with EA (50 mL) and then poured into aq. $Na_2CO_3$ solution (20 mL). The organic layer was separated and the aqueous layer was extracted with EA (50 mL×2). The combined organic layers were dried over anhydrous $Na_2SO_4$, filtered and concentrated in vacuum. The residue was purified by column chromatography on silica gel (eluent: PE:EA=20:1 to 5:1) to give (R)-3-methyl-6-((2-(trimethylsilyl)ethoxy)methyl)-1,2,3,6-tetrahydropyrrolo[3',2':5,6] pyrido[2,3-b][1,4]oxazine (530 mg, yield: 74%) as a solid. $^1$H NMR (400 MHz, $CDCl_3$) δ ppm: 7.16 (s, 1H), 7.11 (d, J=3.2 Hz, 1H,), 6.29 (d, J=3.6 Hz, 1H), 5.55 (s, 2H), 4.47 (s, 1H), 3.72 (br, 1H), 3.57-3.48 (m, 2H), 3.36 (dd, J=11.6, 2.4 Hz, 1H), 3.12 (dd, J=11.6, 8.0 Hz, 1H), 1.47 (d, J=6.0 Hz, 3H), 0.92-0.85 (m, 2H), 0.25-0.06 (s, 9H). MS (ESI, m/e) $[M+1]^+$ 320.3.

B5-2: Methyl 4-(2-((S)-2-(2-isopropylphenyl)pyrrolidin-1-yl)-7-azaspiro[3,5]nonan-7-yl)-2-((R)-3-methyl-6-((2-(trimethylsilyl)ethoxy)methyl)-2,3-dihydropyrrolo[3',2':5,6]pyrido[2,3-b][1,4]oxazin-1(6H)-yl)benzoate

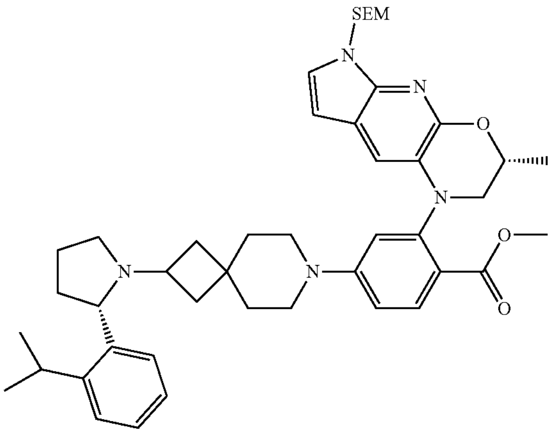 [SMILES: COC(=O)c1ccc(N2CCC3(CC2)CC(N2CCC[C@H]2c2ccccc2C(C)C)C3)cc1N1C[C@@H](C)Oc2nc3c(ccn3COCC[Si](C)(C)C)cc21]

To a solution of methyl (S)-2-bromo-4-(2-(2-(2-isopropylphenyl)pyrrolidin-1-yl)-7-azaspiro[3,5]nonan-7-yl)benzoate (800 mg, 1.8 mmol) and (R)-3-methyl-6-((2-(trimethylsilyl)ethoxy)methyl)-1,2,3,6-tetrahydropyrrolo[3',2':5,6] pyrido[2,3-b][1,4]oxazine (400 mg, 1.25 mmol), $CS_2CO_3$ (1.5 g, 5 mmol), in dioxane (30 mL) was added xantphos Pd G2 (60 mg). The mixture was stirred at 110° C. for overnight under $N_2$ protection. The reaction was cooled to r,t and quenched with $H_2O$ (30 mL). The mixture was extracted with EA (50 mL×2) and the organic phase was washed with brine (10 mL), dried over $Na_2SO_4$, concentrated in vacuum. The residue was purified by column chromatography on silica gel (eluent: PE:EA=5:1) to give B5-2 (1.0 g). MS (ESI, m/e) $[M+1]^+$ 763.9.

B5-3: methyl 2-((R)-6-(hydroxymethyl)-3-methyl-2,3-dihydropyrrolo[3',2':5,6]pyrido[2,3-b][1,4]oxazin-1(6H)-yl)-4-(2-((S)-2-(2-isopropylphenyl)pyrrolidin-1-yl)-7-azaspiro[3,5]nonan-7-yl)benzoate

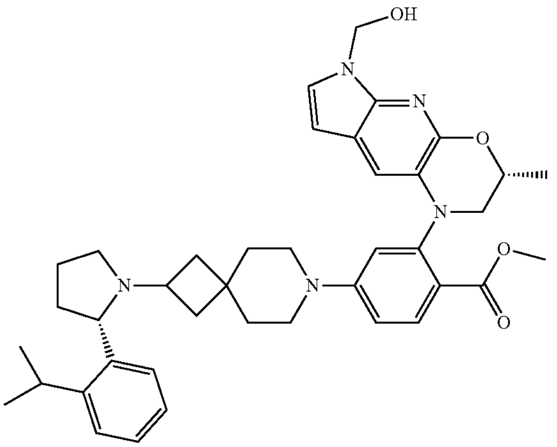 [SMILES: COC(=O)c1ccc(N2CCC3(CC2)CC(N2CCC[C@H]2c2ccccc2C(C)C)C3)cc1N1C[C@@H](C)Oc2nc3c(ccn3CO)cc21]

To a solution of methyl 4-(2-((S)-2-(2-isopropylphenyl)pyrrolidin-1-yl)-7-azaspiro[3,5]nonan-7-yl)-2-((R)-3-methyl-6-((2-(trimethylsilyl)ethoxy)methyl)-2,3-dihydropyrrolo[3',2':5,6]pyrido[2,3-b][1,4]oxazin-1(6H)-yl) benzoate (1.0 g, 1.3 mmol) in DCM (50 ml) was added TFA (5 mL). The mixture was stirred at r,t for 2 hrs and then was poured into saturated aq. $NaHCO_3$ (30 mL). The organic phase was separated and washed with brine (10 mL), dried over $Na_2SO_4$, concentrated in vacuum. The residue was purified by column chromatography on silica gel (eluent: PE:EA=3:1) to obtain B5-3 (900 mg). MS (ESI, m/e) $[M+1]^+$ 663.9.

B5-4: methyl 4-(2-((S)-2-(2-isopropylphenyl)pyrrolidin-1-yl)-7-azaspiro[3,5]nonan-7-yl)-2-((R)-3-methyl-2,3-dihydropyrrolo[3',2':5,6]pyrido[2,3-b][1,4]oxazin-1(6H-yl)benzoate

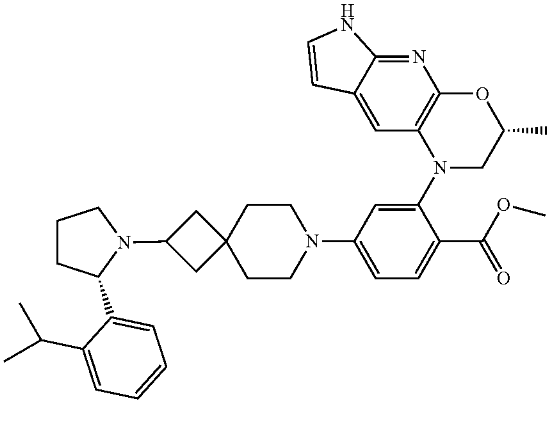 [SMILES: COC(=O)c1ccc(N2CCC3(CC2)CC(N2CCC[C@H]2c2ccccc2C(C)C)C3)cc1N1C[C@@H](C)Oc2nc3[nH]ccc3cc21]

To a solution of methyl 2-((R)-6-(hydroxymethyl)-3-methyl-2,3-dihydropyrrolo[3',2':5,6]pyrido[2,3-b][1,4]oxazin-1(6H)-yl)-4-(2-((S)-2-(2-isopropylphenyl)pyrrolidin-1-yl)-7-azaspiro[3,5]nonan-7-yl)benzoate (900 mg, 1.35 mmol) in MeOH (20 mL) was added $K_2CO_3$ (375 mg, 2.7 mmol). The mixture was stirred at r,t for 2 hrs. The reaction was poured into water (30 mL) and extracted with DCM (60 mL×2). The combined organic phase was washed with brine (10 mL), dried over $Na_2SO_4$, concentrated in vacuum. The residue was purified by column chromatography on silica gel (eluent: DCM:MeOH=50:1) to obtain B5-4 (500 mg) as a white solid. MS (ESI, m/e) $[M+1]^+$ 634.0.

B5-5: 4-(2-((S)-2-(2-isopropylphenyl)pyrrolidin-1-yl)-7-azaspiro[3,5]nonan-7-yl)-2-((R)-3-methyl-2,3-dihydropyrrolo[3',2':5,6]pyrido[2,3-b][1,4]oxazin-1(6H)-yl)benzoic acid

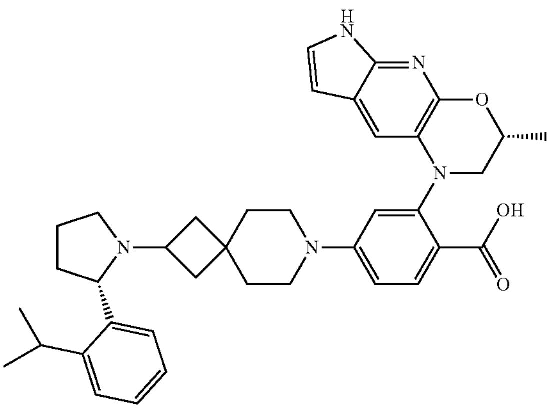 [SMILES: CC(C)c1ccccc1[C@@H]1CCCN1C1CC2(CCN(c3ccc(C(=O)O)c(N4C[C@@H](C)Oc5nc6[nH]ccc6cc54)c3)CC2)C1]

To a solution of methyl 4-(2-((S)-2-(2-isopropylphenyl)pyrrolidin-1-yl)-7-azaspiro[3,5]nonan-7-yl)-2-((R)-3-methyl-2,3-dihydropyrrolo[3',2':5,6]pyrido[2,3-b][1,4]oxazin-1(6H)-yl)benzoate (500 mg, 0.78 mmol) in THF (2 mL) and MeOH (2 mL) was added aq. NaOH (6N, 2 mL). The mixture was stirred at 50° C. for 18 hours. The reaction mixture was cooled to room temperature and then adjusted PH to ~4 with concentrated HCl acid. The mixture was extracted with DCM (50 mL×2). The combined organic phase was washed with brine, dried over $Na_2SO_4$, concentrated in vacuum. The residue was purified by column chromatography on silica gel (eluent: DCM: MeOH=20:1) to obtain B5-5 (250 mg). MS (ESI, m/e) $[M+1]^+$ 620.0.

Then the desired compound was synthesized with 4-(2-((S)-2-(2-isopropylphenyl)pyrrolidin-1-yl)-7-azaspiro[3,5]nonan-7-yl)-2-((R)-3-methyl-2,3-dihydropyrrolo[3',2':5,6]pyrido[2,3-b][1,4]oxazin-1(6H)-yl)benzoic acid and 4-((((1R,4R)-4-hydroxy-4-methylcyclohexyl)methyl)amino)-3-nitrobenzenesulfonamide following the similar procedure of Example B1. $^1H$ NMR (DMSO-$d_6$) δ ppm: 12.14 (s, 1H), 11.02 (s, 1H), 10.06 (s, 1H), 8.50 (s, 1H), 8.33 (s, 1H), 7.76 (s, 1H), 7.56 (s, 2H), 7.40-7.09 (m, 4H), 7.01 (s, 1H), 6.88-6.43 (m, 4H), 5.93 (s, 1H), 4.77 (s, 1H), 4.57 (s, 1H), 4.25 (s, 1H), 3.90 (s, 1H), 3.68 (s, 1H), 3.51-3.49 (m, 1H), 3.25-3.21 (m, 3H), 2.12 (s, 3H), 2.04-1.96 (m, 1H), 1.71-1.68 (m, 3H), 1.57-1.54 (m, 3H), 1.39-1.33 (m, 10H), 1.25-1.23 (m, 6H), 1.13-1.12 (m, 8H). MS (ESI) m/e $[M+1]^+$ 946.2.

Example B6: N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3,5]nonan-7-yl)-2-((S)-3-methyl-2,3-dihydropyrrolo[3',2':5,6]pyrido[2,3-b][1,4]oxazin-1(6H)-yl)benzamide

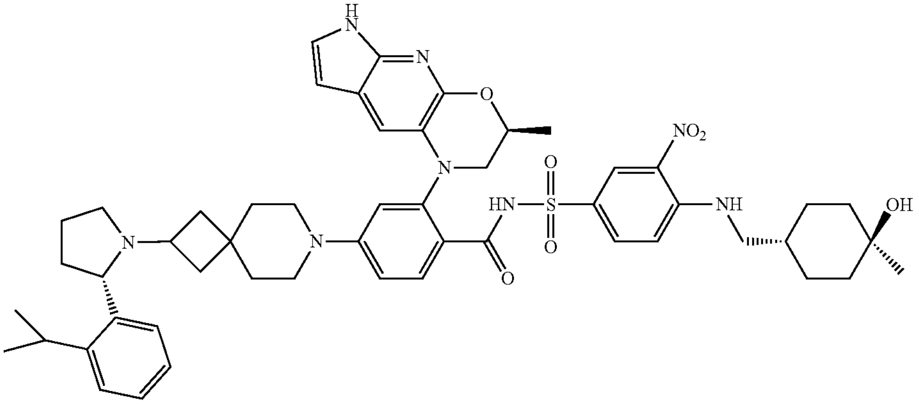 [SMILES: CC(C)c1ccccc1[C@@H]1CCCN1C1CC2(CCN(c3ccc(C(=O)NS(=O)(=O)c4ccc(NC[C@H]5CC[C@](C)(O)CC5)c([N+](=O)[O-])c4)c(N4C[C@H](C)Oc5nc6[nH]ccc6cc54)c3)CC2)C1]

B6-1: (S)-3-methyl-6-((2-(trimethylsilyl)ethoxy)methyl)-1,2,3,6-tetrahydropyrrolo[3',2':5,6]pyrido[2,3-b][1,4]oxazine

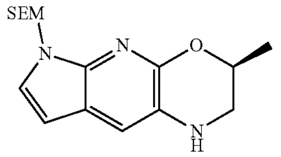 [SMILES: C[C@H]1CNc2cc3ccn(COCC[Si](C)(C)C)c3nc2O1]

B6-1 was synthesized following the similar procedures of B5-1 by replacing the starting material (R)-1-aminopropan-2-ol of 15-1 with (S)-1-aminopropan-2-ol. $^1H$ NMR (400 MHz, $CDCl_3$) δ ppm: 7.15 (s, 1H), 7.11 (d, J=3.6 Hz, 1H), 6.29 (d, J=3.6 Hz, 1H), 5.55 (s, 2H), 4.52-4.43 (m, 1H), 3.68

(br, s 1H), 3.57-3.49 (m, 2H), 3.36 (dd, J=11.6, 2.4 Hz, 1H), 3.12 (dd, J=11.6, 8.4 Hz, 1H), 1.47 (d, J=6.4 Hz, 3H), 0.92-0.85 (m, 2H), −0.06 (s, 9H). MS (ESI, m/e) $[M+1]^+$ 320.3.

The desired compound was synthesized with 4-(2-((S)-2-(2-isopropylphenyl)pyrrolidin-1-yl)-7-azaspiro[3,5]nonan-7-yl)-2-((S)-3-methyl-2,3-dihydropyrrolo[3',2':5,6]pyrido[2,3-b][1,4]oxazin-1(6H)-yl)benzoic acid and 4-((((1r,4r)-4-hydroxy-4-methylcyclohexyl)methyl)amino)-3-nitrobenzenesulfonamide following the similar procedure of Example B5. $^1H$ NMR (DMSO-$d_6$) 12.01 (s, 1H), 11.02 (s, 1H), 10.32 (s, 1H), 8.44 (s, 1H), 8.34 (s, 1H), 7.84 (s, 1H), 7.56 (s, 1H), 7.35-7.33 (m, 2H), 7.26-7.24 (m, 2H), 7.01 (s, 1H), 6.84 (s, 11H), 6.73 (s, 1H), 6.55-6.53 (m, 1H), 5.92 (s, 1H), 4.78 (s, 1H), 4.57 (s, 1H), 4.26 (s, 1H), 3.89 (s, 1H), 3.68 (s, 1H), 3.51 (s, 1H), 3.18-3.13 (m, 7H), 2.43 (s, 1H), 2.13 (s, 4H), 2.04-1.95 (m, 1H), 1.70-1.68 (m, 2H), 1.56-154 (m, 2H), 1.38-1.36 (m, 9H), 1.24-1.23 (m, 7H), 1.13-1.10 (m, 8H). MS (ESI) m/e $[M+1]^+$ 946.2.

Example B7: N—(((R)-3-(((1r,4R)-4-hydroxycyclohexyl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3,5]nonan-7-yl)-2-((R)-3-methyl-2,3-dihydropyrrolo[3',2':5,6]pyrido[2,3-b][1,4]oxazin-1(6H)-yl)benzamide

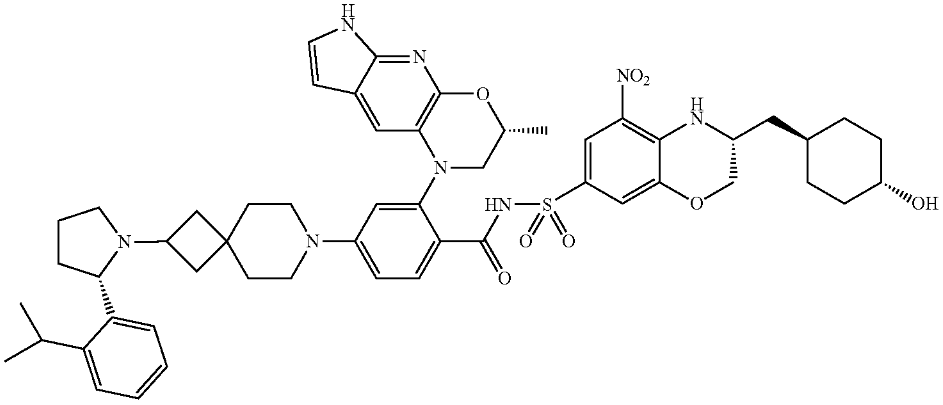 [SMILES: CC(C)c1ccccc1[C@@H]1CCCN1C1CC2(CCN(c3ccc(C(=O)NS(=O)(=O)c4cc5c(c([N+](=O)[O-])c4)N[C@H](C[C@H]4CC[C@H](O)CC4)CO5)c(N4C[C@@H](C)Oc5nc6[nH]ccc6cc54)c3)CC2)C1]

The desired compound was synthesized with 4-(2-((S)-2-(2-isopropylphenyl)pyrrolidin-1-yl)-7-azaspiro[3,5]nonan-7-yl)-2-((R)-3-methyl-2,3-dihydropyrrolo[3',2':5,6]pyrido[2,3-b][1,4]oxazin-1(6H)-yl)benzoic acid and (R)-3-(((1R,4R)-4-hydroxycyclohexyl)methyl)-5-nitro-3,4-dihydro-2H-benzo[b][1,4]oxazine-7-sulfonamide following the similar procedure of Example B5. $^1H$ NMR (DMSO-$d_6$) δ ppm: 12.20 (s, 1H), 10.90 (s, 1H), 10.09 (s, 1H), 8.65 (s, 1H), 7.91 (s, 1H), 7.79-7.78 (m, 1H), 7.55 (s, 1H), 7.36 (s, 4H), 7.30 (s, 1H), 7.04 (s, 1H), 6.97 (s, 1H), 6.83 (s, 1H), 6.69-6.68 (m, 11H), 6.51 (s, 1H), 5.94 (s, 1H), 4.78-4.77 (m, 1H), 4.44-4.43 (m, 2H), 4.01 (s, 3H), 3.87-3.85 (m, 2H), 3.69 (s, 3H), 3.16 (s, 2H), 3.08-2.99 (m, 2H), 2.44-2.37 (m, 1H), 2.12 (s, 5H), 2.00-1.98 (m, 3H), 1.81 (s, 6H), 1.71 (s, 1H), 1.46-1.43 (m, 2H), 1.34 (s, 3H), 1.17-1.14 (m, 4H), 1.12 (s, 5H), 0.88-0.84 (m, 3H). MS (ESI) m/e $[M+1]^+$ 974.1.

Example B8: N—(((R)-3-(((1r,4R)-4-hydroxycyclohexyl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3,5]nonan-7-yl)-2-((S)-3-methyl-2,3-dihydropyrrolo[3',2':5,6]pyrido[2,3-b][1,4]oxazin-1(6H)-yl)benzamide

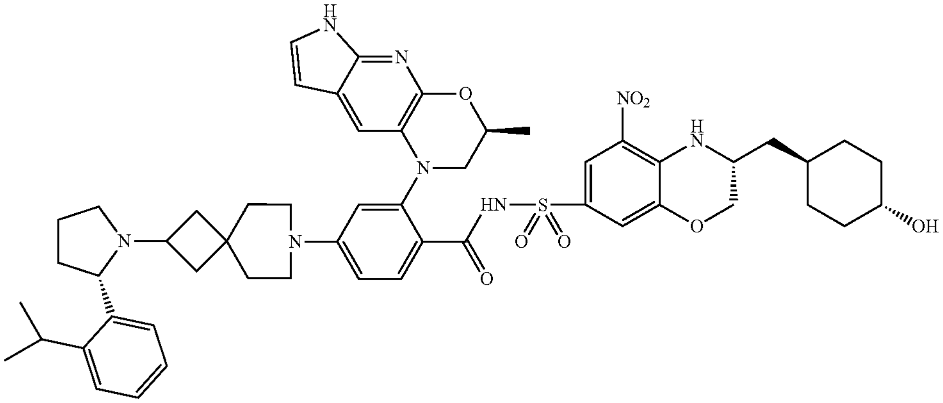

The desired compound was synthesized with 4-(2-((S)-2-(2-isopropylphenyl)pyrrolidin-1-yl)-7-azaspiro[3,5]nonan-7-yl)-2-((S)-3-methyl-2,3-dihydropyrrolo[3',2':5,6]pyrido[2,3-b][1,4]oxazin-1(6H)-yl)benzoic acid and (R)-3-(((1R,4R)-4-hydroxycyclohexyl)methyl)-5-nitro-3,4-dihydro-2H-benzo[b][1,4]oxazine-7-sulfonamide following the similar procedure of Example B5. MS (ESI) m/e $[M+1]^+$ 974.18.

Example B9: 2-(3,4-dihydro-2H-pyrrolo[3',2':5,6]pyrido[2,3-b][1,4]oxazepin-1(7H)-yl)-N—(((R)-3-(((1R,4R)-4-hydroxycyclohexyl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3,5]nonan-7-yl)benzamide

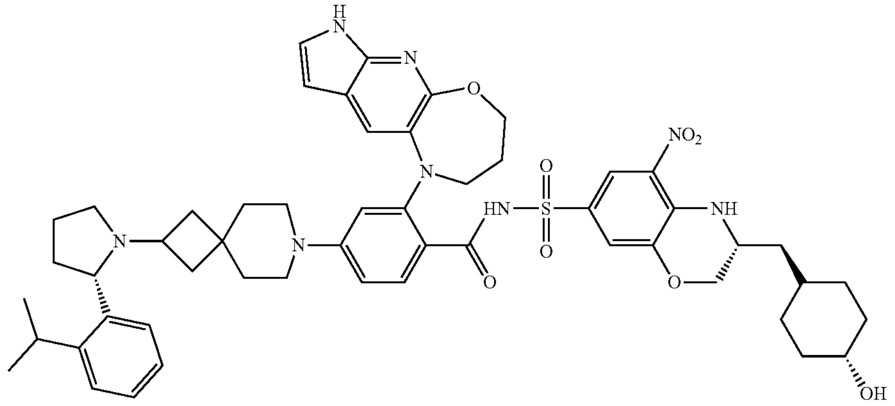

The desired compound was synthesized with (S)-2-(3,4-dihydro-2H-pyrrolo[3',2':5,6]pyrido[2,3-b][1,4]oxazepin-1(7H)-yl)-4-(2-(2-(2-isopropylphenyl)pyrrolidin-1-yl)-7-azaspiro[3,5]nonan-7-yl)benzoic acid and (R)-3-(((1R,4R)-4-hydroxycyclohexyl)methyl)-5-nitro-3,4-dihydro-2H-benzo[b][1,4]oxazine-7-sulfonamide following the similar procedure of Example B5. $^1$H NMR (400 MHz, DMSO-$d_6$) δ ppm: 11.99 (s, 11H), 11.15 (s, 11H). 10.11-9.90 (m, 1H), 8.74 (s, 1H), 8.06 (s, 1H), 7.82-7.68 (m, 1H), 7.53-7.45 (m, 1H), 7.45-7.27 (m, 3H), 7.25-7.07 (m, 2H), 6.89 (s, 1H), 6.79-6.60 (m, 2H), 6.10 (s, 1H), 4.85-4.70 (m, 1H), 4.60-4.30 (m, 1H), 4.21 (s, 2H), 4.09-3.98 (m, 2H), 3.98-3.85 (m, 1H), 3.80-3.62 (m, 2H), 3.57-3.48 (m, 2H), 3.24-3.02 (m, 6H), 2.20-2.08 (m, 4H), 2.05-1.93 (m, 4H), 1.89-1.74 (m, 3H), 1.74-1.64 (m, 1H), 1.57-1.40 (m, 6H), 1.37-1.26 (m, 7H), 1.16-1.08 (m, 4H), 1.00-0.89 (m, 2H). MS (ESI, m/e) $[M+1]^+$ 972.9.

Example B10: N-((4-((((1R,4R)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3,5]nonan-7-yl)-2-(2-methyl-2,3-dihydropyrrolo[3'2':5,6]pyrido[2,3-b][1,4]oxazin-1(6H)-yl)benzamide

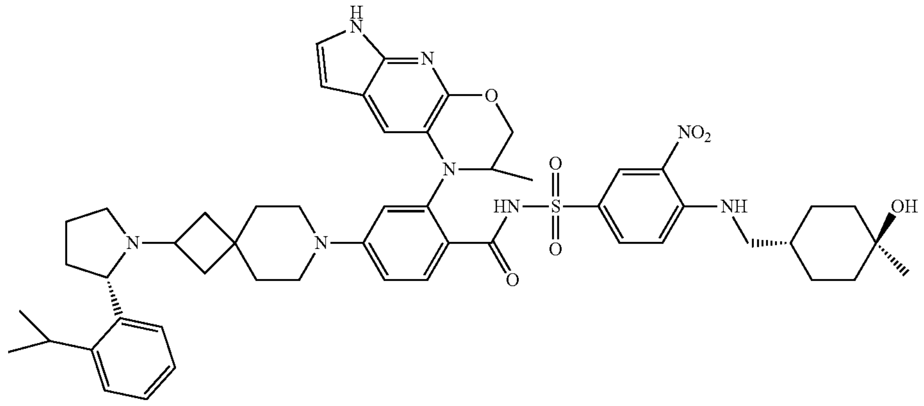 [SMILES: CC(C)c1ccccc1[C@@H]1CCCN1C1CC2(CCN(c3ccc(C(=O)NS(=O)(=O)c4ccc(NC[C@H]5CC[C@](C)(O)CC5)c([N+](=O)[O-])c4)c(N4c5cc6cc[nH]c6nc5OCC4C)c3)CC2)C1]

The desired compound was synthesized with 4-(2-((S)-2-(2-isopropylphenyl)pyrrolidin-1-yl)-7-azaspiro[3,5]nonan-7-yl)-2-(2-methyl-2,3-dihydropyrrolo[3',2':5,6]pyrido[2,3-b][1,4]oxazin-1(6H)-yl)benzoic acid and 4-((((1R,4R)-4-hydroxy-4-methylcyclohexyl)methyl)amino)-3-nitrobenzenesulfonamide following the similar procedure of Example B5. $^1$H NMR (400 MHz, DMSO-$d_6$) δ ppm: 12.95 (s, 1H), 11.24 (s, 1H), 9.82 (s, 1H), 8.53-8.02 (m, 2H), 7.82-7.65 (m, 1H), 7.50-7.26 (m, 3H), 7.24-7.06 (m, 2H), 7.04-6.37 (m, 5H), 6.04 (s, 1H), 4.88-4.52 (m, 1H), 4.25 (s, 1H), 4.18-3.82 (m, 3H), 3.72-3.55 (m, 1H), 3.27-2.90 (m, 10H), 2.23-1.94 (m, 5H), 1.83-1.32 (m, 16H), 1.18-1.05 (m, 10H). MS (ESI, m/e) $[M+1]^+$ 944.9.

Example B11: 2-(2,3-dihydropyrrolo[3',2':5,6]pyrido[2,3-b][1,4]oxazin-1(6H)-yl)-N-((4-((((1R,4R)-4-hydroxy-4-methylcyclohexyl)methyl)amino)-3-nitrophenyl)sulfonyl)-4-(6-((S)-2-(2-isopropylphenyl)pyrrolidin-1-yl)-2-azaspiro[3.3]heptan-2-yl)benzamide

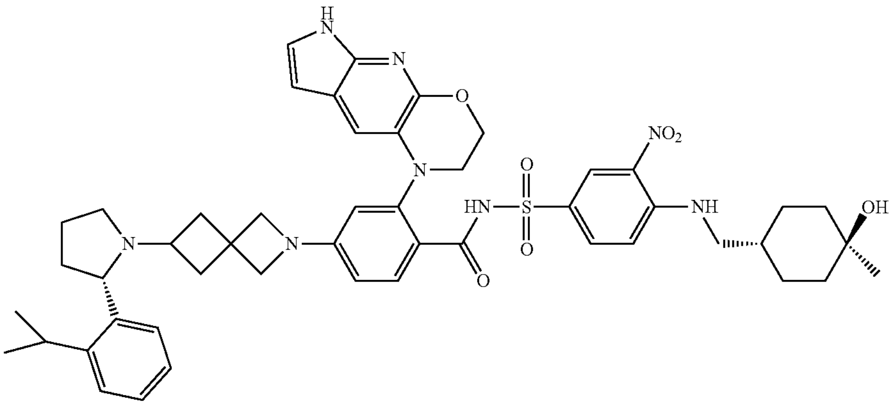 [SMILES: CC(C)c1ccccc1[C@@H]1CCCN1C1CC2(C1)CN(c1ccc(C(=O)NS(=O)(=O)c3ccc(NC[C@H]4CC[C@](C)(O)CC4)c([N+](=O)[O-])c3)c(N3CCOc4nc5[nH]ccc5cc43)c1)C2]

The desired compound was synthesized with (S)-2-(2,3-dihydropyrrolo[3',2':5,6]pyrido[2,3-b][1,4]oxazin-1(6H)-yl)-4-(6-(2-(2-isopropylphenyl)pyrrolidin-1-yl)-2-azaspiro[3.3]heptan-2-yl)benzoic acid and 4-((((1R,4R)-4-hydroxy-4-methylcyclohexyl)methyl)amino)-3-nitrobenzenesulfonamide following the similar procedure of Example B5. $^1$H NMR (DMSO-$d_6$) δ ppm: 12.12 (s, 1H), 11.04 (s, 1H), 8.49 (s, 1H), 8.36 (s, 1H), 7.55-7.53 (m, 2H), 7.32 (s, 1H), 7.20 (s, 1H), 7.12 (s, 1H), 7.02 (s, 1H), 6.67 (s, 1H), 6.61 (s, 1H), 6.25 (d, J=7.9 Hz, 1H), 6.14 (s, 1H), 5.96 (s, 1H), 4.44 (s, 2H), 4.26 (s, 1H), 3.76-3.73 (m, 4H), 3.59-3.56 (m, 6H), 3.22 (s, 2H), 3.09-3.07 (m, 2H), 2.10 (s, 2H), 2.02-1.94 (m, 1H), 1.76-1.73 (m, 5H), 1.56-1.54 (m, 3H), 1.45 (s, 1H), 1.38-1.30 (m, 2H), 1.24 (s, 5H), 1.16-1.15 (m, 6H), 1.12-1.10 (m, 4H). MS (ESI) m/e $[M+1]^+$ 904.

Example B12: (S)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)-4-(6-(2-(2-isopropylphenyl)pyrrolidin-1-yl)-2-azaspiro[3.3]heptan-2-yl)benzamide

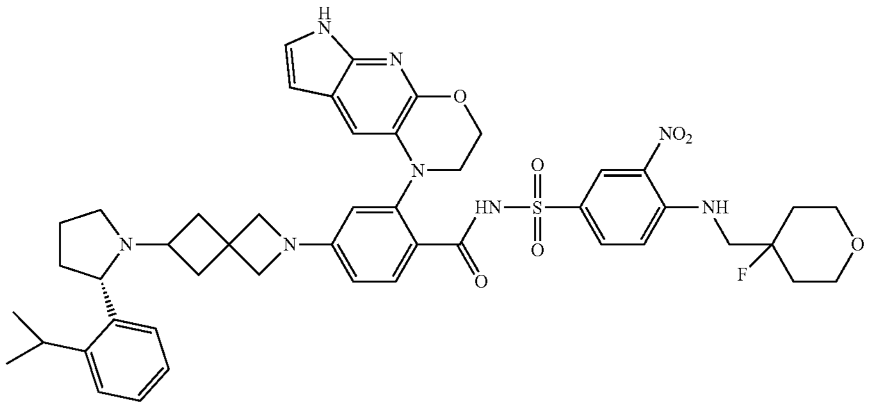 [SMILES: CC(C)c1ccccc1[C@@H]1CCCN1C1CC2(C1)CN(c1ccc(C(=O)NS(=O)(=O)c3ccc(NCC4(F)CCOCC4)c([N+](=O)[O-])c3)c(N3CCOc4nc5[nH]ccc5cc43)c1)C2]

The desired compound was synthesized with (S)-2-(2,3-dihydropyrrolo[3',2':5,6]pyrido[2,3-b][1,4]oxazin-1(6H)-yl)-4-(6-(2-(2-isopropylphenyl)pyrrolidin-1-yl)-2-azaspiro[3.3]heptan-2-yl)benzoic acid and 4-(((4-fluorotetrahydro-2H-pyran-4-yl)methyl)amino)-3-nitrobenzenesulfonamide following the similar procedure of Example B5. $^1$H NMR ($DMSO-d_6$) δ ppm: 12.11 (s, 1H), 11.03 (s, 1H), 10.21 (s, 1H), 8.56 (s, 1H), 8.37 (s, 1H), 7.54-7.53 (m, 2H), 7.43-7.12 (m, 4H), 7.04 (s, 1H), 6.86 (d, J=9.0 Hz, 1H), 6.62 (s, 1H), 6.26 (d, J=8.4 Hz, 1H), 6.15 (s, 1H), 5.95 (s, 1H), 4.43 (s, 2H), 3.88-3.61 (m, 11H), 3.53 (s, 5H), 3.13-2.87 (m, 3H), 2.09-2.07 (m, 3H), 1.83-1.81 (m, 8H), 1.13 (s, 4H). MS (ESI) m/e $[M+1]^+$ 894.0.

Example B13: 2-(3,4-dihydro-2H-pyrrolo[3',2':5,6]pyrido[2,3-b][1,4]oxazepin-1(7H)-yl)-N-((4-((((1r,4r)-4-hydroxy-4-methylcyclohexyl)methyl)amino)-3-nitrophenyl)sulfonyl)-4-(6-((S)-2-(2-isopropylphenyl)pyrrolidin-1-yl)-2-azaspiro[3,3]heptan-2-yl)benzamide

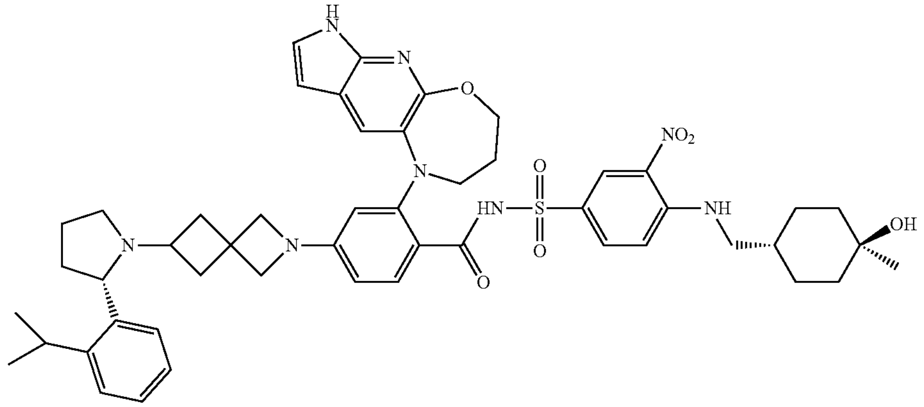 [SMILES: CC(C)c1ccccc1[C@@H]1CCCN1C1CC2(C1)CN(c1ccc(C(=O)NS(=O)(=O)c3ccc(NC[C@H]4CC[C@](C)(O)CC4)c([N+](=O)[O-])c3)c(N3CCCOc4nc5[nH]ccc5cc43)c1)C2]

The desired compound was synthesized with (S)-2-(3,4-dihydro-2H-pyrrolo[3',2':5,6]pyrido[2,3-b][1,4]oxazepin-1(7H)-yl)-4-(6-(2-(2-isopropylphenyl)pyrrolidin-1-yl)-2-azaspiro[3.3]heptan-2-yl)benzoic acid and 4-((((1R,4R)-4-hydroxy-4-methylcyclohexyl)methyl)amino)-3-nitrobenzenesulfonamide following the similar procedure of Example B5. $^1$H NMR ($DMSO-d_6$) δ ppm: 11.91 (s, 1H), 11.34 (s, 1H), 8.64-8.53 (m, 1H), 8.53-8.44 (m, 1H), 7.70-7.44 (m, 3H), 7.35-7.11 (m, 4H), 7.00 (s, 1H), 6.91 (d, J=9.3 Hz, 1H), 6.28-6.08 (m, 2H), 4.31 (s, 1H), 4.28-4.20 (m, 2H), 3.93-3.63 (m, 5H), 3.59-3.48 (m, 2H), 3.33-3.25 (m, 2H), 3.23-2.91 (m, 2H), 2.29-2.13 (m, 2H), 2.12-1.99 (m, 3H), 1.97-1.45 (m, 11H), 1.43-1.35 (m, 3H), 1.26-1.19 (m, 5H), 1.19-1.10 (m, 5H). MS (ESI, m/e) $[M+1]^+$ 916.9.

Example B14: (S)-2-(3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)-4-(6-(2-(2-isopropylphenyl)pyrrolidin-1-yl)-2-azaspiro[3.3]heptan-2-yl)benzamide

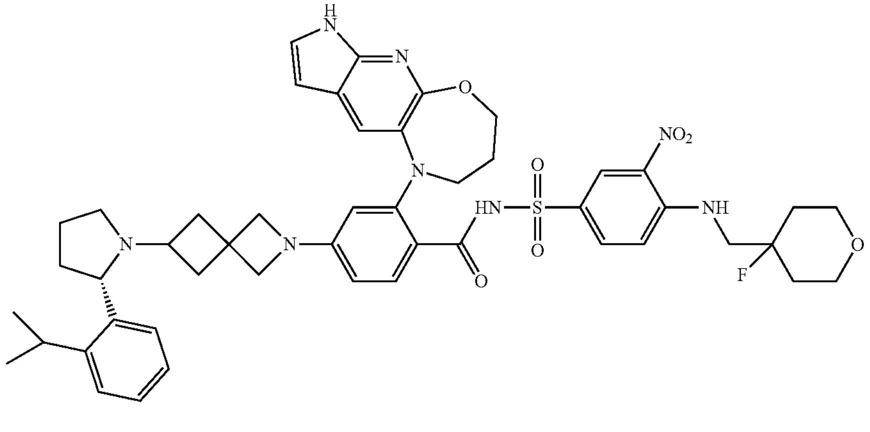 [SMILES: CC(C)c1ccccc1[C@@H]1CCCN1C1CC2(C1)CN(c1ccc(C(=O)NS(=O)(=O)c3ccc(NCC4(F)CCOCC4)c([N+](=O)[O-])c3)c(N3CCCOc4nc5[nH]ccc5cc43)c1)C2]

The desired compound was synthesized with (S)-2-(3,4-dihydro-2H-pyrrolo[3',2':5,6]pyrido[2,3-b][1,4]oxazepin-1(7H)-yl)-4-(6-(2-(2-isopropylphenyl)pyrrolidin-1-yl)-2-azaspiro[3.3]heptan-2-yl)benzoic acid and 4-(((4-fluorotetrahydro-2H-pyran-4-yl)methyl)amino)-3-nitrobenzenesulfonamide following the similar procedure of Example B5. $^1$H NMR (DMSO-$d_6$) δ ppm: 11.87 (s, 1H), 11.25 (s, 1H), 8.63-8.52 (s, 1H), 8.49-8.42 (m, 1H), 7.66-7.60 (m, 1H), 7.57-7.46 (m, 1H), 7.46-7.38 (m, 1H), 7.38-7.00 (m, 6H), 6.94 (s, 1H), 6.19-6.02 (m, 3H), 4.18 (s, 2H), 3.87-3.57 (m, 9H), 3.56-3.42 (m, 4H), 3.17-2.81 (m, 3H), 2.20-2.09 (m, 2H), 2.05-1.90 (m, 3H), 1.90-1.69 (m, 8H), 1.55-1.40 (m, 2H), 1.19-1.11 (m, 5H). MS (ESI, m/e) $[M+1]^+$ 906.9.

Example B15: N-((4-((((S)-1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(6-((S)-2-(2-isopropylphenyl)pyrrolidin-1-yl)-2-azaspiro[3,3]heptan-2-yl)benzamide

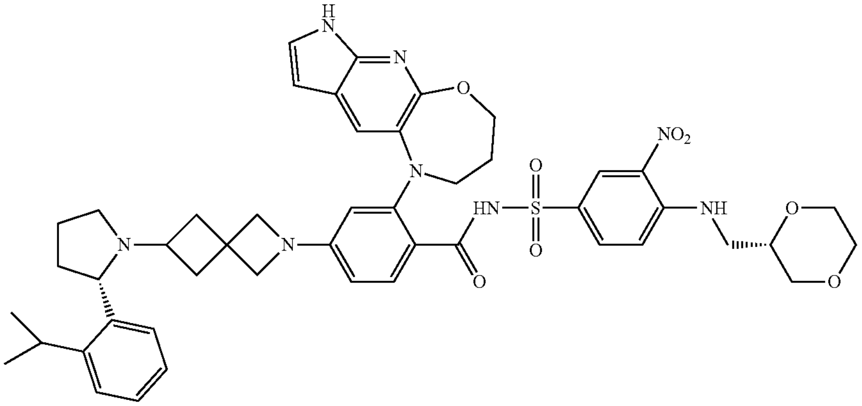 [SMILES: CC(C)c1ccccc1[C@@H]1CCCN1C1CC2(C1)CN(c1ccc(C(=O)NS(=O)(=O)c3ccc(NC[C@H]4COCCO4)c([N+](=O)[O-])c3)c(N3CCCOc4nc5[nH]ccc5cc43)c1)C2]

The desired compound was synthesized with (S)-2-(3,4-dihydro-2H-pyrrolo[3',2':5,6]pyrido[2,3-b][1,4]oxazepin-1(7H)-yl)-4-(6-(2-(2-isopropylphenyl)pyrrolidin-1-yl)-2-azaspiro[3.3]heptan-2-yl)benzoic acid and (S)-4-(((1,4-dioxan-2-yl)methyl)amino)-3-nitrobenzenesulfonamide following the similar procedure of Example B5. $^1$H NMR (DMSO-$d_6$) δ ppm: 11.85 (s, 1H), 11.24 (s, 1H), 8.58-8.47 (m, 1H), 8.47-8.40 (m, 1H), 7.65-7.57 (m, 1H), 7.57-7.48 (m, 1H), 7.48-7.27 (m, 21H), 7.25-7.18 (m, 2H), 7.18-7.05 (m, 2H), 6.97-6.81 (m, 2H), 6.23-6.00 (m, 3H), 4.34-4.01 (m, 2H), 3.87-3.72 (m, 5H), 3.70-3.56 (m, 31H), 3.54-3.40 (m, 4H), 3.16-2.80 (m, 3H), 2.28-2.09 (m, 3H), 2.06-1.91 (m, 41H), 1.91-1.66 (m, 5H), 1.60-1.40 (m, 3H), 1.20-1.11 (m, 5H). MS (ESI, m/e) $[M+1]^+$ 890.8.

Biochemical Assay

Bcl-2 TR-FRET Assay:

Compounds disclosed herein were tested for blocking of Bcl-2 protein with its ligand in an assay based on Time-Resolved Fluorescence Resonance Energy Transfer (TR-FRET) methodology. Recombinant human 0.05 nM Bcl-2 protein was pre-incubated with a serial dilution of compounds disclosed herein (top final concentration is 1 uM or 0.1 uM or 0.02 uM or 0.01 uM, 10 points) at room temperature for 0.5 hour in an assay buffer containing 20 mM potassium phosphate buffer, pH 7.5, 50 mM NaCl, 1 mM EDTA, 0.05% Tween-20, 0.01% BSA. Then the FITC labeled Bak peptide Ac-GQVGRQLAIIGDK(FITC)INR-amide (0.5 nM) and MAb Anti 6His Tb cryptate Gold were added to plate and further incubated at room temperature for 1 hour. The TR-FRET signals (337 nm-520 nm-490 nm) were read on BMG PHERAstar FSX instrument. The inhibition percentage of Bcl-2 interaction with its ligand in presence of increasing concentrations of compounds was calculated based on the TR-FRET signals. The $IC_{50}$ for each compound was derived from fitting the data to the four-parameter logistic equation by Graphpad Prism software or Dotmatics.

Bcl-2-G101V TR-FRET Assay:

Compounds disclosed herein were tested for blocking of Bcl-2-G101V protein with its ligand in an assay based on time-resolved fluorescence resonance energy transfer methodology. 0.1 nM recombinant human Bcl-2-G101V protein was pre-incubated with a serial dilution of compounds disclosed herein (top final concentration is 10 uM or 1 uM or 0.1 uM, 4-fold or 3-fold serially diluted, 10 points) at room temperature for 0.5 hour in an assay buffer containing 20 mM potassium phosphate buffer, pH 7.5, 50 mM NaCl, 1 mM EDTA, 0.05% Tween-20, 0.01% BSA. Then 5 nM FITC labeled Bak peptide Ac-GQVGRQLAIIGDK(FITC)INR-amide and Mab Anti-6His Tb cryptate Gold was added to plate and further incubated at room temperature for 1 hour. The TR-FRET signals (ex337 nm, em490 nm/520 nm) were read on BMG PHERAstar FSX instrument. The inhibition percentage of Bcl-2-G101V interaction with its ligand in presence of increasing concentrations of compounds was calculated based on the ratio of fluorescence at 490 nm to that at 520 nm. The IC50 for each compound was derived from fitting the data to the four-parameter logistic equation by Graphpad Prism software or Dotmatics.

Cell Proliferation Assay

BA/F3 cell Proliferation Assay:

Murine BA/F3 cells were engineered to be dependent on either BCL-2 wild type (BA/F3-BCL-2) or Bcl-2 G101V (BA/F3-BCL-2 G101V) for survival. Prior to compound treatment, the cells were washed and resuspended in culture medium lacking heat inactive FBS and IL-3 for 24 hr. Cells were then resuspended in the assay medium: RPMI-1640 with 3% heat inactive FBS and seeded 10000 cells/well in a 96-well plate. The cells were treated with a 10-point dilution series of compounds for 24 hrs. After the compound treatment, 30 μl of CellTiter-Glo reagent was added in each well. The effects on proliferation were determined using Cell TiterGlo reagent (Promega) according to the manufacturer's instructions. Luminescent signals were measured using PHERAstar FS plate reader (BMG Labtech). $ICS_{50}$ values for cell viability were determined with GraphPad Prism software and were the geometric mean of 3 independent experiments.

RS4;11 Cell Proliferation Assay:

In our cell proliferation assay, the BCL-2 dependent acute lymphoblastic leukemia (ALL) cell line, RS4;11, was used to study the cellular potency of BCL-2 inhibitors. The cells (ATCC, CRL-1873) were cultured in RPMI-1640 complete medium (RPMI-1640 medium, HEPES (Gibco, 22400-105) supplemented with 10% fetal bovine serum (FBS) (Gibco, 10099-1441), 100 unit/ml penicillin and 100 μg/ml streptomycin (Gibco, 15140122)) and maintained in a humidified chamber at 37° C. containing 5% $CO_2$. Each compound was serially diluted with 1 μM as the maximum concentration. To test the apoptotic effect of the compounds, the cells were seeded at 50,000 in 180 μl per well in 96-well plates and treated with 10-point dilution series of each compound for 48 hrs at 37° C. Cell viability was assessed after the treatment using CellTiter-GLO luminescent assay (Promega) according to the manufacturer's recommendations. Briefly, 30 μl of CellTiter-GLO reagent was added into 200 μl of cell culture, Mixture was agitated on an orbital shaker for 5 mins to ensure cell lysis followed by 7 mins incubation at room temperature to allow development and stabilization of luminescent signals, which corresponded to quantity of ATP and thus the quantity of metabolically active cells. Luminescent signals were measured using PHERAstar FS reader (BMG). Mean $IC_{50}$ values for cell viability were determined with GraphPad Prism software.

Molt-4 Cell Proliferation Assay:

The Bcl-xL-dependent ALL cell line, Molt-4 (ATCC, CRL-1582) was also used in cell proliferation assay to further evaluate the specificity of these inhibitors. Similarly, the cells were cultured in RPMI-1640 complete medium (RPMI-1640 medium, HEPES (Gibco, 22400-105) supplemented with 10% fetal bovine serum (FBS) (Gibco, 10099-1441) c 100 unit/ml penicillin and 100 μg/ml streptomycin (Gibco, 15140122) and 1×GlutaMAX (Gibco, 35050-061)) and maintained in a humidified chamber at 37° C. containing 5% CO2. Each compound was serially diluted with 10 1M as the maximum concentration. The anti-proliferative $IC_{50}$s of these compounds were similarly determined as a percentage of viable cells upon treatment compared to the untreated control using CellTiter-GLO luminescent assay.

Select compounds prepared as described above were assayed according to the biological procedures described herein. The results were given in Table 1.

TABLE 1 results of biological activity

| | Biochemical assay (IC50, nM) | | Cellular proliferation assay (IC50, nM) | | | |
|---|---|---|---|---|---|---|
| Example | Bcl-2 WT | Bcl-2 G101V | RS4; 11 | Molt-4 | Bcl-2 WT; BaF3 cell | Bcl-2 G101V; BaF3 cell |
| A1 | 0.024 | 1.7 | 1.0 | >10000 | ND | ND |
| A2 | 0.015 | 0.69 | 0.56 | >10000 | 0.72 | 10.4 |
| A3 | 0.016 | 0.92 | 1.0 | 6000 | 0.56 | 10.3 |
| A4 | 0.025 | 0.86 | 0.47 | >10000 | 0.3 | 9.8 |
| A5 | 0.024 | 0.83 | 1.0 | 5160 | 0.41 | 7.5 |
| A6 | 0.021 | 0.51 | 1.3 | ND | 0.25 | 21.1 |
| A7 | 0.021 | 0.92 | 1.5 | ND | 0.38 | 35.8 |
| A8 | 0.029 | 2.4 | 3.2 | ND | 18 | 202 |
| B1 | 0.04 | 1.9 | 1.7 | 6730 | 1.0 | 15.5 |
| B2 | 0.05 | 1.8 | 1.7 | 5560 | 0.82 | 7.8 |
| B3 | 0.063 | 0.94 | 1.1 | 4540 | 1.1 | 10.8 |
| B4 | 0.018 | 1.2 | 0.58 | 1420 | ND | ND |
| B5 | 0.025 | 1.1 | 1.0 | ND | 0.13 | 8.9 |
| B6 | 0.027 | 1.2 | 0.34 | ND | 1.1 | 31.9 |
| B7 | 0.048 | 1.5 | 0.8 | ND | 0.18 | 11.2 |
| B8 | 0.055 | 3.3 | 0.7 | ND | 0.65 | 41.2 |
| B9 | 0.038 | 3.3 | 0.5 | ND | 0.83 | 34.9 |
| B10 | 0.04 | 1.6 | 1.0 | >10000 | ND | ND |
| B11 | 0.041 | 2.8 | 3.2 | >10000 | ND | ND |
| B12 | 0.058 | 3.7 | 3.6 | 7310 | ND | ND |
| B13 | 0.094 | 2.4 | 5.5 | >10000 | 2.8 | 39.1 |
| B14 | 0.11 | 3.1 | 4.8 | >10000 | 2.4 | 26.5 |
| B15 | 0.14 | 5.2 | 8.0 | >10000 | ND | ND |
| ABT-199 | 0.27 | 24 | 4.2 | 2570 | 4 | 220 |
| Example 3 of WO2019040573 | 0.22 | 13 | 9.3 | ND | ND | ND |

Note:

WT means wild type; G101V means Gly101Val mutation in BCL2.

What is claimed is:

1. A compound of Formula (I)

(I)

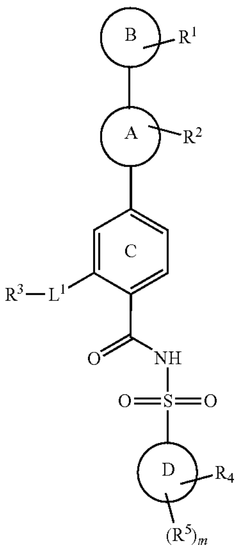

or a pharmaceutically acceptable salt thereof, or a stereoisomer thereof, wherein:

$L^1$ is a direct bond or —O—;

Ring A is cycloalkyl, cycloalkenyl, cycloalkynyl, aryl, heterocyclyl, or heteroaryl, each of which is optionally substituted with 1 to 4 substituents $R^2$;

$R^2$, at each occurrence, is independently hydrogen, deuterium, halogen, or $-C_{1-8}$alkyl optionally substituted with halogen;

Ring B is heterocyclyl containing one heteroatom selected from nitrogen (N), sulfur (S) and oxygen (O), or heteroaryl, each of which is optionally substituted with 1 to 4 substituents $R^1$;

$R^1$, at each occurrence, is independently deuterium, cycloalkyl, heterocyclyl, aryl, or heteroaryl; wherein said cycloalkyl, heterocyclyl, aryl or heteroaryl are each independently optionally substituted with 1 to 4 substituents $R^{1d}$:

$R^{1d}$, at each occurrence, is independently halogen, $-C_{1-8}$alkyl, $-C_{2-8}$alkenyl, $-C_{2-8}$alkynyl, cycloalkyl, heterocyclyl, aryl, heteroaryl, oxo, —CN, $-NO_2$, or $-OR^{Ba}$; wherein said $-C_{1-8}$alkyl, $-C_{2-8}$alkenyl, $C_{2-8}$alkynyl, cycloalkyl, heterocyclyl, aryl, or heteroaryl are each independently optionally substituted with 1 to 4 substituents $R^{Bb}$, $R^{Ba}$ and $R^{Bb}$ are each independently hydrogen, $-C_{1-8}$alkyl, $-C_{2-8}$alkenyl, $-C_{2-8}$alkynyl, cycloalkyl, heterocyclyl, aryl, or heteroaryl wherein each of said $-C_{1-8}$alkyl, $-C_{2-8}$alkenyl, $-C_{2-8}$alkynyl, cycloalkyl, heterocyclyl, aryl, or heteroaryl is optionally substituted with halogen, hydroxy, $-NH_2$, or $-N(C_{1-6}alkyl)_2$, $-C_{1-8}$alkoxy, cycloalkyl, heterocyclyl, aryl, or heteroaryl;

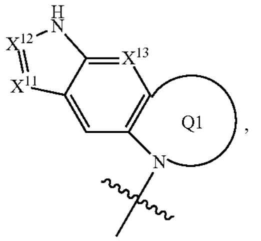

optionally substituted with 1 to 4 substituents $R^{3a}$, wherein $Q^1$ is 6- to 8-membered heterocycloalkyl or 6- to 8-membered heterocycloalkenyl and $X^{11}$, $X^{12}$, and $X^{13}$ are each independently N or CH;

$R^{3a}$, at each occurrence, is independently halogen, $-NR^{3b}R^{3c}$, oxo, or $-C_{1-8}$alkyl;

$R^{3b}$ and $R^{3c}$ are hydrogen or $-C_{1-8}$alkyl;

Ring D is aryl or

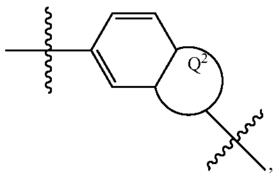

each of which is optionally substituted with 1 to 4 substituents $R^4$;

$Q^2$ is a heterocycloalkyl;

$R^4$, at each occurrence, is independently hydrogen, alkyl, alkenyl, alkynyl, cycloalkyl, cycloalkyl-alkyl, heterocyclyl, heterocyclyl-alkyl, aryl, aryl-alkyl, heteroaryl, heteroaryl-alkyl, halogen, —CN, $-NO_2$, $-(CR^{4}R^{4d})_zNR^{4a}R^{4b}$, $-(CR^{4c}R^{4d})_zOR^{4b}$, $-(CR^{4c}R^{4d})_zC(O)R^{4a}$, $-(CR^{4c}R^{4d})_zC(=NR^{4e})R^{4a}$, $-(CR^{4c}R^{4d})_zC(=N-OR^{4b})R^{4a}$, $-(CR^{4c}R^{4d})_zC(O)OR^{4b}$, $-(CR^{4c}R^{4d})_zOC(O)R^{4b}$, $-(CR^{4c}R^{4d})_zC(O)NR^{4a}R^{4b}$, $-(CR^{4c}R^{4d})_zNR^{4a}C(O)R^{4b}$, $-(CR^{4c}R^{4d})_zC(=NR^{4e})NR^{4a}R^{4b}$, $-(CR^{4c}R^{4d})_zNR^{4a}C(=NR^{4e})R^{4b}$, $-(CR^{4c}R^{4d})_zOC(O)NR^{4a}R^{4b}$, $-(CR^{4c}R^{4d})_zNR^{4a}C(O)OR^{4b}$, $-(CR^{4c}R^{4d})_zNR^{4a}C(O)NR^{4a}R^{4b}$, $-(CR^{4c}R^{4d})_zNR^{4a}C(S)NR^{4a}R^{4b}$, $-(CR^{4c}R^{4d})_zNR^{4a}C(=NR^{4e})NR^{4a}R^{4b}$, $-(CR^{4c}R^{4d})_zS(O)_rR^{4b}$, $-(CR^{4c}R^{4d})_zS(O)(=NR^{4e})R^{4b}$, $-(CR^{4c}R^{4d})_zN=S(O)R^{4a}R^{4b}$, $-(CR^{4c}R^{4d})_zS(O)_2OR^{4b}$, $-(CR^{4c}R^{4d})_zOS(O)_2R^{4b}$, $-(CR^{4c}R^{4d})_zNR^{4a}S(O)_rR^{4b}$, $-(CR^{4c}R^{4d})_zNR^{4a}S(O)(=NR^{4e})R^{4b}$, $-(CR^{4c}R^{4d})_zS(O)_rNR^{4a}R^{4b}$, $-(CR^{4c}R^{4d})_zS(O)(=NR^{4e})NR^{4a}R^{4b}$, $-(CR^{4c}R^{4d})_zNR^{4a}S(O)_2NR^{4a}R^{4b}$, $-(CR^{4c}R^{4d})_zNR^{4a}S(O)(=NR^{4e})NR^{4a}R^{4b}$, $-(CR^{4c}R^{4d})_zP(O)R^{4a}R^{4b}$, or $-(CR^{4c}R^{4d})_zP(O)(OR^{4a})(OR^{4b})$;

each $R^{4a}$ and each $R^{4b}$ are independently hydrogen, alkyl, alkenyl, alkynyl, cycloalkyl, cycloalkyl-alkyl, heterocyclyl, heterocyclyl-alkyl, aryl, aryl-alkyl, heteroaryl, or heteroaryl-alkyl;

each $R^{4c}$ and each $R^{4d}$ are independently hydrogen, halogen, alkyl, alkenyl, alkynyl, cycloalkyl, cycloalkyl-alkyl, heterocyclyl, heterocyclyl-alkyl, aryl, aryl-alkyl, heteroaryl, or heteroaryl-alkyl;

z, at each occurrence, is independently an integer of 1 to 8;

r, at each occurrence, is independently an integer of 1 or 2;

m is an integer of 1-4;

$R^5$ is $—L^2—CyC$;

$L^2$ is a direct bond, $—(CR^aR^b)_t—$, $—O—(CR^aR^b)_t—$, —S—, —S(O)—, $—SO_2—$, —C(O)—, C(O)O—, —OC(O)—, $—NR^a—$, $—N(R^a)(CR^aR^b)_t—$, $—(CR^aR^b)_tC(O)NR^a—$, $—C(O)NR^a—$, $—(CR^aR^b)_t—(NR^a)_t—C$ (O)—, $—NR^aC(O)—$, $—NR^aC(O)O—$, $—NR^aC(O)NR^b—$, $—SO_2NR^a—$, $—NR^aSO_2—$, $—NR^aS(O)_2NR^b—$, $—NR^aS(O)NR^b—$, $—C(O)NR^aSO_2—$, $—C(O)NR^aSO—$, or $—C(=NR^a)NR^b—$, wherein t, at each occurrence, is independently an integer of 0 to 7, and one or two $CR^aR^b$ moieties in $—(CR^aR^b)_t—$ are optionally replaced with one or more moieties selected from O, S, SO, $SO_2$, C(O), and $NR^a$;

$R^a$ and $R^b$ are independently hydrogen or $—C_{1-3}$alkyl;

CyC is $—SO_2R^{5a}—$, cycloalkyl, heterocyclyl, aryl, or heteroaryl; wherein each of said cycloalkyl, heterocyclyl, aryl, or heteroaryl are optionally substituted with one or two substituents $R^{5a}$;

$R^{5a}$, at each occurrence, is independently hydrogen, halogen, cyano, oxo, $—NO_2$, $—OR^{5b}$, $—SR^{5b}$, $—NR^{5b}R^{5c}$, $—COR^{5b}$, $—C_{1-8}$alkyl, $—C_{2-8}$alkenyl, and $—C_{2-8}$alkynyl, —cycloalkyl, or heterocyclyl, wherein each of said $—C_{1-8}$alkyl and heterocyclyl is optionally substituted with one or two substituents $R^{5e}$ which is selected from hydrogen, halogen, cyano, $—OR^{5f}$, $—C_{1-8}$alkyl, —cycloalkyl, or heterocyclyl;

$R^{5b}$ and $R^{5c}$ are each independently hydrogen, $—C_{1-8}$ alkyl, $—C_{2-8}$alkenyl, $—C_{2-8}$alkynyl, cycloalkyl, heterocyclyl, aryl, or heteroaryl, said $—C_{1-8}$alkyl is optionally substituted with one or two substituents $R^{5e}$ which is hydrogen, $—NR^{5f}R^{5g}$, or —cycloalkyl; and $R^{5f}$ and $R^{5g}$ are each independently hydrogen or $—C_{1-8}$ alkyl.

2. The compound of claim 1, wherein $R^3$ is

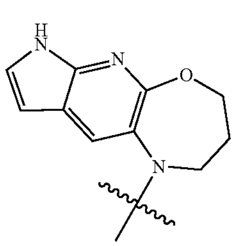
,
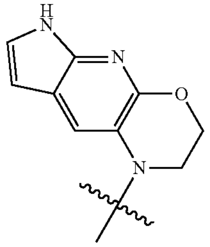
,
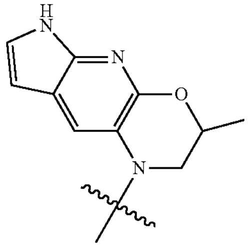
, or
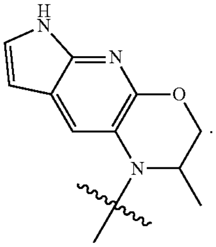
.

3. The compound of claim 1, wherein ring D is

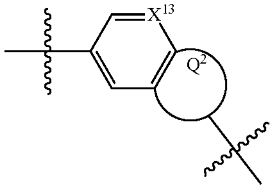

optionally substituted with one or two substituents $R^4$, and $Q^2$ is a 5-membered to 8-membered heterocycloalkyl containing at least one heteroatom independently selected from N, O and S.

4. The compound of claim 1, wherein ring D is

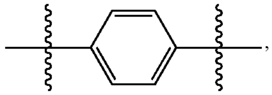
,
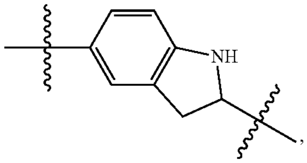
,
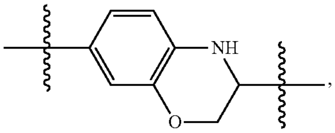
,
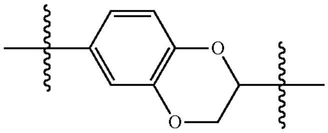
and
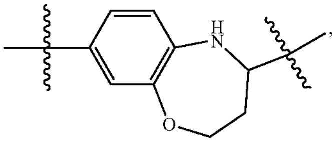
, which is optionally substituted with one or two substituents $R^4$.

5. The compound of claim 1, wherein Ring A is 4-membered/4-membered, 3-membered/5-membered, 4-membered/5-membered, 4-membered/6-membered, 5-membered/5-membered, or 5-membered/6-membered mono-spiro heterocyclyl comprising one or two nitrogen or oxygen heteroatoms as ring members.

6. The compound of claim 5, wherein Ring A is

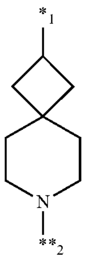
(7-azaspiro[3.5]nonan-2, 7-diyl),
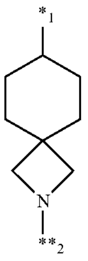
(2-azaspiro[3.5]nonan-2, 7-diyl), -continued

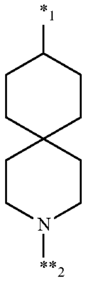 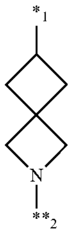

(3-azaspiro[5.5]undecan-3, 9-diyl), (2-azaspiro[3.3]heptan-2, 6-diyl, wherein *1 refers to the position attached to the Ring B, and **2 refers to the position attached to the phenyl ring.

7. The compound of claim 1, wherein $R^2$ is hydrogen, deuterium, halogen, or $C_{1-6}$alkyl optionally substituted with halogen.

8. The compound of claim 1, wherein Ring B is aziridin-1-yl, azetidin-1-yl, pyrrolidin-1-yl, pyrrolidin-2-yl, azepan-1-yl, or azocan-1-yl, substituted with a phenyl group at position 2, and said phenyl group at position 2 is optionally substituted with $R^{1d}$.

9. The compound of claim 8, wherein $R^{1d}$, when substituted on the phenyl group at position 2 of Ring B, is independently halogen, —$C_{1-8}$alkyl, —$C_{2-8}$alkenyl, —$C_{2-8}$alkynyl, cycloalkyl, heterocyclyl, aryl, heteroaryl, —CN, —$OR^{Ba}$, —$SO_2R^{Ba}$, —$CONR^{Ba}R^{Bb}$, —$NO_2$, —$NR^{Ba}R^{Bb}$, —$NR^{Ba}COR^{Bb}$, or —$NR^{Ba}SO_2R^{Bb}$., wherein said —$C_{1-8}$alkyl, —$C_{2-8}$alkenyl, —$C_{2-8}$alkynyl, cycloalkyl, heterocyclyl, aryl or heteroaryl are each independently optionally substituted with 1 to 4 substituents $R^{Bb}$.

10. The compound of claim 8, wherein the 2-(2-substituted phenyl) pyrrolidin-1-yl moiety as Ring B is

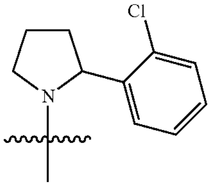, 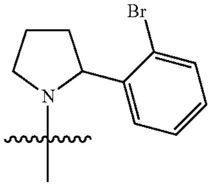,

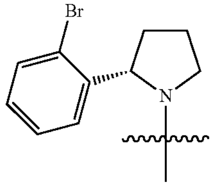, 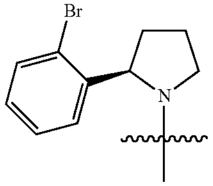,

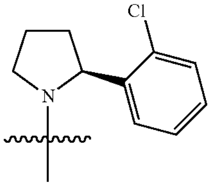, 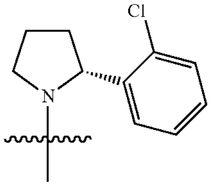,

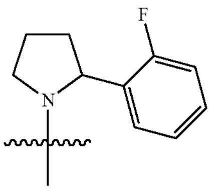, 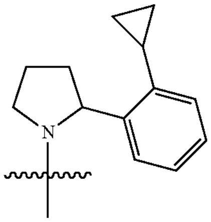,

-continued

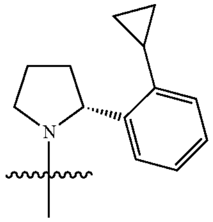, 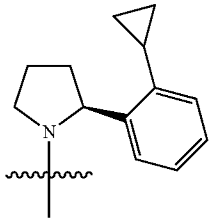,

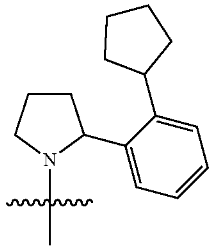, 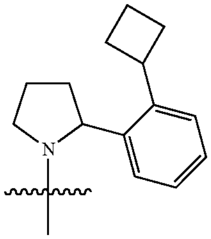,

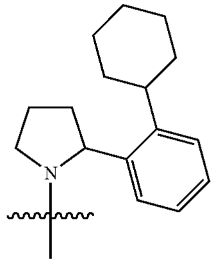, 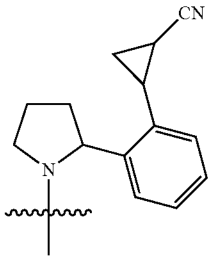,

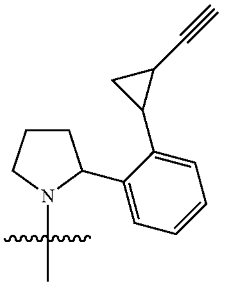, 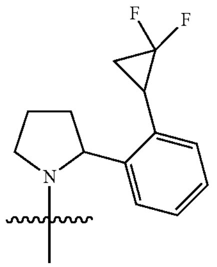,

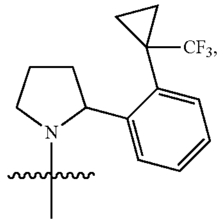 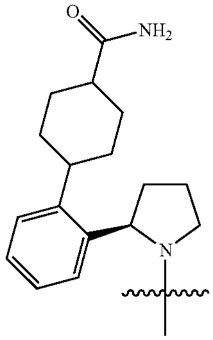,

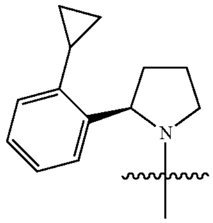, 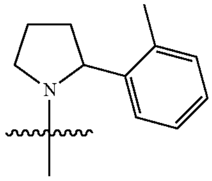,

-continued
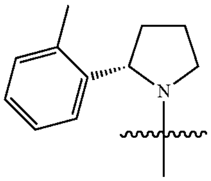,
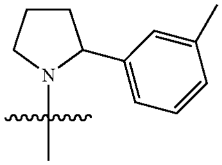,
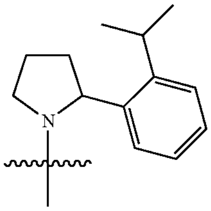,
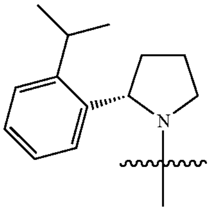,
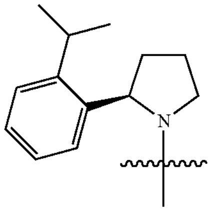,
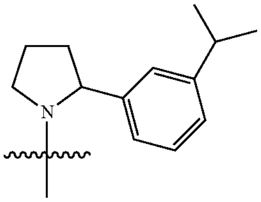,
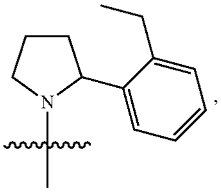,
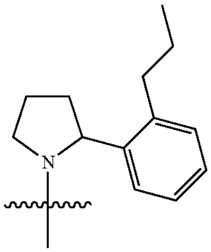,
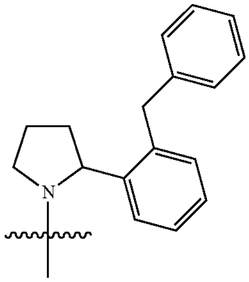,
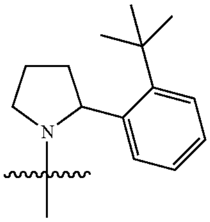,
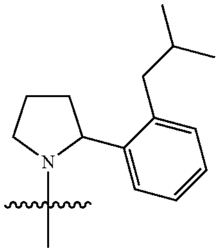,
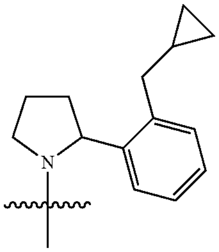,
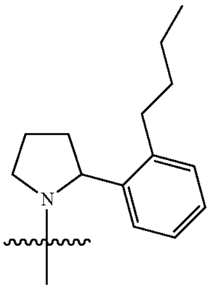,
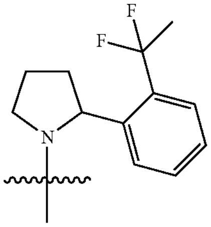,
-continued
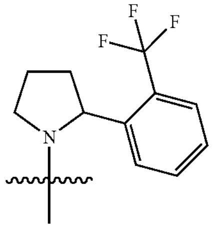,
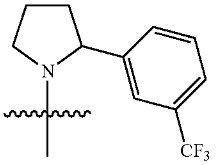,
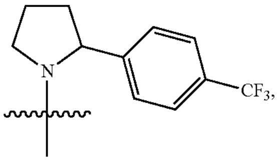
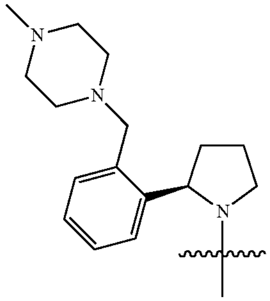,
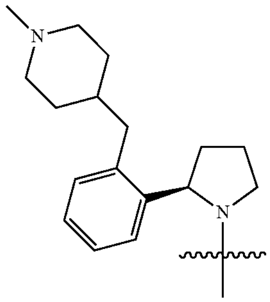,
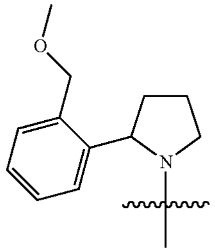,
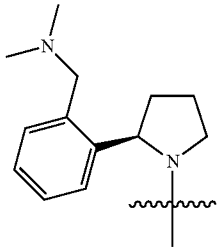,
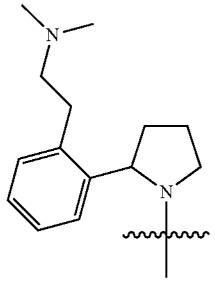,
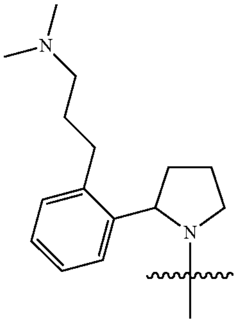,
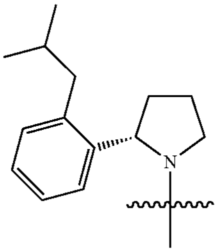,
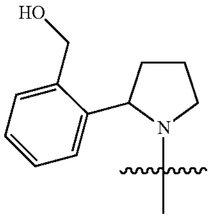,
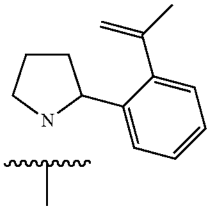, -continued
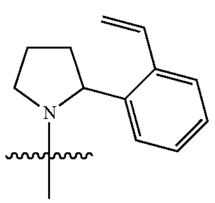
,
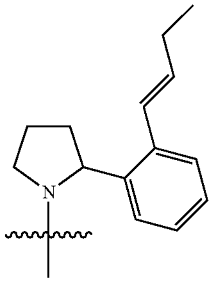
,
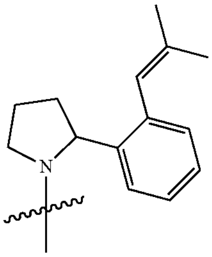
,
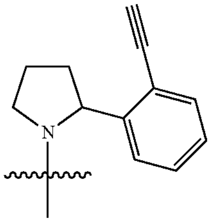
,
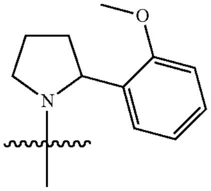
,
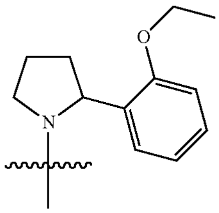
,
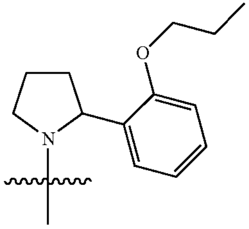
,
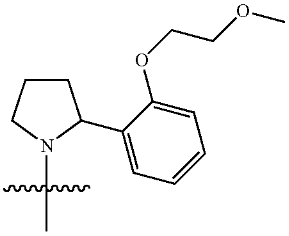
,
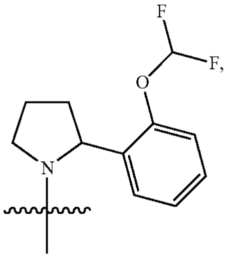
,
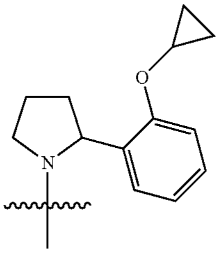
,
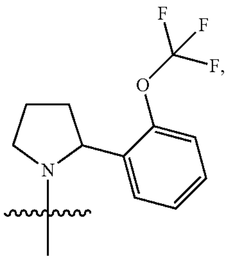
,
-continued
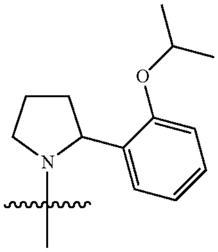
,
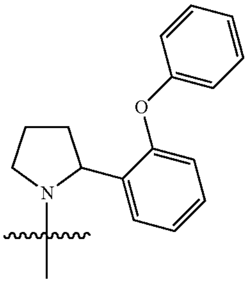
,
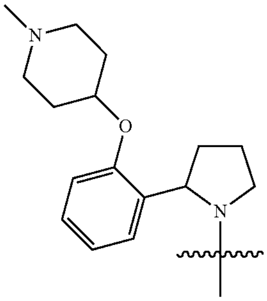
,
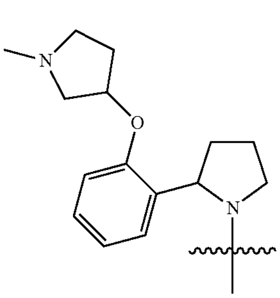
,
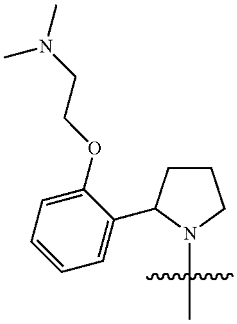
,
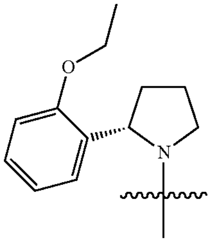
,
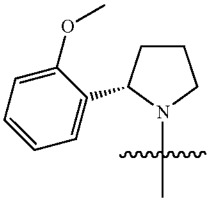
,
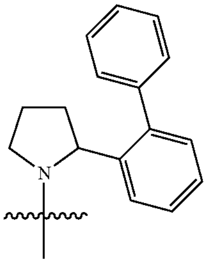
,
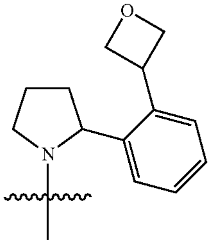
,
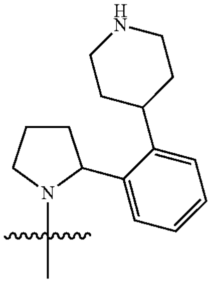
,
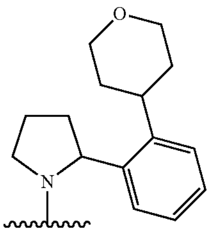
, -continued
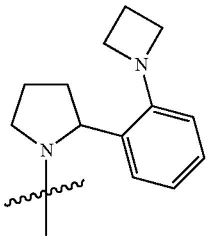,
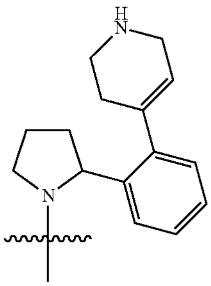,
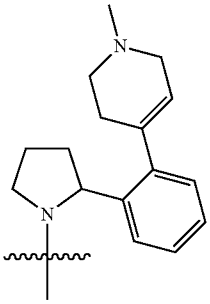,
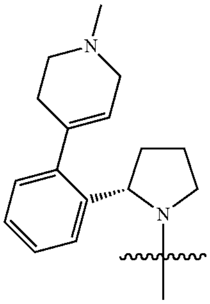,
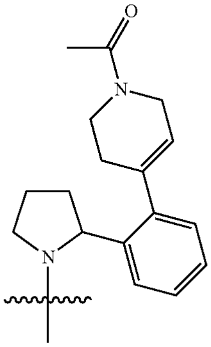,
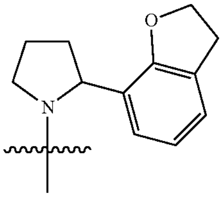,
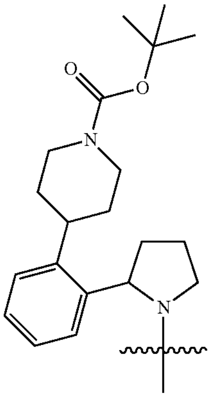,
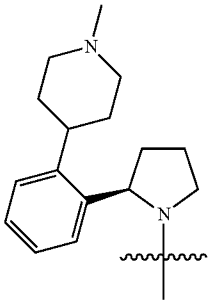,
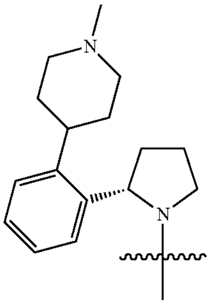,
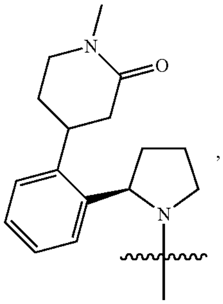,
-continued
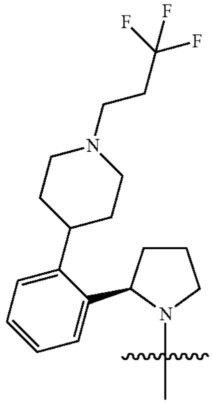,
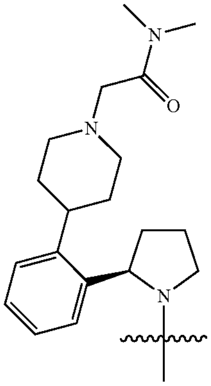,
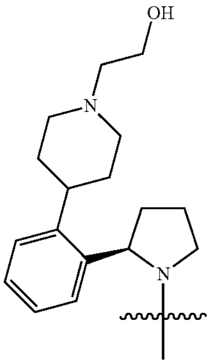,
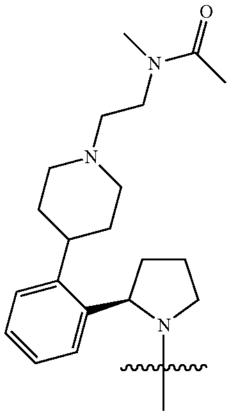,
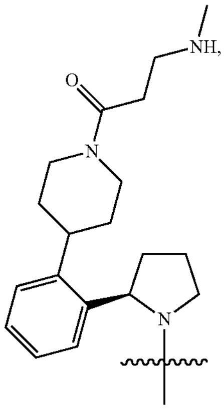,
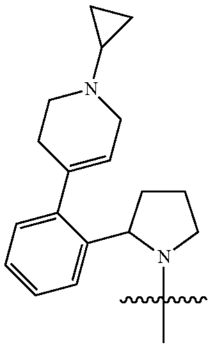,
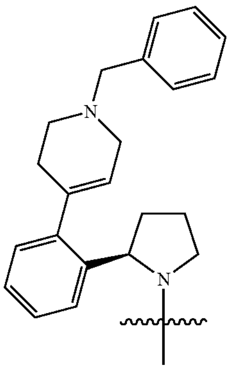,
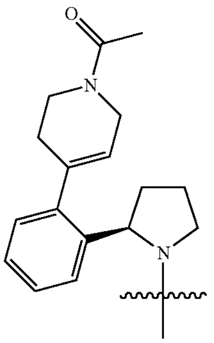, -continued
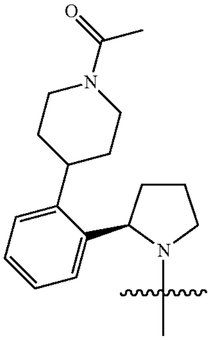,
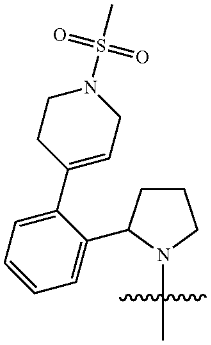,
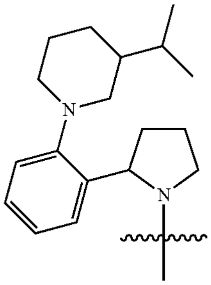,
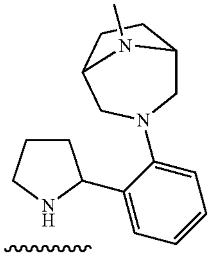,
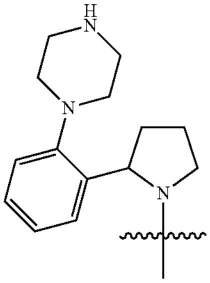,
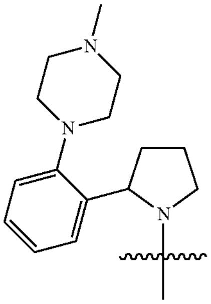,
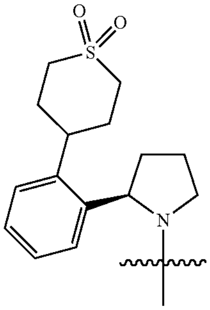,
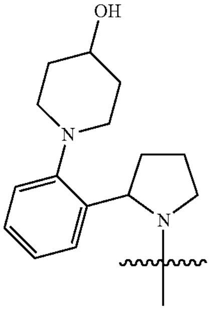,
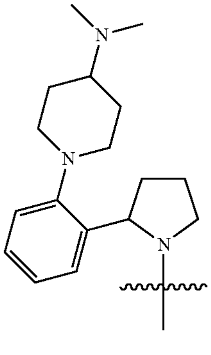,
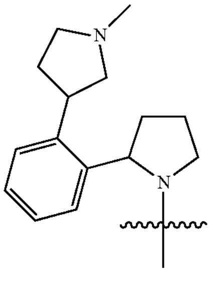,
-continued
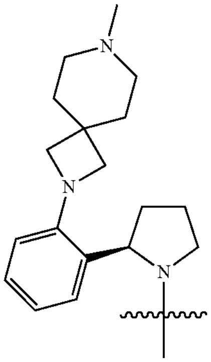,
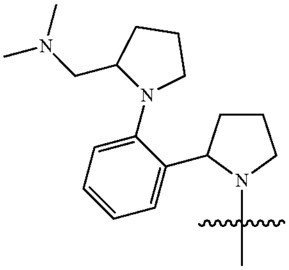,
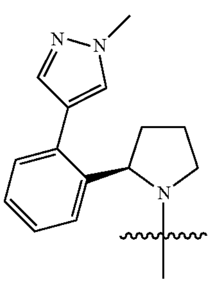,
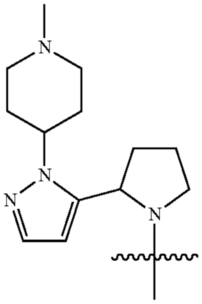,
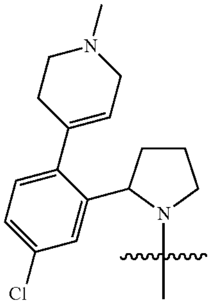,
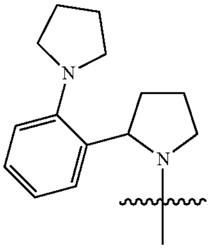,
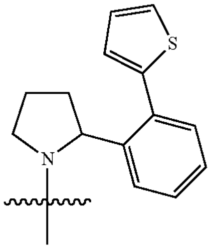,
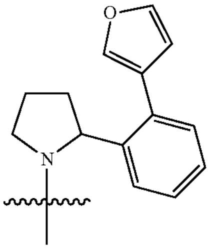,
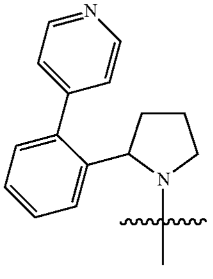,
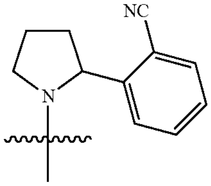,
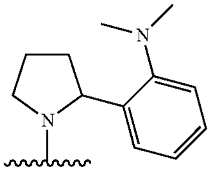,
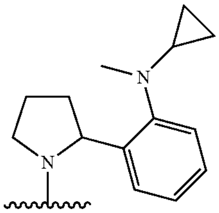, -continued

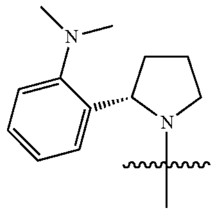
,
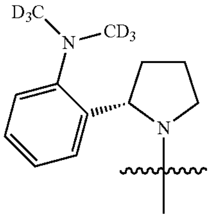
,
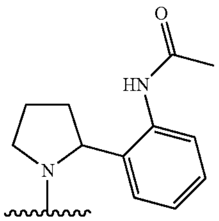
,
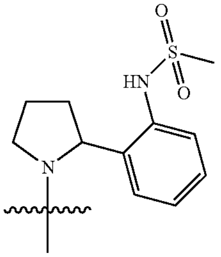
,
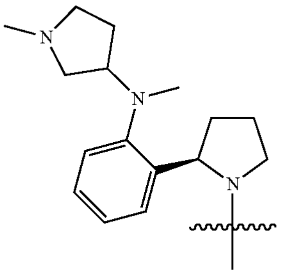
,
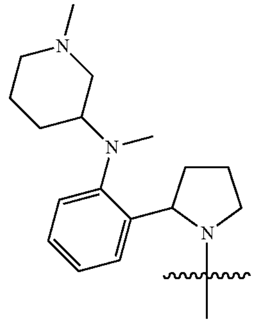
,
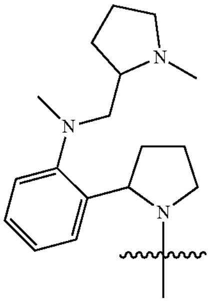
,
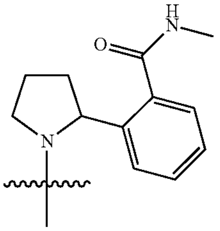
,
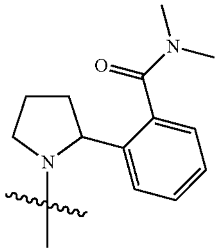
, and
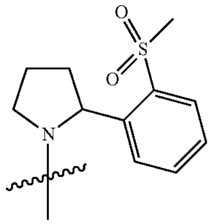
.

11. The compound of claim 1, wherein $L^2$ is a direct bond, $—(CR^aR^b)_{1-4}—$, $—O—(CR^aR^b)_{1-3}—$, $—NH—(CR^aR^b)_{0-2}—(CR^aR^b)_{0-2}—$, $—(CR^aR^b)_{0-2}—(CR^aR^b)_{0-2}—NH—$, or $—(CR^aR^b)_{0-2}—(NH)_{0-2}—C(O)—$, wherein $R^a$ and $R^b$ are hydrogen.

12. The compound of claim 1, wherein CyC is cycloalkyl or heterocyclyl, each of which is optionally substituted with one or two substituents $R^{5a}$, $R^{5a}$ is independently selected from hydrogen, halogen, cyano, oxo, $—OR^{5b}$, $—NR^{5b}R^{5c}$, $—COR^{5b}$, $—SO_2R^{5b}$, $—C_{1-8}$alkyl, $—C_{2-8}$alkynyl, —cycloalkyl, or heterocyclyl; wherein each of said $—C_{1-8}$alkyl, and heterocyclyl is optionally substituted with one or two substituents $R^{5e}$ which is selected from hydrogen, halogen, cyano, $—OR^{5f}$, $—C_{1-8}$alkyl, —cycloalkyl, or heterocyclyl;

$R^{5b}$, and $R^{5c}$ are each independently hydrogen, $—C_{1-8}$ alkyl, or heterocyclyl;

wherein said $—C_{1-8}$ alkyl is optionally substituted with one or two substituents $R^{5e}$; wherein each of said $R^{5e}$ is hydrogen, $—NR^{5f}R^{5g}$, or —cycloalkyl;

$R^{5f}$ and $R^{5g}$ are each independently hydrogen or $—C_{1-8}$ alkyl.

13. The compound of claim 1, wherein CyC is 6-membered aryl or 6-membered heteroaryl, each of which is optionally substituted with one or two substituents $R^{5a}$.

14. The compound of claim 12, wherein CyC is monocyclic 4- to 6-membered heterocyclyl groups containing one or two heteroatoms selected from nitrogen, oxygen, or sulfur heteroatoms as ring members, each of which is optionally substituted with one or two substituents $R^{5a}$.

15. The compound of claim 12, wherein $R^{5a}$ is independently hydrogen, halogen, cyano, oxo, $—OR^{5b}$, $—NR^{5b}R^{5c}$, $—COR^{5b}$, $—SO_2R^{5b}$, $—C_{1-8}$alkyl, $—C_{2-8}$ alkynyl, monocyclic $C_{3-8}$cycloalkyl, or monocyclic 4 to 9-membered heterocyclyl group containing one or two heteroatoms selected from nitrogen or oxygen or sulfur heteroatoms as ring members;

wherein each of said $—C_{1-8}$alkyl and monocyclic 4 to 9-membered heterocyclyl group is optionally substituted with one or two substituents $R^{5e}$.

16. The compound of claim 1, wherein m is 1 and $—L^2—$CyC is

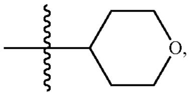
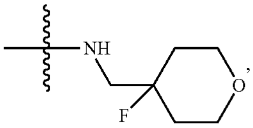
,
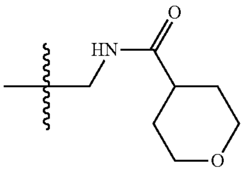
,
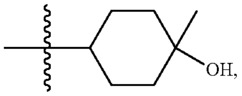
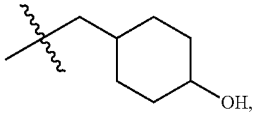
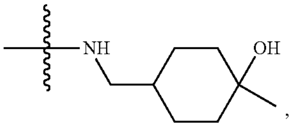
,
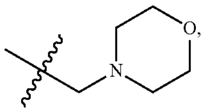
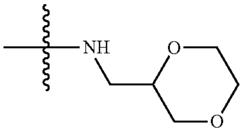
,
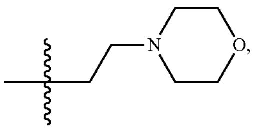
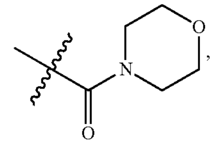
,
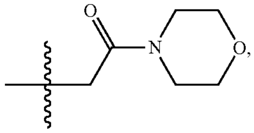
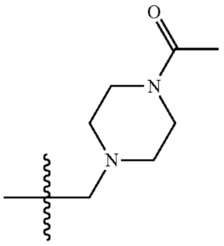
, -continued
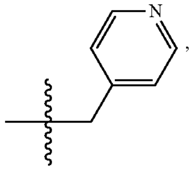
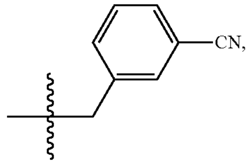
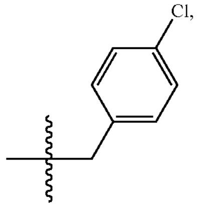
,
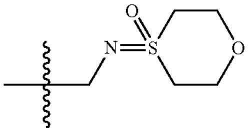
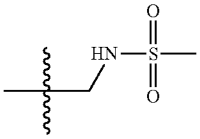
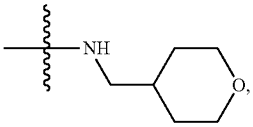
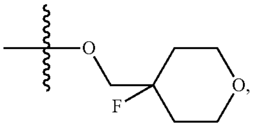
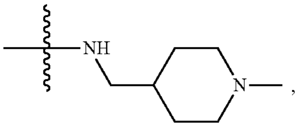
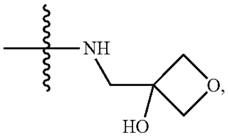
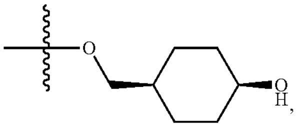
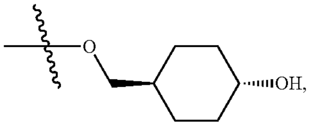
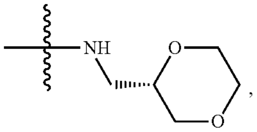
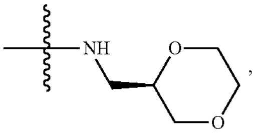
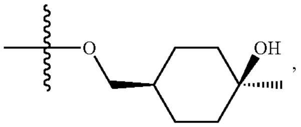
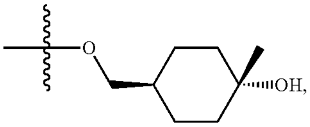
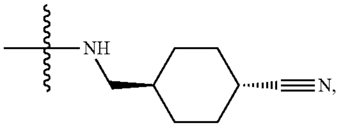
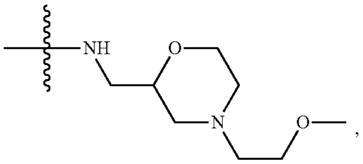
-continued
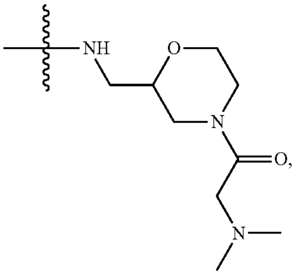
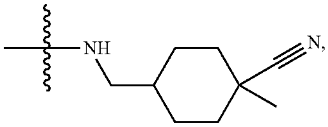
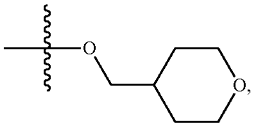
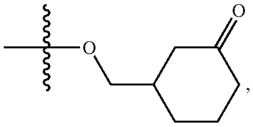
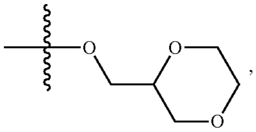
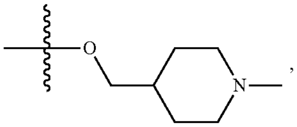
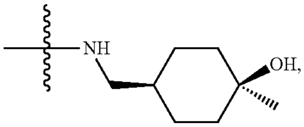
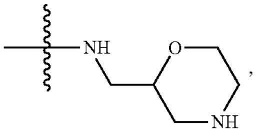
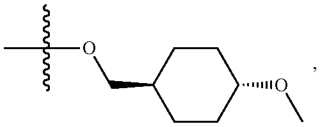
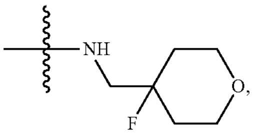
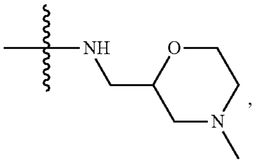
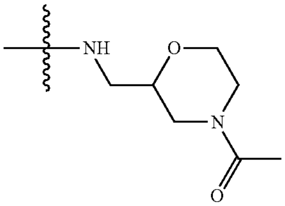
,
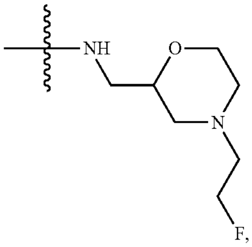
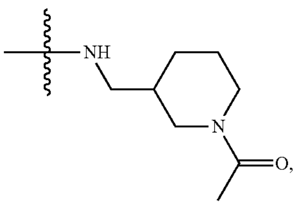
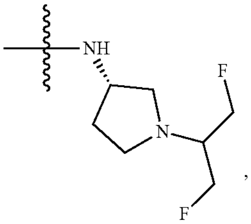

-continued
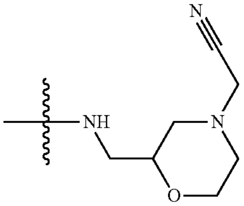
,
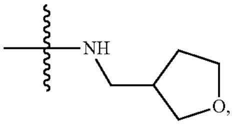
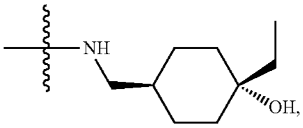
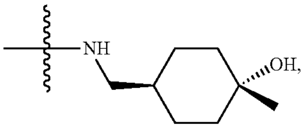
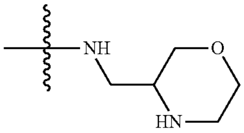
,
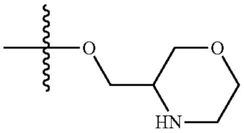
,
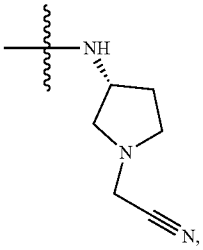
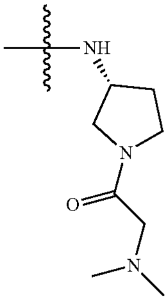
,
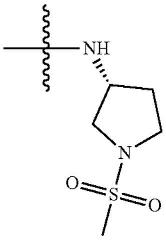
,
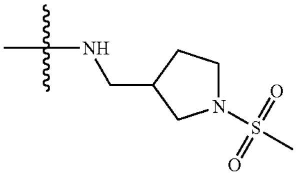
,
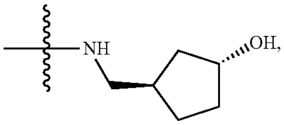
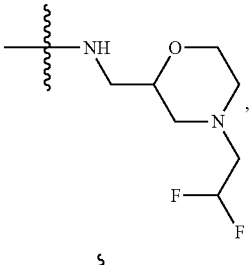
,
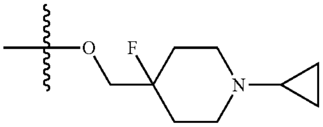
,
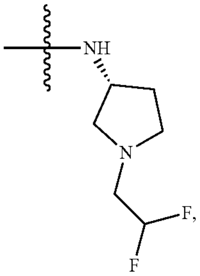
-continued
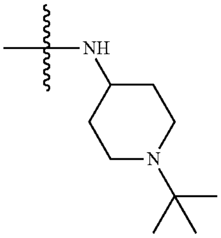
,
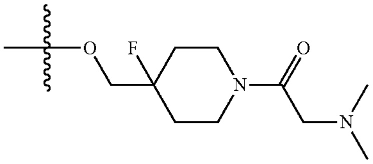
,
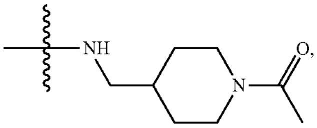
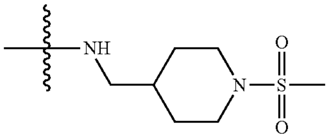
,
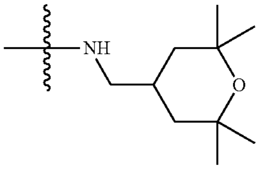
,
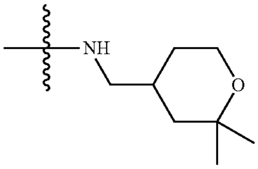
,
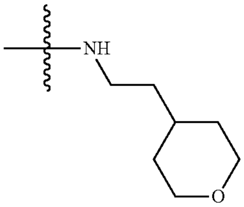
,
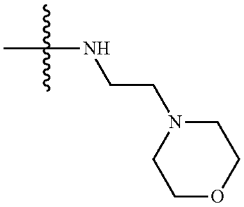
,
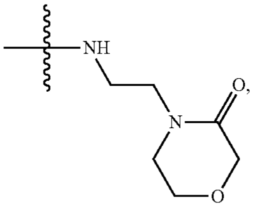
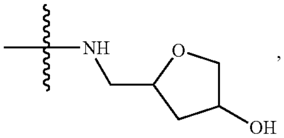
,
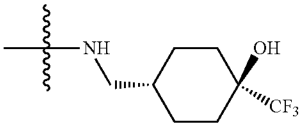
or
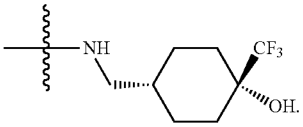

17. A compound, wherein the compound is selected from:
A1
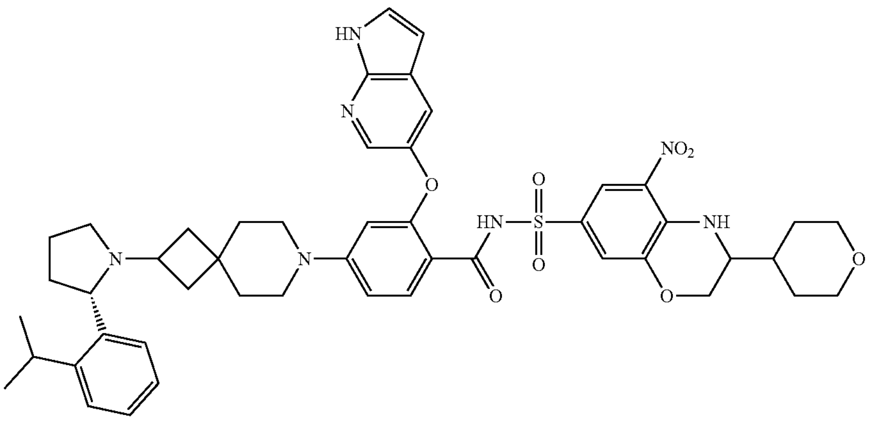
A2
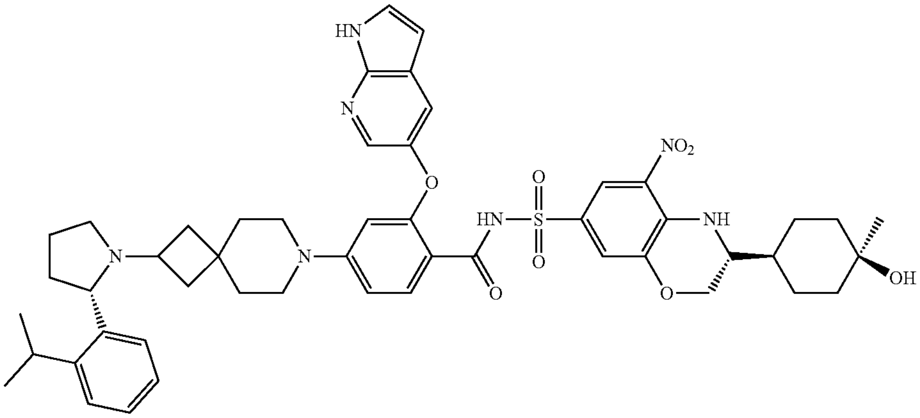
A3
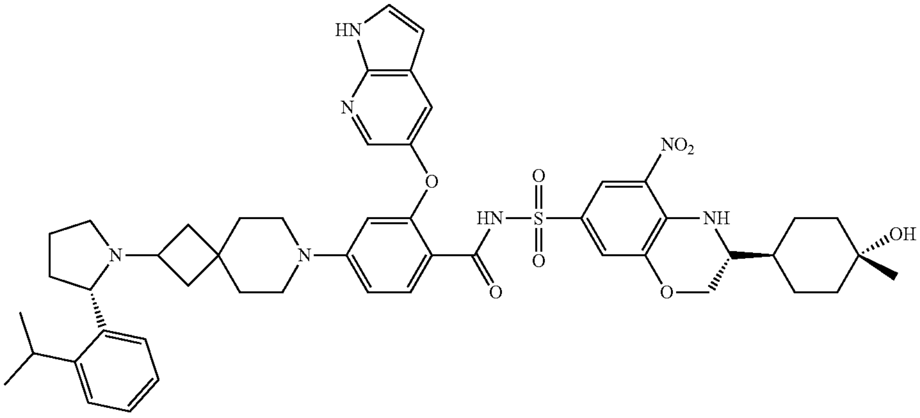

-continued
A4
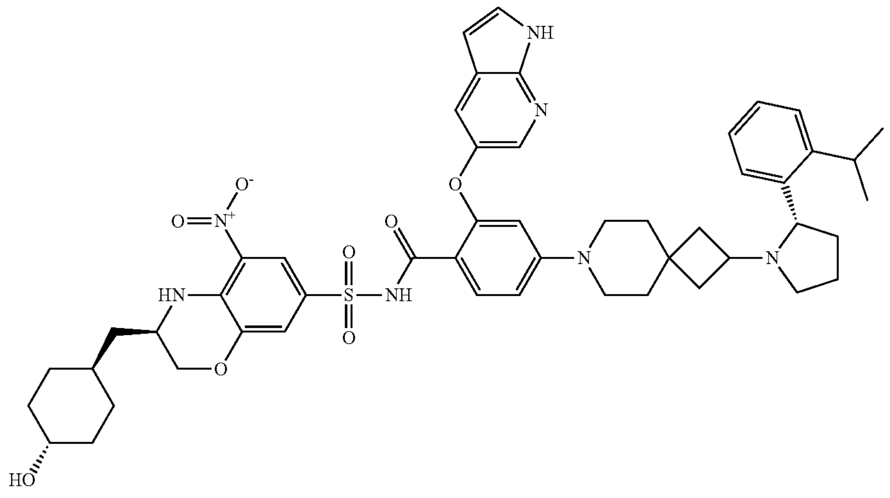
A5
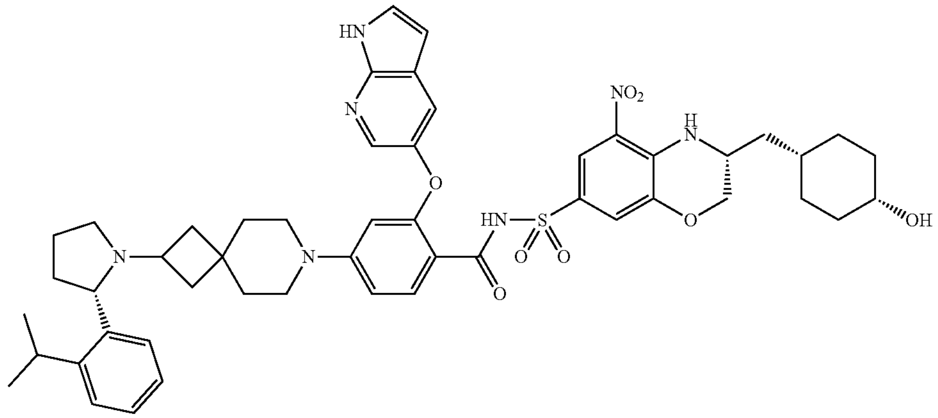
A6
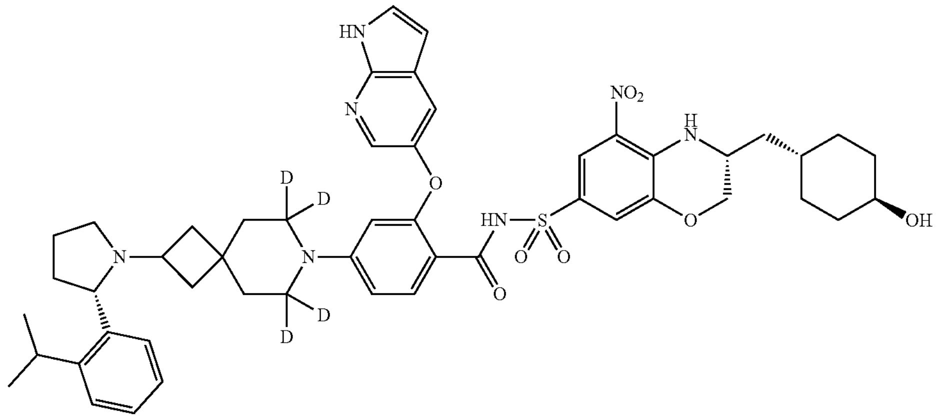

-continued
A7
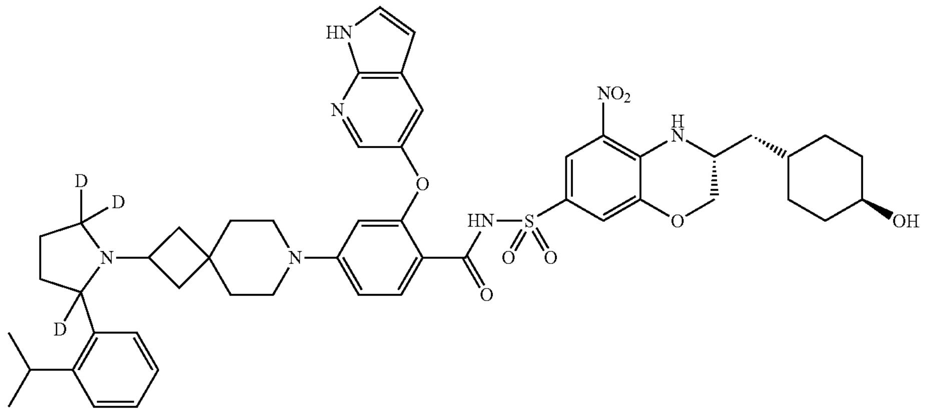
A8
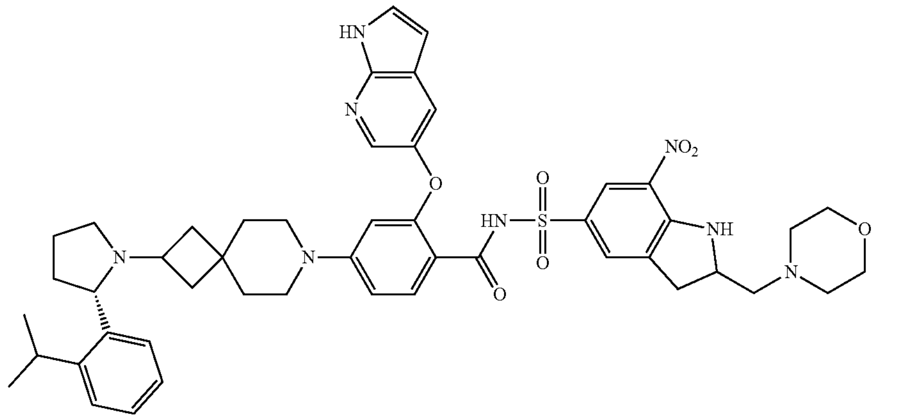
B1
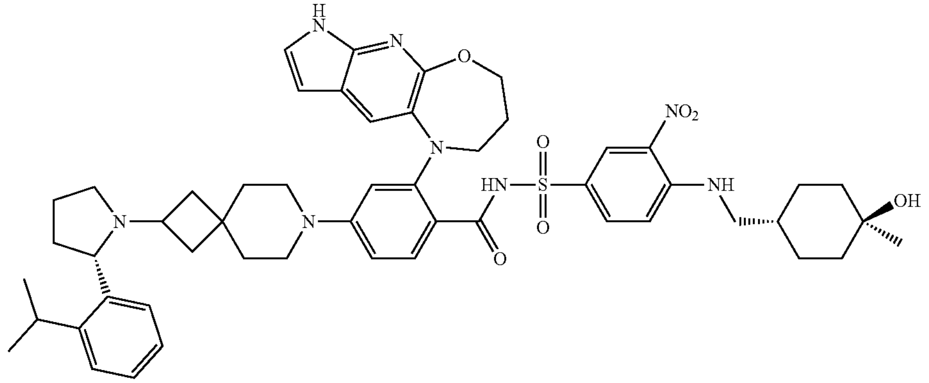
B2
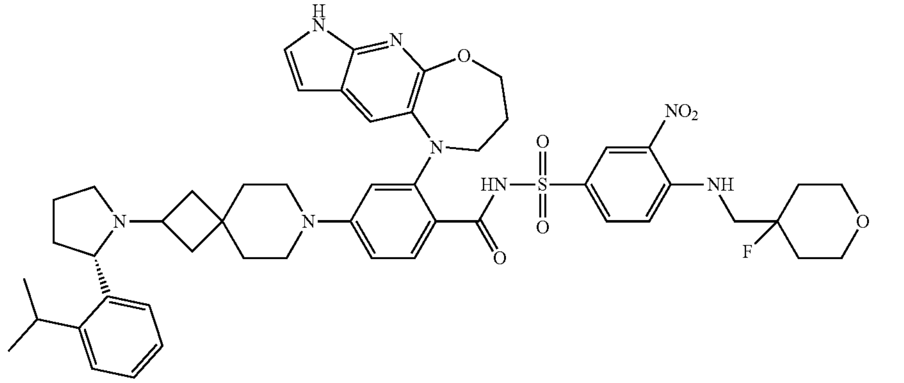

-continued
B3
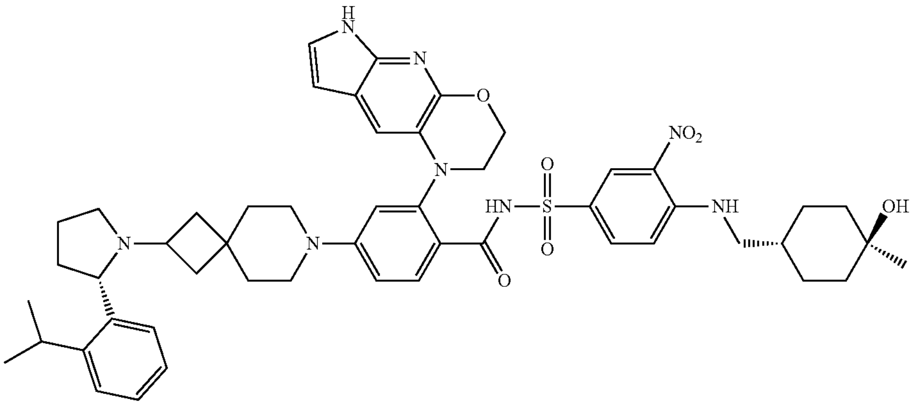
B4
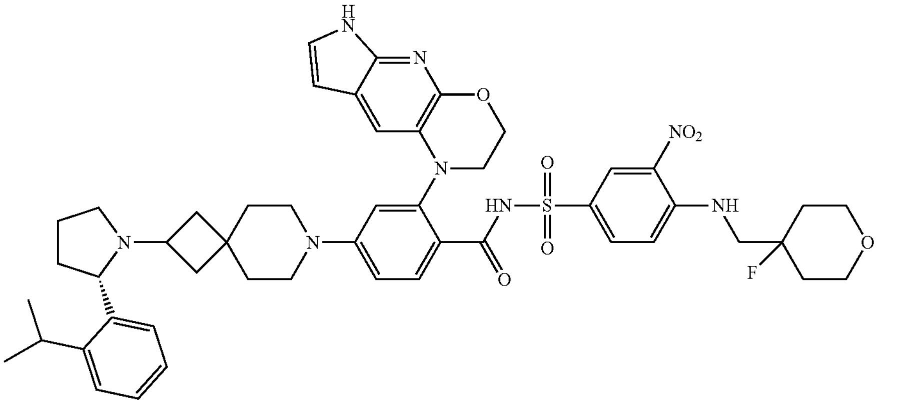
B5
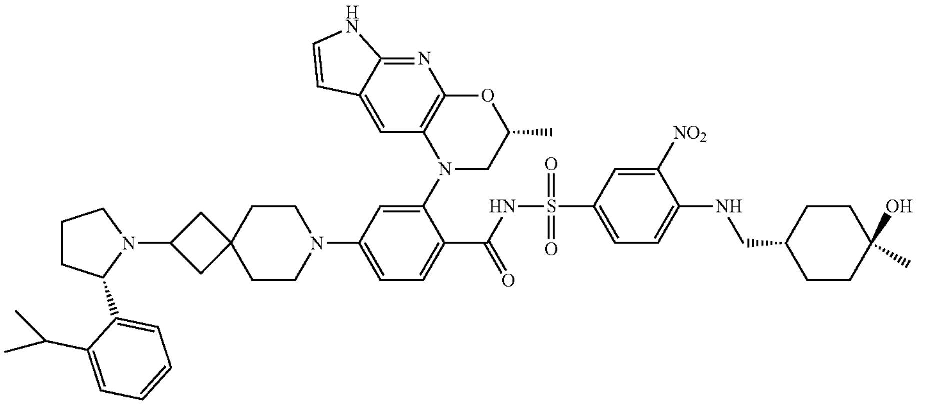
B6
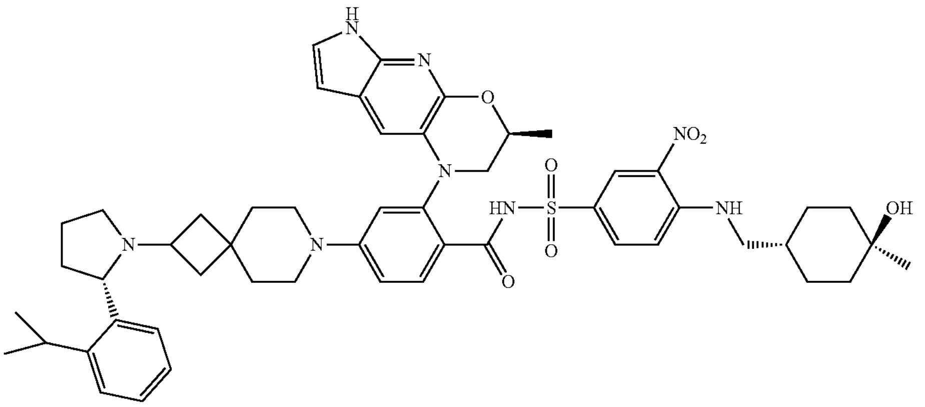

-continued
B7
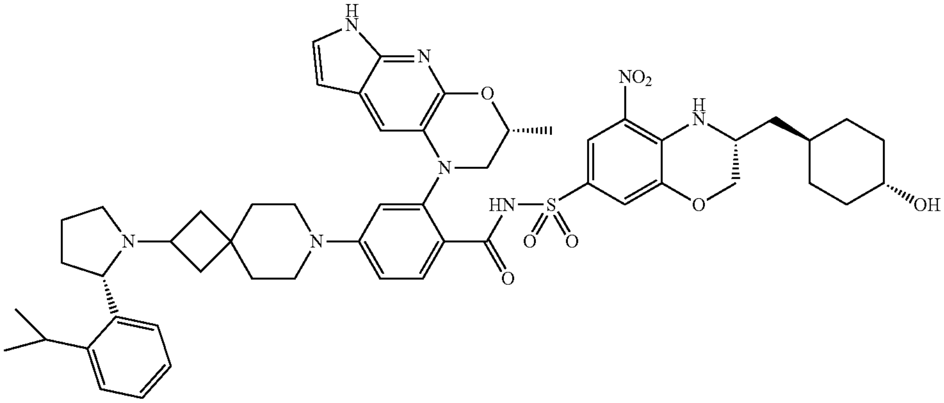
B8
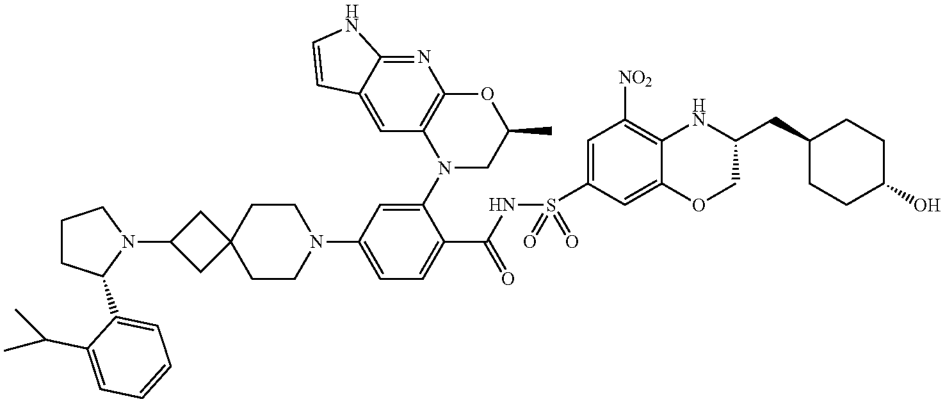
B9
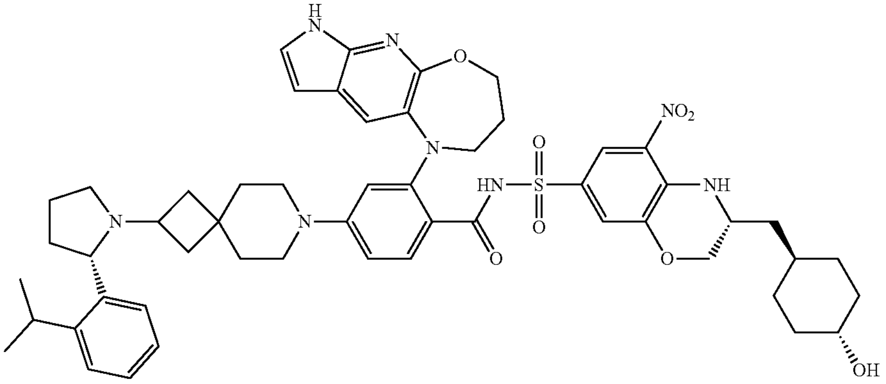
B10
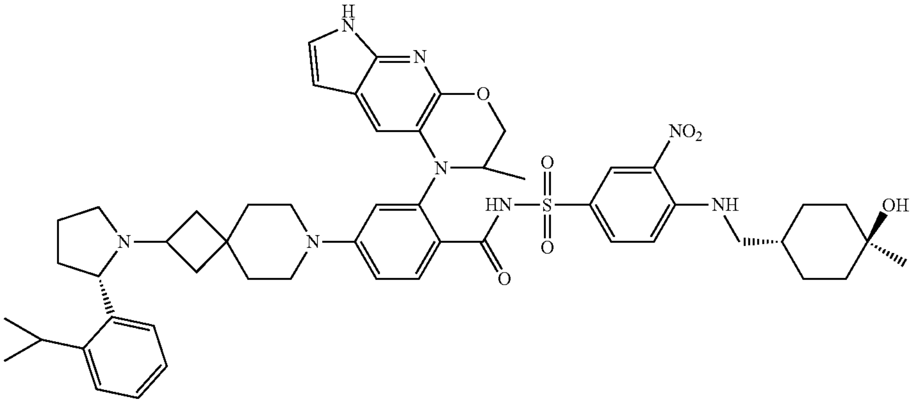

-continued
B11
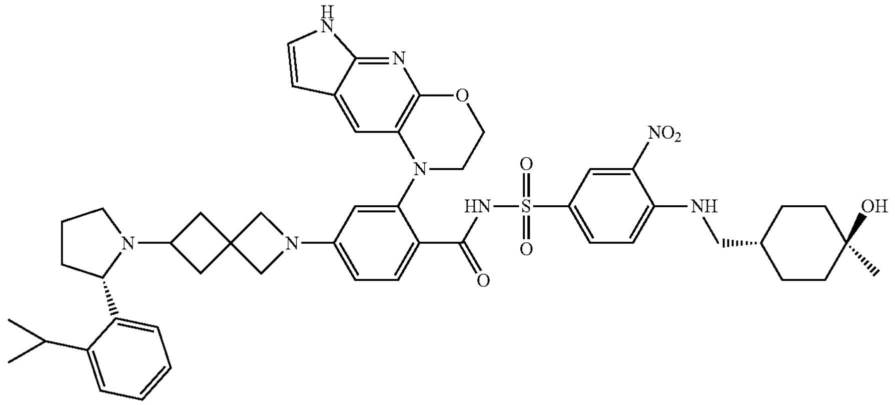
B12
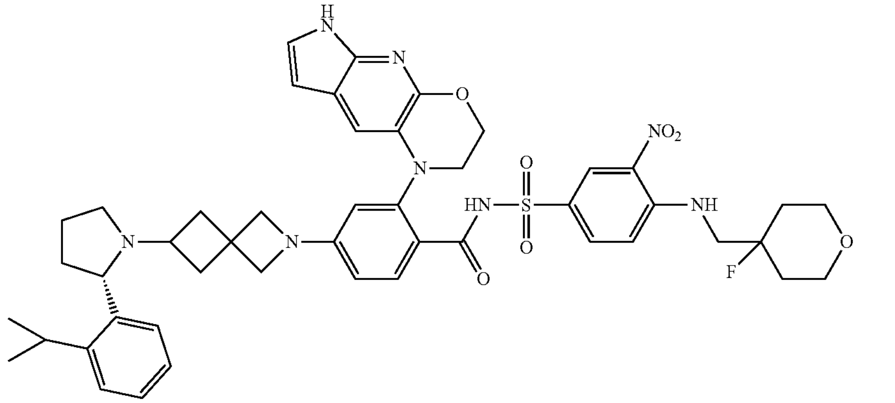
B13
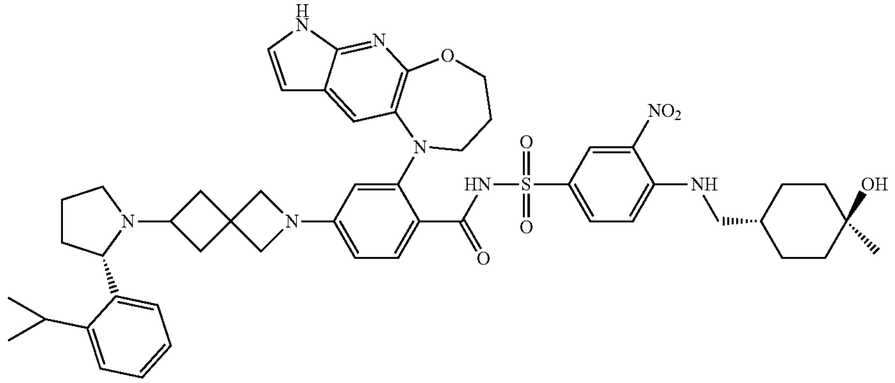
B14
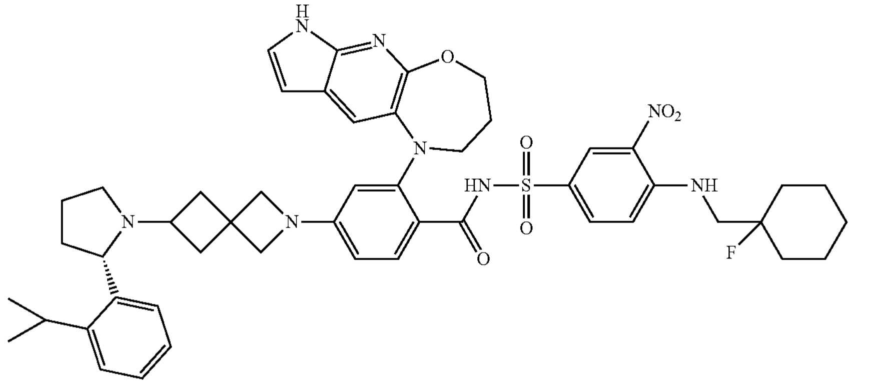

-continued
B15
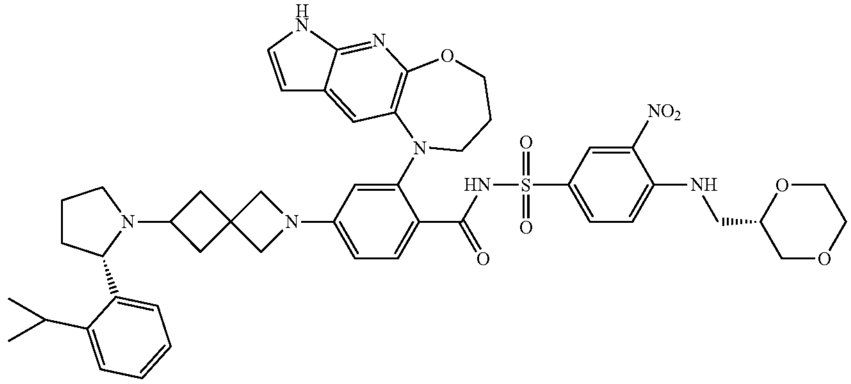
or a pharmaceutically acceptable salt thereof, or a stereoisomer thereof.
18. A pharmaceutical composition comprising the compound of claim 1, or a pharmaceutically acceptable salt thereof, or a stereoisomer thereof, and a pharmaceutically acceptable carrier.
* * * * *